United States Patent
Bressi et al.

(10) Patent No.: US 7,399,884 B2
(45) Date of Patent: *Jul. 15, 2008

(54) HISTONE DEACETYLASE INHIBITORS

(75) Inventors: Jerome C. Bressi, San Diego, CA (US); Sheldon X. Cao, San Diego, CA (US); Jeffrey A. Stafford, San Diego, CA (US); Phong H. Vu, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/557,402

(22) Filed: Nov. 7, 2006

(65) Prior Publication Data

US 2007/0149495 A1    Jun. 28, 2007

Related U.S. Application Data

(63) Continuation of application No. 10/681,049, filed on Oct. 7, 2003, now Pat. No. 7,154,002.

(60) Provisional application No. 60/417,238, filed on Oct. 8, 2002.

(51) Int. Cl.
*C07C 259/04* (2006.01)
*C07C 229/34* (2006.01)
*C07D 231/16* (2006.01)
*C07D 239/22* (2006.01)
*C07D 241/36* (2006.01)

(52) U.S. Cl. .................. 562/623; 560/39; 548/371.7; 544/316; 544/355

(58) Field of Classification Search .................. None
See application file for complete search history.

(56) References Cited

U.S. PATENT DOCUMENTS

| | | |
|---|---|---|
| 4,482,571 A | 11/1984 | Abraham |
| 4,997,815 A | 3/1991 | Perrine et al. |
| 5,124,342 A | 6/1992 | Kerdesky et al. |
| 5,216,004 A | 6/1993 | Perrine |
| 5,439,939 A | 8/1995 | Perrine |
| 5,569,675 A | 10/1996 | Rephaeli et al. |
| 5,645,852 A | 7/1997 | Newmark |
| 5,656,644 A | 8/1997 | Adams et al. |
| 5,700,826 A | 12/1997 | Mjalli et al. |
| 5,858,365 A | 1/1999 | Faller |
| 5,922,837 A | 7/1999 | Meinke et al. |
| 5,939,455 A | 8/1999 | Rephaeli |
| 5,939,456 A | 8/1999 | Perrine |
| 5,993,845 A | 11/1999 | Geerts et al. |
| 6,011,000 A | 1/2000 | Perrine et al. |
| 6,030,961 A | 2/2000 | Nudelman et al. |
| 6,040,342 A | 3/2000 | Rephaeli et al. |
| 6,043,277 A | 3/2000 | Rephaeli et al. |
| 6,043,389 A | 3/2000 | Nudelman et al. |
| 6,068,987 A | 5/2000 | Dulski et al. |
| 6,071,923 A | 6/2000 | Nudelman et al. |
| 6,110,697 A | 8/2000 | Dulski et al. |
| 6,110,955 A | 8/2000 | Nudelman et al. |
| 6,110,970 A | 8/2000 | Nudelman et al. |
| 6,124,495 A | 9/2000 | Neiss et al. |
| 6,130,248 A | 10/2000 | Nudelman et al. |
| 6,174,905 B1 | 1/2001 | Suzuki et al. |
| 6,197,743 B1 | 3/2001 | Faller |
| 6,231,880 B1 | 5/2001 | Perrine |
| 6,235,474 B1 | 5/2001 | Feinberg |
| 6,239,176 B1 | 5/2001 | Nudelman et al. |
| 6,262,116 B1 | 7/2001 | Pandolfi et al. |
| 6,287,790 B1 | 9/2001 | Lelievre et al. |
| 6,329,402 B1 | 12/2001 | Kikuchi et al. |
| 6,335,170 B1 | 1/2002 | Orntoft |
| 6,372,957 B1 | 4/2002 | Olson |

(Continued)

FOREIGN PATENT DOCUMENTS

WO    WO 96/15096 A1    5/1996

(Continued)

OTHER PUBLICATIONS

Database CAPLUS on STN, Acc. No. 1999:353256, Tomizaki et al., Peptide Science (1999), Volume Date 1998, 35th, p. 181-184 (abstract).

*Primary Examiner*—Brian J. Davis
(74) *Attorney, Agent, or Firm*—C. Amy Smith

(57) ABSTRACT

Histone deacetylase inhibitors and uses thereof are provided that have the general formula $$\begin{array}{c} R_1 \\ | \\ N \\ | \\ R_2 \end{array} \overset{O}{\underset{}{\text{—}}} \underset{\underset{R_4}{|}}{\overset{}{\text{—}}} \underset{R_5 \text{—} R_3}{\overset{}{\text{—}}} L \text{—} M$$

wherein $R_1$, $R_2$, $R_3$ and $R_4$ are each independently selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, with the proviso that $R_3$ and $R_4$ are not both hydrogen;

$R_5$ is selected from the group consisting of a carbonyl, a substituted or unsubstituted $C_{1-3}$ alkyl, a substituted or unsubstituted —$C_{1-3}$ alkyl-C(O), a substituted or unsubstituted —C(O)—$C_{1-3}$ alkyl, and a substituted or unsubstituted —C(O)C(O)$C_{1-3}$ alkyl;

M is a substituent capable of complexing with a protein metal ion; and

L is a substituent comprising a chain of 3-12 atoms connecting the M substituent to the carbon atom alpha to the L substituent.

56 Claims, 19 Drawing Sheets

U.S. PATENT DOCUMENTS

| | | |
|---|---|---|
| 6,376,508 B1 | 4/2002 | Li et al. |
| 6,387,673 B1 | 5/2002 | Evans et al. |
| 6,399,568 B1 | 6/2002 | Nishino et al. |
| 6,403,555 B1 | 6/2002 | Skov |
| 6,428,983 B1 | 8/2002 | Dulski et al. |
| 6,451,334 B2 | 9/2002 | Perrine et al. |
| 6,479,629 B2 | 11/2002 | Baldwin et al. |
| 6,495,719 B2 | 12/2002 | Lan-Hargest et al. |
| 6,506,574 B1 | 1/2003 | Rambhatla et al. |
| 6,511,990 B1 | 1/2003 | Breslow et al. |
| 6,512,123 B2 | 1/2003 | Grossmann et al. |
| 6,518,012 B1 | 2/2003 | Tomasi |
| 6,531,472 B2 | 3/2003 | Georges et al. |
| 6,538,030 B2 | 3/2003 | Chung et al. |
| 6,541,661 B1 | 4/2003 | Delorme et al. |
| 6,544,957 B2 | 4/2003 | Kern et al. |
| 6,548,479 B1 | 4/2003 | Skov |
| 6,552,065 B2 | 4/2003 | Remiszewski et al. |
| 6,562,995 B1 | 5/2003 | Lan-Hargest et al. |
| 6,599,937 B1 | 7/2003 | Neiss et al. |
| 6,632,628 B1 | 10/2003 | Olson et al. |
| 6,638,530 B1 | 10/2003 | Ishibashi et al. |
| 6,656,905 B1 | 12/2003 | Mori et al. |
| 6,673,587 B1 | 1/2004 | Evans et al. |
| 6,689,558 B2 | 2/2004 | Case |
| 6,699,902 B2 | 3/2004 | Lan-Hargest et al. |
| 6,706,686 B2 | 3/2004 | Long et al. |
| 6,706,762 B1 | 3/2004 | Evans et al. |
| 6,720,445 B2 | 4/2004 | Lan-Hargest et al. |
| 6,777,217 B1 | 8/2004 | Schreiber et al. |
| 6,784,173 B2 | 8/2004 | Leser-Reiff et al. |
| 6,800,638 B2 | 10/2004 | Georges et al. |
| 6,809,118 B2 | 10/2004 | Chung |
| 6,825,317 B2 | 11/2004 | Nishino et al. |
| 6,828,302 B1 | 12/2004 | Skov |
| 6,831,061 B2 | 12/2004 | Lee et al. |
| 6,833,384 B2 | 12/2004 | Remiszewski et al. |
| 6,841,565 B1 | 1/2005 | Lucas et al. |
| 6,869,953 B2 | 3/2005 | Haag et al. |
| 6,875,598 B1 | 4/2005 | Buggy |
| 6,884,597 B1 | 4/2005 | Taya et al. |
| 6,888,027 B2 | 5/2005 | Watkins et al. |
| 6,897,220 B2 | 5/2005 | Delorme et al. |
| 6,905,669 B2 | 6/2005 | DiMartino |
| 7,154,002 B1 * | 12/2006 | Bressi et al. ............... 562/623 |
| 2001/0009922 A1 | 7/2001 | Faller |
| 2001/0012836 A1 | 8/2001 | Hu et al. |
| 2001/0027215 A1 | 10/2001 | Perrine et al. |
| 2001/0034367 A1 | 10/2001 | Faller et al. |
| 2002/0061860 A1 | 5/2002 | Li et al. |
| 2002/0065282 A1 | 5/2002 | Georges et al. |
| 2002/0076457 A1 | 6/2002 | Aylward |
| 2002/0103192 A1 | 8/2002 | Curtin et al. |
| 2002/0107404 A1 | 8/2002 | Prien et al. |
| 2002/0115177 A1 | 8/2002 | Zhu |
| 2002/0115826 A1 | 8/2002 | Delorme et al. |
| 2002/0119996 A1 | 8/2002 | Lan-Hargest et al. |
| 2002/0120099 A1 | 8/2002 | Nishino |
| 2002/0132792 A1 | 9/2002 | Prien et al. |
| 2002/0137162 A1 | 9/2002 | Li et al. |
| 2002/0137775 A1 | 9/2002 | Lan-Hargest et al. |
| 2002/0143037 A1 | 10/2002 | Lan-Hargest et al. |
| 2002/0143052 A1 | 10/2002 | Lan-Hargest et al. |
| 2002/0143055 A1 | 10/2002 | Lan-Hargest et al. |
| 2002/0143196 A1 | 10/2002 | Lan-Hargest et al. |
| 2002/0161045 A1 | 10/2002 | Lan-Hargest et al. |
| 2002/0164752 A1 | 11/2002 | Meyers |
| 2002/0177594 A1 | 11/2002 | Curtin et al. |
| 2002/0183388 A1 | 12/2002 | Gudas |
| 2002/0183513 A1 | 12/2002 | Grossmann et al. |
| 2003/0013176 A1 | 1/2003 | Pavletich et al. |
| 2003/0013757 A1 | 1/2003 | Leser-Reiff et al. |
| 2003/0017454 A1 | 1/2003 | Sukumar et al. |
| 2003/0018062 A1 | 1/2003 | Remiszewski et al. |
| 2003/0059812 A1 | 3/2003 | Richon et al. |
| 2003/0078216 A1 | 4/2003 | MacLeod et al. |
| 2003/0078369 A1 | 4/2003 | Meinke et al. |
| 2003/0082666 A1 | 5/2003 | Kammer et al. |
| 2003/0082668 A1 | 5/2003 | Tamai et al. |
| 2003/0083521 A1 | 5/2003 | Lan-Hargest et al. |
| 2003/0124101 A1 | 7/2003 | Gu et al. |
| 2003/0125306 A1 | 7/2003 | Lan-Hargest et al. |
| 2003/0129724 A1 | 7/2003 | Grozinger et al. |
| 2003/0134865 A1 | 7/2003 | Adcock et al. |
| 2003/0139404 A1 | 7/2003 | Haag et al. |
| 2003/0143712 A1 | 7/2003 | Verdin et al. |
| 2003/0144276 A1 | 7/2003 | Kikuchi et al. |
| 2003/0144340 A1 | 7/2003 | Long et al. |
| 2003/0148970 A1 | 8/2003 | Besterman et al. |
| 2003/0149261 A1 | 8/2003 | Schramm et al. |
| 2003/0152557 A1 | 8/2003 | Besterman et al. |
| 2003/0154032 A1 | 8/2003 | Pittman et al. |
| 2003/0165903 A1 | 9/2003 | Dang et al. |
| 2003/0165956 A1 | 9/2003 | Stevens et al. |
| 2003/0171409 A1 | 9/2003 | Lan-Hargest et al. |
| 2003/0187027 A1 | 10/2003 | Schreiber et al. |
| 2003/0206946 A1 | 11/2003 | Chung |
| 2003/0207325 A1 | 11/2003 | Guarente et al. |
| 2003/0207791 A1 | 11/2003 | Minucci et al. |
| 2003/0212121 A1 | 11/2003 | Kruger et al. |
| 2003/0216345 A1 | 11/2003 | Nakanishi et al. |
| 2003/0219832 A1 | 11/2003 | Klein et al. |
| 2003/0224040 A1 | 12/2003 | Baylin et al. |
| 2003/0224473 A1 | 12/2003 | McCafferty |
| 2003/0235873 A1 | 12/2003 | Krmer et al. |
| 2004/0002447 A1 | 1/2004 | Levine et al. |
| 2004/0002506 A1 | 1/2004 | Breslow et al. |
| 2004/0005574 A1 | 1/2004 | Guarente et al. |
| 2004/0014647 A1 | 1/2004 | Lee et al. |
| 2004/0018522 A1 | 1/2004 | Dangond et al. |
| 2004/0018968 A1 | 1/2004 | Sgouros et al. |
| 2004/0023944 A1 | 2/2004 | Lan-Hargest et al. |
| 2004/0024067 A1 | 2/2004 | Remiszewski et al. |
| 2004/0028607 A1 | 2/2004 | Verdin et al. |
| 2004/0029903 A1 | 2/2004 | Lan-Hargest et al. |
| 2004/0029922 A1 | 2/2004 | Lan-Hargest et al. |
| 2004/0043470 A1 | 3/2004 | Xiao |
| 2004/0053820 A1 | 3/2004 | Nakajima et al. |
| 2004/0053960 A1 | 3/2004 | Georges et al. |
| 2004/0058868 A1 | 3/2004 | James et al. |
| 2004/0072735 A1 | 4/2004 | Richon et al. |
| 2004/0072770 A1 | 4/2004 | Besterman et al. |
| 2004/0072849 A1 | 4/2004 | Schreiber et al. |
| 2004/0077046 A1 | 4/2004 | Cohen et al. |
| 2004/0077083 A1 | 4/2004 | Watt |
| 2004/0077084 A1 | 4/2004 | Watt et al. |
| 2004/0077578 A1 | 4/2004 | Monia et al. |
| 2004/0077591 A1 | 4/2004 | Dangond |
| 2004/0077698 A1 | 4/2004 | Georges et al. |
| 2004/0077726 A1 | 4/2004 | Watkins et al. |
| 2004/0081976 A1 | 4/2004 | Sidransky |
| 2004/0087631 A1 | 5/2004 | Bacopoulos et al. |
| 2004/0087652 A1 | 5/2004 | Gottlicher et al. |
| 2004/0087657 A1 | 5/2004 | Richon et al. |
| 2004/0091951 A1 | 5/2004 | Schultz |
| 2004/0091953 A1 | 5/2004 | Verdin et al. |
| 2004/0091967 A1 | 5/2004 | Kohler |
| 2004/0092431 A1 | 5/2004 | Hellberg |
| 2004/0092558 A1 | 5/2004 | Klimko et al. |
| 2004/0092572 A1 | 5/2004 | Renaud et al. |
| 2004/0092598 A1 | 5/2004 | Watkins et al. |
| 2004/0097439 A9 | 5/2004 | Nicolas et al. |
| 2004/0102458 A1 | 5/2004 | Chiosis et al. |
| 2004/0106599 A1 | 6/2004 | Delorme et al. |

| | | | |
|---|---|---|---|
| 2004/0122079 A1 | 6/2004 | Grossmann et al. | |
| 2004/0122101 A1 | 6/2004 | Miller et al. | |
| 2004/0127522 A1 | 7/2004 | Chiao et al. | |
| 2004/0127523 A1 | 7/2004 | Bacopoulos et al. | |
| 2004/0127571 A1 | 7/2004 | Bhalla et al. | |
| 2004/0138270 A1 | 7/2004 | George et al. | |
| 2004/0157841 A1 | 8/2004 | Fertig et al. | |
| 2004/0157924 A1 | 8/2004 | Lan-Hargest et al. | |
| 2004/0157930 A1 | 8/2004 | Mascagni et al. | |
| 2004/0161787 A1 | 8/2004 | Michnick et al. | |
| 2004/0162317 A1 | 8/2004 | Fertig et al. | |
| 2004/0167184 A1 | 8/2004 | Wiech et al. | |
| 2004/0180962 A1 | 9/2004 | Truog | |
| 2004/0186049 A1 | 9/2004 | Long et al. | |
| 2004/0186274 A1 | 9/2004 | Allis et al. | |
| 2004/0192744 A1 | 9/2004 | Haag et al. | |
| 2004/0197888 A1 | 10/2004 | Christopher et al. | |
| 2004/0198830 A1 | 10/2004 | Watkins et al. | |
| 2004/0204339 A1 | 10/2004 | DiMartino | |
| 2004/0204373 A1 | 10/2004 | Monia et al. | |
| 2004/0213826 A1 | 10/2004 | Marx et al. | |
| 2004/0214862 A1 | 10/2004 | Leser-Reiff et al. | |
| 2004/0214880 A1 | 10/2004 | Fertig et al. | |
| 2004/0224991 A1 | 11/2004 | Lu et al. | |
| 2004/0229889 A1 | 11/2004 | Urano et al. | |
| 2004/0254220 A1 | 12/2004 | Bressi et al. | |
| 2004/0259772 A1 | 12/2004 | Fojo et al. | |
| 2004/0266718 A1 | 12/2004 | Li et al. | |
| 2004/0266769 A1 | 12/2004 | Bressi et al. | |
| 2004/0266818 A1 | 12/2004 | Breslow et al. | |
| 2005/0003031 A1 | 1/2005 | Aylward | |
| 2005/0009030 A1 | 1/2005 | Schweighoffer et al. | |
| 2005/0020557 A1 | 1/2005 | Johnson et al. | |
| 2005/0026907 A1 | 2/2005 | Wash et al. | |
| 2005/0032794 A1 | 2/2005 | Padia et al. | |
| 2005/0032831 A1 | 2/2005 | Kozikowski et al. | |
| 2005/0032899 A1 | 2/2005 | Chen et al. | |
| 2005/0037992 A1 | 2/2005 | Lyons et al. | |
| 2005/0038113 A1 | 2/2005 | Groner et al. | |
| 2005/0059682 A1 | 3/2005 | Rubinfield | |
| 2005/0065596 A1 | 3/2005 | Tseng et al. | |
| 2005/0070467 A1 | 3/2005 | Naoe | |
| 2005/0079995 A1 | 4/2005 | Bedaloy et al. | |
| 2005/0080249 A1 | 4/2005 | Buggy | |
| 2005/0084967 A1 | 4/2005 | Berenson et al. | |
| 2005/0085507 A1 | 4/2005 | Remiszewski et al. | |
| 2005/0085515 A1 | 4/2005 | Watkins et al. | |
| 2005/0096468 A1 | 5/2005 | Van Emelen et al. | |
| 2005/0106654 A1 | 5/2005 | Olson et al. | |
| 2005/0107348 A1 | 5/2005 | Lan-Hargest et al. | |
| 2005/0107384 A1 | 5/2005 | Angibaud et al. | |
| 2005/0107445 A1 | 5/2005 | Watkins et al. | |
| 2005/0113373 A1 | 5/2005 | Van Emelen et al. | |
| 2005/0118596 A1 | 6/2005 | Asselbergs et al. | |
| 2005/0119250 A1 | 6/2005 | Angibaud et al. | |
| 2005/0124679 A1 | 6/2005 | Kim et al. | |
| 2005/0130146 A1 | 6/2005 | Zelent et al. | |
| 2005/0131018 A1 | 6/2005 | Sendzik et al. | |
| 2005/0136090 A1 | 6/2005 | Falotico et al. | |
| 2005/0137232 A1 | 6/2005 | Bressi et al. | |
| 2005/0137234 A1 | 6/2005 | Bressi et al. | |
| 2005/0143385 A1 | 6/2005 | Watkins et al. | |
| 2005/0148613 A1 | 7/2005 | Van Emelen et al. | |
| 2005/0159347 A1 | 7/2005 | DiMartino | |
| 2005/0159470 A1 | 7/2005 | Bressi et al. | |
| 2005/0165016 A1 | 7/2005 | Van Emelen | |
| 2005/0171027 A1 | 8/2005 | Sinclair et al. | |
| 2005/0171042 A1 | 8/2005 | Monia et al. | |
| 2005/0171103 A1 | 8/2005 | Stokes et al. | |
| 2005/0171208 A1 | 8/2005 | Lan-Hargest et al. | |
| 2005/0171347 A1 | 8/2005 | Emelen et al. | |
| 2005/0176686 A1 | 8/2005 | Maurer et al. | |
| 2005/0176764 A1 | 8/2005 | Mataki et al. | |
| 2005/0187261 A1 | 8/2005 | Verner et al. | |
| 2005/0191713 A1 | 9/2005 | Sasakawa et al. | |

FOREIGN PATENT DOCUMENTS

| | | |
|---|---|---|
| WO | WO 97/02244 A1 | 1/1997 |
| WO | WO 97/11366 A1 | 3/1997 |
| WO | WO 97/35990 A2 | 10/1997 |
| WO | WO 97/35990 A3 | 10/1997 |
| WO | WO 97/47307 A1 | 12/1997 |
| WO | WO 98/00127 A1 | 1/1998 |
| WO | WO 98/28269 A1 | 7/1998 |
| WO | WO 98/29114 A1 | 7/1998 |
| WO | WO 98/39966 A1 | 9/1998 |
| WO | WO 98/40065 A1 | 9/1998 |
| WO | WO 98/40080 A1 | 9/1998 |
| WO | WO 98/48825 A1 | 11/1998 |
| WO | WO 98/55449 A1 | 12/1998 |
| WO | WO 99/11659 A1 | 3/1999 |
| WO | WO 99/23885 A1 | 5/1999 |
| WO | WO 99/37150 A1 | 7/1999 |
| WO | WO 99/61413 A1 | 12/1999 |
| WO | WO 00/08048 A2 | 2/2000 |
| WO | WO 00/08048 A3 | 2/2000 |
| WO | WO 00/010583 A1 | 3/2000 |
| WO | WO 00/021979 A2 | 4/2000 |
| WO | WO 00/021979 A3 | 4/2000 |
| WO | WO 00/023567 A2 | 4/2000 |
| WO | WO 00/023567 A3 | 4/2000 |
| WO | WO 00/52033 A1 | 9/2000 |
| WO | WO 00/56917 A1 | 9/2000 |
| WO | WO 03/082288 A1 | 9/2000 |
| WO | WO 00/61576 A1 | 10/2000 |
| WO | WO 00/118045 A1 | 10/2000 |
| WO | WO 00/71703 A2 | 11/2000 |
| WO | WO 00/71703 A3 | 11/2000 |
| WO | WO 01/07042 A1 | 2/2001 |
| WO | WO 01/14581 A3 | 3/2001 |
| WO | WO 01/16106 A1 | 3/2001 |
| WO | WO 01/17514 A1 | 3/2001 |
| WO | WO 01/018045 A1 | 3/2001 |
| WO | WO 01/18171 A2 | 3/2001 |
| WO | WO 01/18171 A3 | 3/2001 |
| WO | WO 01/27314 A1 | 4/2001 |
| WO | WO 01/38322 A1 | 5/2001 |
| WO | WO 01/42437 A2 | 6/2001 |
| WO | WO 01/67107 A1 | 9/2001 |
| WO | WO 01/70675 A3 | 9/2001 |
| WO | WO 01/72737 A1 | 10/2001 |
| WO | WO 01/72784 A2 | 10/2001 |
| WO | WO 01/72784 A3 | 10/2001 |
| WO | WO 02/06307 A1 | 1/2002 |
| WO | WO 02/07722 A2 | 1/2002 |
| WO | WO 02/07722 A3 | 1/2002 |
| WO | WO 02/08273 A2 | 1/2002 |
| WO | WO 02/08273 A3 | 1/2002 |
| WO | WO 02/15921 A2 | 2/2002 |
| WO | WO 02/15921 A3 | 2/2002 |
| WO | WO 02/22133 A1 | 3/2002 |
| WO | WO 02/22577 A3 | 3/2002 |
| WO | WO 02/26696 A1 | 4/2002 |
| WO | WO 02/26703 | 4/2002 |
| WO | WO 02/30879 A2 | 4/2002 |
| WO | WO 02/30879 A3 | 4/2002 |
| WO | WO 02/30970 A2 | 4/2002 |
| WO | WO 02/30970 A3 | 4/2002 |
| WO | WO 02/36075 A2 | 5/2002 |
| WO | WO 02/36075 A3 | 5/2002 |
| WO | WO 02/36783 A2 | 5/2002 |
| WO | WO 0236783 A3 | 5/2002 |
| WO | WO 01/42437 A3 | 6/2002 |
| WO | WO 02/46129 A2 | 6/2002 |
| WO | WO 02/46129 A3 | 6/2002 |

| | | | | | | | |
|---|---|---|---|---|---|---|---|
| WO | WO 02/46144 | A1 | 6/2002 | WO | WO 03/086397 | A1 | 10/2003 |
| WO | WO 02/50244 | A3 | 6/2002 | WO | WO 03/087057 | A1 | 10/2003 |
| WO | WO/0250285 | A2 | 6/2002 | WO | WO 03/087066 | A1 | 10/2003 |
| WO | WO/0250285 | A3 | 6/2002 | WO | WO 03/088954 | A1 | 10/2003 |
| WO | WO 02/051842 | A1 | 7/2002 | WO | WO 03/092686 | A1 | 11/2003 |
| WO | WO 02/055017 | A3 | 7/2002 | WO | WO 03/000760 | A1 | 12/2003 |
| WO | WO 02/055688 | A2 | 7/2002 | WO | WO 03/099210 | A3 | 12/2003 |
| WO | WO 02/055688 | A3 | 7/2002 | WO | WO 03/099272 | A1 | 12/2003 |
| WO | WO 02/060430 | A1 | 8/2002 | WO | WO 03/099789 | A1 | 12/2003 |
| WO | WO 02/062773 | A1 | 8/2002 | WO | WO 03/100089 | A1 | 12/2003 |
| WO | WO 02/069947 | A2 | 9/2002 | WO | WO 03/103712 | A1 | 12/2003 |
| WO | WO 02/069947 | A3 | 9/2002 | WO | WO 2003/103613 | A2 | 12/2003 |
| WO | WO 02/083173 | A1 | 10/2002 | WO | WO 2003/103613 | A3 | 12/2003 |
| WO | WO 02/085400 | A1 | 10/2002 | WO | WO 2004/001072 | A2 | 12/2003 |
| WO | WO 2002/076941 | A2 | 10/2002 | WO | WO 04/002944 | A1 | 1/2004 |
| WO | WO 2002/076941 | A3 | 10/2002 | WO | WO 2004/005282 | A1 | 1/2004 |
| WO | WO O2/085883 | A1 | 10/2002 | WO | WO 2004/005513 | A2 | 1/2004 |
| WO | WO 02/089782 | A2 | 11/2002 | WO | WO 2004/006909 | A1 | 1/2004 |
| WO | WO 02/089782 | A3 | 11/2002 | WO | WO 2004/009092 | A1 | 1/2004 |
| WO | WO 02090534 | A1 | 11/2002 | WO | WO 2004/009536 | A1 | 1/2004 |
| WO | WO 02/102316 | A2 | 12/2002 | WO | WO 2004/009771 | A2 | 1/2004 |
| WO | WO 02/102316 | A3 | 12/2002 | WO | WO 2004/013130 | A1 | 2/2004 |
| WO | WO 02/102323 | A2 | 12/2002 | WO | WO 04/017996 | A1 | 3/2004 |
| WO | WO 02/102984 | A2 | 12/2002 | WO | WO 2004/020460 | A1 | 3/2004 |
| WO | WO 02/102984 | A3 | 12/2002 | WO | WO 2004/024160 | A1 | 3/2004 |
| WO | WO 03/000715 | A1 | 1/2003 | WO | WO 2004/026234 | A2 | 4/2004 |
| WO | WO 2003/006652 | A2 | 1/2003 | WO | WO 2004/027418 | A3 | 4/2004 |
| WO | WO 2003/006652 | A3 | 1/2003 | WO | WO 2004/029622 | A2 | 4/2004 |
| WO | WO 03/011851 | A3 | 2/2003 | WO | WO 2004/031388 | A1 | 4/2004 |
| WO | WO 03/013493 | A1 | 2/2003 | WO | WO 2004/035525 | A1 | 4/2004 |
| WO | WO 03/014340 | A2 | 2/2003 | WO | WO 2004/043348 | A2 | 5/2004 |
| WO | WO 03/014340 | A3 | 2/2003 | WO | WO 2004/043352 | A2 | 5/2004 |
| WO | WO 03/015810 | A1 | 2/2003 | WO | WO 04/052292 | A2 | 6/2004 |
| WO | WO 03/024442 | A2 | 3/2003 | WO | WO 04/052828 | A1 | 6/2004 |
| WO | WO 03/024442 | A3 | 3/2003 | WO | WO 04/053140 | A2 | 6/2004 |
| WO | WO 03/024448 | A2 | 3/2003 | WO | WO 2004/046094 | A1 | 6/2004 |
| WO | WO 03/024448 | A3 | 3/2003 | WO | WO 2004/046104 | A1 | 6/2004 |
| WO | WO 03/029451 | A2 | 4/2003 | WO | WO 2004/046312 | A2 | 6/2004 |
| WO | WO 03/029451 | A3 | 4/2003 | WO | WO 04/054999 | A1 | 7/2004 |
| WO | WO 03/032921 | A2 | 4/2003 | WO | WO 04/056877 | A1 | 7/2004 |
| WO | WO 03/032921 | A3 | 4/2003 | WO | WO 04/063146 | A1 | 7/2004 |
| WO | WO 03/033678 | A3 | 4/2003 | WO | WO 04/063169 | A1 | 7/2004 |
| WO | WO 03/039599 | A1 | 5/2003 | WO | WO 04/064727 | A2 | 8/2004 |
| WO | WO 03/046207 | A2 | 6/2003 | WO | WO 04/065354 | A1 | 8/2004 |
| WO | WO 03/048774 | A1 | 6/2003 | WO | WO 04/067480 | A2 | 8/2004 |
| WO | WO 03/053468 | A1 | 7/2003 | WO | WO 2004/069133 | A2 | 8/2004 |
| WO | WO 03/057722 | A2 | 7/2003 | WO | WO 2004/069803 | A2 | 8/2004 |
| WO | WO 03/057722 | A3 | 7/2003 | WO | WO 2004/069823 | A1 | 8/2004 |
| WO | WO 03/059864 | A2 | 7/2003 | WO | WO 2004/070351 | A2 | 8/2004 |
| WO | WO 03/059864 | A3 | 7/2003 | WO | WO 2004/071400 | A2 | 8/2004 |
| WO | WO 03/066579 | A2 | 8/2003 | WO | WO 2004/071401 | A2 | 8/2004 |
| WO | WO 03/066579 | A3 | 8/2003 | WO | WO 2004/071443 | A2 | 8/2004 |
| WO | WO 03/066885 | A2 | 8/2003 | WO | WO 2004/071464 | A2 | 8/2004 |
| WO | WO 03/066885 | A3 | 8/2003 | WO | WO 2004/072047 | A1 | 8/2004 |
| WO | WO 03/066889 | A2 | 8/2003 | WO | WO 2004/072265 | A2 | 8/2004 |
| WO | WO 03/066889 | A3 | 8/2003 | WO | WO 04/076386 | A2 | 9/2004 |
| WO | WO 03/070691 | A1 | 8/2003 | WO | WO 04/082638 | A2 | 9/2004 |
| WO | WO 03/070754 | A1 | 8/2003 | WO | WO 2004/074478 | A1 | 9/2004 |
| WO | WO 2003/070188 | A2 | 8/2003 | WO | WO 2004/089293 | A2 | 10/2004 |
| WO | WO 2003/070188 | A3 | 8/2003 | WO | WO 2004/092115 | A2 | 10/2004 |
| WO | WO 03/075929 | A1 | 9/2003 | WO | WO 2004/098495 | A2 | 11/2004 |
| WO | WO 03/076395 | A1 | 9/2003 | WO | WO 04/103358 | A2 | 12/2004 |
| WO | WO 03/076400 | A1 | 9/2003 | WO | WO 04/103369 | A1 | 12/2004 |
| WO | WO 03/076401 | A1 | 9/2003 | WO | WO 04/110418 | A2 | 12/2004 |
| WO | WO 03/076421 | A1 | 9/2003 | WO | WO 04/112763 | A2 | 12/2004 |
| WO | WO 03/076422 | A1 | 9/2003 | WO | WO 04/113336 | A1 | 12/2004 |
| WO | WO 03/076430 | A1 | 9/2003 | WO | WO 05/002555 | A2 | 1/2005 |
| WO | WO 03/076438 | A1 | 9/2003 | WO | WO 05/002672 | A2 | 1/2005 |
| WO | WO 2003/075839 | A2 | 9/2003 | WO | WO 05/004861 | A1 | 1/2005 |
| WO | WO 2003/075839 | A3 | 9/2003 | WO | WO 2005/000213 | A2 | 1/2005 |
| WO | WO 03/080864 | A1 | 10/2003 | WO | WO 2005/000282 | A2 | 1/2005 |
| WO | WO 03/083067 | A2 | 10/2003 | WO | WO 2005/000289 | A1 | 1/2005 |
| WO | WO 03/084611 | A1 | 10/2003 | WO | WO 2005/000332 | A2 | 1/2005 |

| | | | | | | | |
|---|---|---|---|---|---|---|---|
| WO | WO 2005/007091 A2 | 1/2005 | | WO | WO 05/034880 A2 | 4/2005 | |
| WO | WO 2005/007158 A1 | 1/2005 | | WO | WO 05/047457 A2 | 5/2005 | |
| WO | WO 05/011598 A2 | 2/2005 | | WO | WO 2005/039498 A2 | 5/2005 | |
| WO | WO 05/011661 A1 | 2/2005 | | WO | WO 2005/040101 A1 | 5/2005 | |
| WO | WO 05/013958 A1 | 2/2005 | | WO | WO 2005/040136 A1 | 5/2005 | |
| WO | WO 05/014004 A1 | 2/2005 | | WO | WO 2005/040161 A1 | 5/2005 | |
| WO | WO 05/014588 A1 | 2/2005 | | WO | WO 05/051901 A1 | 6/2005 | |
| WO | WO 05/016264 A2 | 2/2005 | | WO | WO 05/055928 A2 | 6/2005 | |
| WO | WO 2005/009349 A2 | 2/2005 | | WO | WO 05/055928 A3 | 6/2005 | |
| WO | WO 2005/016342 A1 | 2/2005 | | WO | WO 05/058298 A2 | 6/2005 | |
| WO | WO 05/018578 A2 | 3/2005 | | WO | WO 05/058803 A1 | 6/2005 | |
| WO | WO 05/019174 A1 | 3/2005 | | WO | WO 2005/053609 A2 | 6/2005 | |
| WO | WO 05/023179 A2 | 3/2005 | | WO | WO 2005/053610 A2 | 6/2005 | |
| WO | WO 05/025619 A1 | 3/2005 | | WO | WO 2005/065681 A1 | 7/2005 | |
| WO | WO 05/028447 A1 | 3/2005 | | WO | WO 2005/066151 A2 | 7/2005 | |
| WO | WO 05/028620 A2 | 3/2005 | | WO | WO 05/071079 A1 | 8/2005 | |
| WO | WO 05/030704 A1 | 4/2005 | | | | | |
| WO | WO 05/030705 A1 | 4/2005 | | | | | |

\* cited by examiner

FIGURE 3

Amino acid sequence for full length human wild type
HDAC8 [SEQ ID NO:1]

```
MEEPEEPADSGQSLVPVYIYSPEYVSMCDSLAKIPKRASMVHSLIEAYALHKQMRIVKPK   60
VASMEEMAAFHTDAYLQHLQKVSQEGDDDHPDSIEYGLGYDCPATEGIFDYAAAIGGATI  120
TAAQCLIDGMCKVAINWSGGWHHAKKDEASGFCYLNDAVLGILRLRRKFERILYVDLDLH  180
HGDGVEDAFSFTSKVMTVSLHKFSPGFFPGTGDVSDVGLGKGRYYSVNVPIQDGIQDEKY  240
YQICESVLKEVYQAFNPKAVVLQLGADTIAGDPMCSFNMTPVGIGKCLKYILQWQLATLI  300
LGGGGYNLANTARCWTYLTGVILGKTLSSEIPDHEFFTAYGPDYVLEITPSCRPDRNEPH  360
RIQQILNYIKGNLKHVV                                             377
```

Human cDNA sequence HDAC8 [SEQ ID NO:2]

```
ATGGAGGAGCCGGAGGAACCGGCGGACAGTGGGCAGTCGCTGGTCCCGGTTTATATCTAT    60
AGTCCCGAGTATGTCAGTATGTGTGACTCCCTGGCCAAGATCCCCAAACGGGCCAGTATG   120
GTGCATTCTTTGATTGAAGCATATGCACTGCATAAGCAGATGAGGATAGTTAAGCCTAAA   180
GTGGCCTCCATGGAGGAGATGGCCGCCTTCCACACTGATGCTTATCTGCAGCATCTCCAG   240
AAGGTCAGCCAAGAGGGCGATGATGATCATCCGGACTCCATAGAATATGGGCTAGGTTAT   300
GACTGCCCAGCCACTGAAGGGATATTTGACTATGCAGCAGCTATAGGAGGGGCTACATC    360
ACAGCTGCCCAATGCCTGATTGACGGAATGTGCAAAGTAGCAATTAACTGGTCTGGAGGG   420
TGGCATCATGCAAAGAAAGATGAAGCATCTGGTTTTTGTTATCTCAATGATGCTGTCCTG   480
GGAATATTACGATTGCGACGGAAATTTGAGCGTATTCTCTACGTGGATTTGGATCTGCAC   540
CATGGAGATGGTGTAGAAGACGCATTCAGTTTCACCTCCAAAGTCATGACCGTGTCCCTG   600
CACAAATTCTCCCCAGGATTTTTCCCAGGAACAGGTGACGTGTCTGATGTTGGCCTAGGG   660
AAGGGACGGTACTACAGTGTAAATGTGCCCATTCAGGATGGCATACAAGATGAAAAATAT   720
TACCAGATCTGTGAAAGCGTACTAAAGGAAGTATACCAAGCCTTTAATCCCAAAGCAGTG   780
GTCTTACAGCTGGGAGCTGACACAATAGCTGGGGATCCCATGTGCTCCTTTAACATGACT   840
CCAGTGGGAATTGGCAAGTGTCTTAAGTACATCCTTCAATGGCAGTTGGCAACACTCATT   900
TTGGGAGGAGGAGGCTATAACCTTGCCAACACGGCTCGATGCTGGACATACTTGACCGGG   960
GTCATCCTAGGGAAAACACTATCCTCTGAGATCCCAGATCATGAGTTTTTCACAGCATAT  1020
GGTCCTGATTATGTGCTGGAAATCACGCCAAGCTGCCGGCCAGACCGCAATGAGCCCCAC  1080
CGAATCCAACAAATCCTCAACTACATCAAAGGGAATCTGAAGCATGTGGTCTAG        1134
```

FIGURE 4

Amino acid sequence for residues 1-377 of HDAC8 with a cleavable
N-terminal 6x-histidine tag [SEQ ID NO:3]
(6x-histidine tag underlined)

```
MHHHHHHPMEEPEEPADSGQSLVPVYIYSPEYVSMCDSLAKIPKRASMVHSLIEAYALHK   60
QMRIVKPVASMEEMAAFHTDAYLQHLQKVSQEGDDDHPDSIEYGLGYDCPATEGIFDYA   120
AAIGGATITAAQCLIDGMCKVAINWSGGWHHAKKDEASGFCYLNDAVLGILRLRRKFERI  180
LYVDLDLHHGDGVEDAFSFTSKVMTVSLHKFSPGFFPGTGDVSDVGLGKGRYYSVNVPIQ  240
DGIQDEKYYQICESVLKEVYQAFNPKAVVLQLGADTIAGDPMCSFNMTPVGIGKCLKYIL  300
QWQLATLILGGGGYNLANTARCWTYLTGVILGKTLSSEIPDHEFFTAYGPDYVLEITPSC  360
RPDRNEPHRIQQILNYIKGNLKHVV                                     385
```

Figure 5A

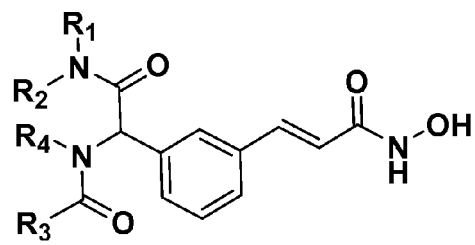

| R1 | R2 | R3 | R4 | < 5 µM Activity |
|---|---|---|---|---|
| PhCH₂ | H | H | CH₃ | |
| PhCH₂ | H | CH₃ | CH₃ | |
| PhCH₂ | H | n-Propyl | CH₃ | |
| PhCH₂ | H | c-Hexyl | CH₃ | |
| PhCH₂ | H | MeO(CH₂)- | CH₃ | |
| PhCH₂ | H | Me(CH=CH)₂- | CH₃ | |
| PhCH₂ | H | Ph | CH₃ | Yes |
| PhCH₂ | H | o-MePh | CH₃ | |
| PhCH₂ | H | m-MePh | CH₃ | |
| PhCH₂ | H | p-MePh | CH₃ | |
| PhCH₂ | H | o-CF₃Ph | CH₃ | |
| PhCH₂ | H | m-CF₃Ph | CH₃ | |
| PhCH₂ | H | p-CF₃Ph | CH₃ | |
| PhCH₂ | H | o-MeOPh | CH₃ | |
| PhCH₂ | H | m-MeOPh | CH₃ | |
| PhCH₂ | H | p-MeOPh | CH₃ | |
| PhCH₂ | H | o-BrPh | CH₃ | |
| PhCH₂ | H | m-BrPh | CH₃ | Yes |
| PhCH₂ | H | p-BrPh | CH₃ | |
| PhCH₂ | H | o-HOPh | CH₃ | |
| PhCH₂ | H | m-HOPh | CH₃ | |
| PhCH₂ | H | p-HOPh | CH₃ | |
| PhCH₂ | H | o-PhOPh | CH₃ | |
| PhCH₂ | H | m-PhOPh | CH₃ | Yes |
| PhCH₂ | H | p-PhOPh | CH₃ | Yes |
| PhCH₂ | H | m-Me₂NPh | CH₃ | |
| PhCH₂ | H | p-Me₂NPh | CH₃ | |
| PhCH₂ | H | m-NCPh | CH₃ | Yes |
| PhCH₂ | H | p-NCPh | CH₃ | |
| PhCH₂ | H | 1-Naphthyl | CH₃ | Yes |
| PhCH₂ | H | 1-Naphthylmethyl | CH₃ | Yes |

Figure 5A (cont.)

| R1 | R2 | R3 | R4 | < 5 μM Activity |
|---|---|---|---|---|
| PhCH$_2$ | H | 2-Naphthyl | CH$_3$ | Yes |
| PhCH$_2$ | H | p-PhPh | CH$_3$ | Yes |
| PhCH$_2$ | H | m-NO$_2$PhCH=CH- | CH$_3$ | |
| PhCH$_2$ | H | PhCH$_2$CH$_2$- | CH$_3$ | Yes |
| PhCH$_2$ | H | PhCH$_2$ | CH$_3$ | Yes |
| PhCH$_2$ | H | Ac-D-Pro | CH$_3$ | |
| PhCH$_2$ | H | Ac-L-Pro | CH$_3$ | |
| PhCH$_2$ | H | Ac-D-Phe | CH$_3$ | |
| PhCH$_2$ | H | Ac-L-Phe | CH$_3$ | |
| PhCH$_2$ | H | Ac-D-Try | CH$_3$ | |
| PhCH$_2$ | H | Ac-L-Try | CH$_3$ | |
| PhCH$_2$ | H | 2-furyl | CH$_3$ | |
| PhCH$_2$ | H | 3-furyl | CH$_3$ | |
| PhCH$_2$ | H | furylCH=CH- | CH$_3$ | |
| PhCH$_2$ | H | 2-benzofuranyl | CH$_3$ | Yes |
| PhCH$_2$ | H | 1-methyl-2-pyrrolyl | CH$_3$ | |
| PhCH$_2$ | H | 4-(1H-pyrrol-1-yl)Ph | CH$_3$ | |
| PhCH$_2$ | H | 2-hydroxy-5-(1H-pyrrol-1-yl) | CH$_3$ | |
| PhCH$_2$ | H | 2,6-dimethoxypyridyl | CH$_3$ | |
| PhCH$_2$ | H | 4-pyridyl | CH$_3$ | |
| PhCH$_2$ | H | 3-pyridyl | CH$_3$ | |
| PhCH$_2$ | H | α-hydroxymethyl | CH$_3$ | |
| PhCH$_2$ | H | 2-quinolinyl | CH$_3$ | Yes |
| PhCH$_2$ | H | 5-methoxy-2-indolyl | CH$_3$ | |
| PhCH$_2$ | H | MeO$_2$C(CH$_2$)$_6$- | CH$_3$ | Yes |
| PhCH$_2$ | H | 4-nitro-3-pyrazolyl | CH$_3$ | |
| PhCH$_2$ | H | 4-imidazolyl-CH=CH- | CH$_3$ | |
| PhCH$_2$ | H | (2-pyrimidylthio)CH$_2$ | CH$_3$ | |
| PhCH$_2$ | H | 5-methyl-3-pyrazolyl | CH$_3$ | |
| PhCH$_2$ | H | 3-hydroxy-2-quinoxalinyl | CH$_3$ | |
| PhCH$_2$ | H | 2-pyrazinyl | CH$_3$ | |
| PhCH$_2$ | H | H | CH$_3$ | |
| PhCH$_2$ | H | H | Isopropyl | Yes |
| PhCH$_2$ | H | H | Ethyl | |

Figure 5A (cont.)

| R1 | R2 | R3 | R4 | < 5 µM Activity |
|---|---|---|---|---|
| PhCH$_2$ | H | H | 3-Phenyl-1-propyl | |
| PhCH$_2$ | H | H | Cyclopentyl | Yes |
| PhCH$_2$ | H | H | Isoamyl | Yes |
| PhCH$_2$ | H | H | R-(+)-a-methylbenzyl | Yes |
| PhCH$_2$ | H | H | S-(+)-a-methylbenzyl | Yes |
| PhCH$_2$ | H | H | 4-Methoxybenzyl | |
| PhCH$_2$ | H | H | 3-Methoxybenzyl | |
| PhCH$_2$ | H | H | 4-Aminobenzyl | |
| PhCH$_2$ | H | H | 2-BenzylPh | |
| PhCH$_2$ | H | H | p-MePh | |
| PhCH$_2$ | H | H | 4-PhenoxyPh | Yes |
| PhCH$_2$ | H | H | 3-PhenoxyPh | Yes |
| PhCH$_2$ | H | H | 3-Phenylbenzyl | Yes |
| PhCH$_2$ | H | H | 2-Phenylbenzyl | Yes |
| PhCH$_2$ | H | H | 3-NCPh | |
| PhCH$_2$ | H | H | 4-NCPh | |
| PhCH$_2$ | H | H | 2-pyridyl | |
| PhCH$_2$ | H | H | 3-pyridyl | |
| PhCH$_2$ | H | H | 4-pyridyl | |
| PhCH$_2$ | H | H | 2,2-Diphenylethyl | |
| PhCH$_2$ | H | H | 4-PhenylPh | Yes |
| PhCH$_2$ | H | H | 1-Naphthyl | Yes |
| PhCH$_2$ | H | H | 1-Naphthalene-methyl | Yes |
| PhCH$_2$ | H | H | 2-MeO-5-PhenylPh | |
| PhCH$_2$ | H | H | m-MeOPh | |
| PhCH$_2$ | H | H | p-MeOPh | |
| PhCH$_2$ | H | H | 1-indanyl | |
| PhCH$_2$ | H | H | 2-N-Phenylamino-Ph | |
| PhCH$_2$ | H | H | 4-N-Phenylamino-Ph | |
| PhCH$_2$ | H | H | 3-pyridylmethyl | |
| PhCH$_2$ | H | H | 4-pyridylmethyl | |

Figure 5A (cont.)

| R1 | R2 | R3 | R4 | < 5 µM Activity |
|---|---|---|---|---|
| PhCH$_2$ | H | H | 3,4-DiMeO-phenethyl | |
| PhCH$_2$ | H | H | Phenethyl | Yes |
| PhCH$_2$ | H | H | 3-pyrazolyl | |
| PhCH$_2$ | H | H | Ph | Yes |
| PhCH$_2$ | H | H | 3-Benzyloxy-Ph | |
| PhCH$_2$ | H | H | 4-Benzyloxy-Ph | |
| PhCH$_2$ | H | H | 2-Aminobenzanilide | |
| PhCH$_2$ | H | H | 3-Nitrobenzyl | |
| PhCH$_2$ | H | H | 4-Nitrobenzyl | |
| PhCH$_2$ | H | H | m-Nitro-Ph | |
| PhCH$_2$ | H | H | p-Nitro-Ph | |
| PhCH$_2$ | H | H | 3-Chlorobenzyl | |
| PhCH$_2$ | H | H | 4-Chlorobenzyl | |
| PhCH$_2$ | H | H | 2-Chloro-Ph | |
| PhCH$_2$ | H | H | 3-Chloro-Ph | |
| PhCH$_2$ | H | H | 4-Chloro-Ph | |
| PhCH$_2$ | H | H | L-Phenylalaninol | |
| PhCH$_2$ | H | H | D-Phenylalaninol | |
| PhCH$_2$ | H | H | 3-(2-ethyl)indolyl | |
| PhCH$_2$ | H | H | p-HO-PhCH$_2$CH$_2$- | |
| PhCH$_2$ | H | H | 2-(1-pyrrolidyl)ethyl | |
| PhCH$_2$ | H | H | Cyclohexyl | |

Figure 5B

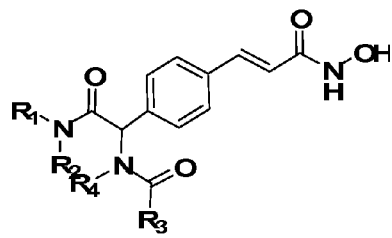

| R1 | R2 | R3 | R4 | < 5 μM Activity |
|---|---|---|---|---|
| PhCH$_2$ | H | H | CH$_3$ | Yes |
| PhCH$_2$ | H | CH$_3$ | CH$_3$ | |
| PhCH$_2$ | H | n-Propyl | CH$_3$ | Yes |
| PhCH$_2$ | H | c-Hexyl | CH$_3$ | Yes |
| PhCH$_2$ | H | MeO(CH$_2$)$_2$- | CH$_3$ | Yes |
| PhCH$_2$ | H | Me(CH=CH)$_2$- | CH$_3$ | Yes |
| PhCH$_2$ | H | Ph | CH$_3$ | Yes |
| PhCH$_2$ | H | o-McPh | CH$_3$ | Yes |
| PhCH$_2$ | H | m-McPh | CH$_3$ | Yes |
| PhCH$_2$ | H | p-McPh | CH$_3$ | |
| PhCH$_2$ | H | o-CF$_3$Ph | CH$_3$ | Yes |
| PhCH$_2$ | H | m-CF$_3$Ph | CH$_3$ | Yes |
| PhCH$_2$ | H | p-CF$_3$Ph | CH$_3$ | Yes |
| PhCH$_2$ | H | o-MeOPh | CH$_3$ | Yes |
| PhCH$_2$ | H | m-MeOPh | CH$_3$ | Yes |
| PhCH$_2$ | H | p-MeOPh | CH$_3$ | Yes |
| PhCH$_2$ | H | o-BrPh | CH$_3$ | Yes |
| PhCH$_2$ | H | m-BrPh | CH$_3$ | Yes |
| PhCH$_2$ | H | p-BrPh | CH$_3$ | Yes |
| PhCH$_2$ | H | o-HOPh | CH$_3$ | Yes |
| PhCH$_2$ | H | m-HOPh | CH$_3$ | Yes |
| PhCH$_2$ | H | p-HOPh | CH$_3$ | Yes |
| PhCH$_2$ | H | o-PhOPh | CH$_3$ | Yes |
| PhCH$_2$ | H | m-PhOPh | CH$_3$ | |
| PhCH$_2$ | H | p-PhOPh | CH$_3$ | |
| PhCH$_2$ | H | m-Me$_2$NPh | CH$_3$ | |

Figure 5B (cont.)

| R1 | R2 | R3 | R4 | < 5 μM Activity |
|---|---|---|---|---|
| PhCH₂ | H | p-Me₂NPh | CH₃ | |
| PhCH₂ | H | m-NCPh | CH₃ | Yes |
| PhCH₂ | H | p-NCPh | CH₃ | Yes |
| PhCH₂ | H | 1-Naphthyl | CH₃ | Yes |
| PhCH₂ | H | 2-Naphthyl | CH₃ | Yes |
| PhCH₂ | H | p-PhPh | CH₃ | |
| PhCH₂ | H | m-NO₂PhCH=CH- | CH₃ | Yes |
| PhCH₂ | H | PhCH₂CH₂- | CH₃ | Yes |
| PhCH₂ | H | PhCH₂ | CH₃ | Yes |
| PhCH₂ | H | Ac-D-Pro | CH₃ | Yes |
| PhCH₂ | H | Ac-L-Pro | CH₃ | Yes |
| PhCH₂ | H | Ac-D-Phe | CH₃ | Yes |
| PhCH₂ | H | Ac-L-Phe | CH₃ | Yes |
| PhCH₂ | H | Ac-D-Try | CH₃ | |
| PhCH₂ | H | Ac-L-Try | CH₃ | |
| PhCH₂ | H | 2-furyl | CH₃ | |
| PhCH₂ | H | 3-furyl | CH₃ | |
| PhCH₂ | H | furylCH=CH- | CH₃ | |
| PhCH₂ | H | 2-benzofuranyl | CH₃ | |
| PhCH₂ | H | 1-methyl-2-pyrrolyl | CH₃ | |
| PhCH₂ | H | 4-(1H-pyrrol-1-yl)Ph | CH₃ | |
| PhCH₂ | H | 2-hydroxy-5-(1H-pyrrol-1-yl) | CH₃ | |
| PhCH₂ | H | 2,6-dimethoxypyridyl | CH₃ | |
| PhCH₂ | H | 4-pyridyl | CH₃ | |
| PhCH₂ | H | 3-pyridyl | CH₃ | |
| PhCH₂ | H | α-hydroxymethyl | CH₃ | |
| PhCH₂ | H | 2-quinolinyl | CH₃ | |
| PhCH₂ | H | 5-methoxy-2-indolyl | CH₃ | |
| PhCH₂ | H | HO₂C(CH₂)₆- | CH₃ | |
| PhCH₂ | H | 4-nitro-3-pyrazolyl | CH₃ | |
| PhCH₂ | H | 4-imidazolyl-CH=CH- | CH₃ | |
| PhCH₂ | H | (2-pyrimidylthio)CH₂ | CH₃ | |
| PhCH₂ | H | 5-methyl-3-pyrazolyl | CH₃ | |
| PhCH₂ | H | 3-hydroxy-2-quinoxalinyl | CH₃ | |

Figure 5B (cont.)

| R1 | R2 | R3 | R4 | < 5 μM Activity |
|---|---|---|---|---|
| PhCH₂ | H | 2-pyrazinyl | CH₃ | |
| PhCH₂ | H | H | CH₃ | |
| PhCH₂ | H | H | Isopropyl | Yes |
| PhCH₂ | H | H | Ethyl | |
| PhCH₂ | H | H | 3-Phenyl-1-propyl | Yes |
| PhCH₂ | H | H | Cyclopentyl | Yes |
| PhCH₂ | H | H | Isoamylamine | |
| PhCH₂ | H | H | R-(+)-a-methylbenzyl | Yes |
| PhCH₂ | H | H | S-(+)-a-methylbenzyl | Yes |
| PhCH₂ | H | H | 4-Methoxybenzyl | Yes |
| PhCH₂ | H | H | 3-Methoxybenzyl | Yes |
| PhCH₂ | H | H | 4-Aminobenzyl | Yes |
| PhCH₂ | H | H | 2-BenzylPh | Yes |
| PhCH₂ | H | H | p-MePh | Yes |
| PhCH₂ | H | H | 4-PhenoxyPh | Yes |
| PhCH₂ | H | H | 3-PhenoxyPh | |
| PhCH₂ | H | H | 3-Phenylbenzyl | Yes |
| PhCH₂ | H | H | 2-Phenylbenzyl | Yes |
| PhCH₂ | H | H | 3-NCPh | Yes |
| PhCH₂ | H | H | 4-NCPh | Yes |
| PhCH₂ | H | H | 2-pyridyl | |
| PhCH₂ | H | H | 3-pyridyl | |
| PhCH₂ | H | H | 4-pyridyl | |
| PhCH₂ | H | H | 2,2-Diphenylethyl | Yes |
| PhCH₂ | H | H | 4-PhenylPh | |
| PhCH₂ | H | H | 1-Naphthyl | Yes |
| PhCH₂ | H | H | 1-Naphthalene-methyl | Yes |
| PhCH₂ | H | H | 2-MeO-5-PhenylPh | |
| PhCH₂ | H | H | m-MeOPh | Yes |
| PhCH₂ | H | H | p-McOPh | Yes |
| PhCH₂ | H | H | 1-indanyl | |
| PhCH₂ | H | H | 2-N-Phenylamino-Ph | Yes |
| PhCH₂ | H | H | 4-N-Phenylamino-Ph | |
| PhCH₂ | H | H | 3-pyridylmethyl | |

Figure 5B (cont.)

| R1 | R2 | R3 | R4 | < 5 µM Activity |
|---|---|---|---|---|
| PhCH$_2$ | H | H | 4-pyridylmethyl | |
| PhCH$_2$ | H | H | 3,4-DiMeO-phenethyl | Yes |
| PhCH$_2$ | H | H | Phenethyl | Yes |
| PhCH$_2$ | H | H | 3-pyrazolyl | |
| PhCH$_2$ | H | H | Ph | Yes |
| PhCH$_2$ | H | H | 3-Benzyloxy-Ph | Yes |
| PhCH$_2$ | H | H | 4-Benzyloxy-Ph | Yes |
| PhCH$_2$ | H | H | 2-Aminobenzanilide | |
| PhCH$_2$ | H | H | 3-Nitrobenzyl | Yes |
| PhCH$_2$ | H | H | 4-Nitrobenzyl | Yes |
| PhCH$_2$ | H | H | m-Nitro-Ph | |
| PhCH$_2$ | H | H | p-Nitro-Ph | Yes |
| PhCH$_2$ | H | H | 3-Chlorobenzyl | |
| PhCH$_2$ | H | H | 4-Chlorobenzyl | Yes |
| PhCH$_2$ | H | H | 2-Chloro-Ph | Yes |
| PhCH$_2$ | H | H | 3-Chloro-Ph | Yes |
| PhCH$_2$ | H | H | 4-Chloro-Ph | Yes |
| PhCH$_2$ | H | H | L-Phenylalaninol | |
| PhCH$_2$ | H | H | D-Phenylalaninol | |
| PhCH$_2$ | H | H | 3-(2-ethyl)indolyl | Yes |
| PhCH$_2$ | H | H | p-HO-PhCH$_2$CH$_2$- | |
| PhCH$_2$ | H | H | 2-(1-pyrrolidyl)ethyl | |
| PhCH$_2$ | H | H | Cyclohexyl | Yes |

HISTONE DEACETYLASE INHIBITORS

RELATED APPLICATION

This application is a continuation of patent application Ser. No. 10/681,049, filed Oct. 7, 2003, now issued as U. S. Pat. No. 7,154,002, which claims the benefit of U.S. Provisional Application No. 60/417,238, filed Oct. 8, 2002, which is incorporated herein by reference in its entirety.

FIELD OF THE INVENTION

The invention relates to compounds that may be used to inhibit histone deacetylases (HDAC) as well as compositions of matter and kits comprising these compounds. The present invention also relates to methods for inhibiting HDAC as well as treatment methods using compounds according to the present invention.

DESCRIPTION OF RELATED ART

DNA in eukaryotic cells is tightly complexed with proteins (histones) to form chromatin. Histones are small, positively charged proteins that are rich in basic amino acids (positively charged at physiological pH), which contact the phosphate groups (negatively charged at physiological pH) of DNA. There are five main classes of histones H1, H2A, H2B, H3, and H4. The amino acid sequences of H2A, H2B, H3, and H4 show remarkable conservation between species, wherein H1 varies somewhat and in some cases is replaced by another histone, e.g., H5. Four pairs of each of H2A, H2B, H3 and H4 together form a disk-shaped octomeric protein core, around which DNA (about 140 base pairs) is wound to form a nucleosome. Individual nucleosomes are connected by short stretches of linker DNA associated with another histone molecule to form a structure resembling a beaded string, which is itself arranged in a helical stack, known as a solenoid.

The majority of histones are synthesized during the S phase of the cell cycle, and newly synthesized histones quickly enter the nucleus to become associated with DNA. Within minutes of its synthesis, new DNA becomes associated with histones in nucleosomal structures.

A small fraction of histones, more specifically, the amino acid side chains thereof, are enzymatically modified by post-translational addition of methyl, acetyl, or phosphate groups, neutralizing the positive charge of the side chain, or converting it to a negative charge. For example, lysine and arginine groups may be methylated, lysine groups may be acetylated, and serine groups may be phosphorylated. For lysine, the —$(CH_2)_4$—$NH_2$ sidechain may be acetylated, for example by an acetyltransferase enzyme to give the amide —$(CH_2)_4$—NHC(=O)$CH_3$. Methylation, acetylation, and phosphorylation of amino termini of histones that extend from the nucleosomal core affects chromatin structure and gene expression. Spencer and Davie 1999. Gene 240:1 1-12.

Acetylation and deacetylation of histones is associated with transcriptional events leading to cell proliferation and/or differentiation. Regulation of the function of transcriptional factors is also mediated through acetylation. Recent reviews on histone deacetylation include Kouzarides, et al., 1999. Curr. Opin. Genet. Dev. 9:1, 40-48 and Pazin, et al. 1997. 89:3 325-328.

The correlation between acetylation status of histones and the transcription of genes has been known for quite some time. Certain enzymes, specifically acetylases (e.g., histone acetyltransferases (HAT) and deacetylases (histone deacetylase or HDAC), which regulate the acetylation state of histones have been identified in many organisms and have been implicated in the regulation of numerous genes, confirming a link between acetylation and transcription. In general, histone acetylation is believed to correlation with transcriptional activation, whereas histone deacetylation is believed to be associated with gene repression.

A growing number of histone deacetylases (HDACs) have been identified. HDACs function as part of large multiprotein complexes, which are tethered to the promoter and repress transcription. Well characterized transcriptional repressors such as MAD, nuclear receptors and YY1 associate with HDAC complexes to exert their repressor function.

Studies of HDAC inhibitors have shown that these enzymes play an important role in cell proliferation and differentiation. HDACs are believed to be associated with a variety of different disease states including, but not limited to cell proliferative diseases and conditions (Marks, P. A., Richon, V. M., Breslow, R. and Rifkind, R. A., J. Natl. Cancer Inst. (Bethesda) 92, 1210-1215, 2000) such as leukemia (Lin et al. 1998. Nature 391: 811-814; Grignani, et al. 1998. Nature 391: 815-818; Warrell et al. 1998. J. Natl. Cancer Inst. 90:1621-1625; Gelmetti et al. 1998. Mol. Cell. Biol. 18:7185-7191; Wang et al. 1998. PNAS 951 0860-10865), melanomas/squamous cell carcinomas (Gillenwater, et al., 1998, Int. J. Cancer 75217-224; Saunders, et al., 1999, Cancer Res. 59:399-404), breast cancer, prostrate cancer, bladder cancer (Gelmetti et al. 1998. Mol. Cell. Biol. 18:7185-7191; Wang et al. 1998. PNAS 951 0860-10865), lung cancer, ovarian cancer and colon cancer (Hassig, et al., 1997, Chem. Biol. 4:783-789; Archer, et al., 1998, PNAS, 956791-6796; Swendeman, et al., 1999, Proc. Amer. Assoc. Cancer Res. 40, Abstract #3836).

Histone deacetylase inhibitors are potent inducers of growth arrest, differentiation, or apoptotic cell death in a variety of transformed cells in culture and in tumor bearing animals (*Histone deacetylase inhibitors as new cancer drugs*, Marks, P. A., Richon, V. M., Breslow, R. and Rifkind, R. A., Current Opinions in Oncology, 2001, Nov. 13 (6): 477-83; *Histone deacetylases and cancer: causes and therapies*, Marks, P., Rifkind, R. A., Richon, V. M., Breslow, R., Miller, T. and Kelly, W. K., Nat. Rev. Cancer 2001 Dec. 1 (3): 194-202). In addition, HDAC inhibitors are useful in the treatment or prevention of protozoal diseases (U.S. Pat. No. 5,922,837) and psoriasis (PCT Publication No. WO 02/26696).

A variety of inhibitors of HDAC have been reported. Some of these inhibitors are described in the following table:

| Inhibitors | References |
|---|---|
| Butyrates | Marks PA, et al., J. Matl. Cancer Inst. 2000, 92:1210-1216; Weidle UH, et al., Anticancer Res. 2000, 20:1471-1486; Gore SD, et al., Exp. Opin. Invest. Drugs 2000, 9:2923-2934; Sowa Y, et al., Biofactors 2000, 12:283-287 |

-continued

| Inhibitors | References |
| --- | --- |
| Trichostatin A | Marks PA, et al., J. Natl. Cancer Inst. 2000, 92:1210-1216; Weidle UH, et al., Anticancer Res. 2000, 20:1471-1486; Nervi C, et al., Cancer Res. 2001, 61:1247-1249; Suzuki T, et al., Int. J. Cancer 2000, 88:992-997. |
| Suberoylanilidine hydroxamic acid | Marks PA, et al., J. Natl. Cancer Inst. 2000, 92:1210-1216; Kelly WK, et al., Proc. Amer. Soc. Clin. Oncol. 2001, 20:87a; Butler LM, et al., Cancer Res. 2000, 60:5165-5170. |
| MS-275 | Lee BI, et al., Cancer Res. 2001, 61:931-934. |

Additional examples of HDAC inhibitors can be found in Marks P A, et al., J. Natl. Cancer Inst. 2000, 92:1210-1216 & Weidle U H, et al., Anticancer Res. 2000, 20:1471-1486 and PCT Publication Nos. WO 02/26696, WO 02/062773, and WO 01/18171.

Despite the various HDAC inhibitors that have been reported to date, a need continues to exist for new and more effective inhibitors of HDACs.

SUMMARY OF THE INVENTION

The present invention relates to compounds that have activity for inhibiting HDACs. The present invention also provides compositions, articles of manufacture and kits comprising these compounds.

In one embodiment, a pharmaceutical composition is provided that comprises a HDAC inhibitor according to the present invention as an active ingredient. Pharmaceutical compositions according to the invention may optionally comprise 0.001%-100% of one or more HDAC inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with HDAC.

In one embodiment, a kit is provided that comprises a composition comprising at least one HDAC inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one HDAC inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit HDAC.

In one embodiment, the compounds, compositions, kits and articles of manufacture are used to treat a disease state for which HDAC possesses activity that contributes to the pathology and/or symptomology of the disease state.

In another embodiment, a compound is administered to a subject wherein HDAC activity within the subject is altered, preferably reduced.

In another embodiment, a prodrug of a compound is administered to a subject that is converted to the compound in vivo where it inhibits HDAC.

In another embodiment, a method of inhibiting HDAC is provided that comprises contacting HDAC with a compound according to the present invention.

In another embodiment, a method of inhibiting HDAC is provided that comprises causing a compound according to the present invention to be present in a subject in order to inhibit HDAC in vivo.

In another embodiment, a method of inhibiting HDAC is provided that comprises administering a first compound to a subject that is converted in vivo to a second compound wherein the second compound inhibits HDAC in vivo.

In another embodiment, a therapeutic method is provided that comprises administering a compound according to the present invention.

In another embodiment, a method of inhibiting cell proliferation is provided that comprises contacting a cell with an effective amount of a compound according to the present invention.

In another embodiment, a method of inhibiting cell proliferation in a patient is provided that comprises administering to the patient a therapeutically-effective amount of a compound according to the present invention.

In another embodiment, a method of treating a condition in a patient which is known to be mediated by HDAC, or which is known to be treated by HDAC inhibitors, comprising administering to the patient a therapeutically-effective amount of a compound according to the present invention.

In another embodiment, a method is provided for using a compound according to the present invention in order to manufacture a medicament for use in the treatment of disease state which is known to be mediated by HDAC, or which is known to be treated by HDAC inhibitors.

In another embodiment, a method is provided for treating a disease state for which HDAC possesses activity that contributes to the pathology and/or symptomology of the disease state, the method comprising: causing a compound according to the present invention to be present in a subject in a therapeutically effective amount for the disease state.

In another embodiment, a method is provided for treating a disease state for which HDAC possesses activity that contributes to the pathology and/or symptomology of the disease state, the method comprising: administering a first compound to a subject that is converted in vivo to a second compound such that the second compound is present in the subject in a therapeutically effective amount for the disease state.

In another embodiment, a method is provided for treating a disease state for which HDAC possesses activity that contributes to the pathology and/or symptomology of the disease state, the method comprising: administering a compound according to the present invention to a subject such that the compound is present in the subject in a therapeutically effective amount for the disease state.

In another embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of diseases that may be treated by administration of compounds and compositions according to the present invention include, but are not limited to protozoal diseases and cell proliferative diseases and conditions such as leukemia, melanomas, squamous cell carcinomas, breast cancer, prostrate cancer, bladder cancer, lung cancer, ovarian cancer and colon cancer.

It is noted in regard to all of the above embodiments that the present invention is intended to encompass pharmaceutically acceptable salts and solvates (e.g., hydrates) of the compounds, regardless of whether such salts and solvates are specified since it is well know in the art to administer pharmaceutical agents in a salt or solvated form. It is further noted that prodrugs may also be administered are altered in vivo and become a compound according to the present invention. The various methods of using the compounds of the present invention are intended, regardless of whether prodrug delivery is specified, to encompass the administration of a prodrug that is converted in vivo into a compound according to the present invention.

Figure 2A:
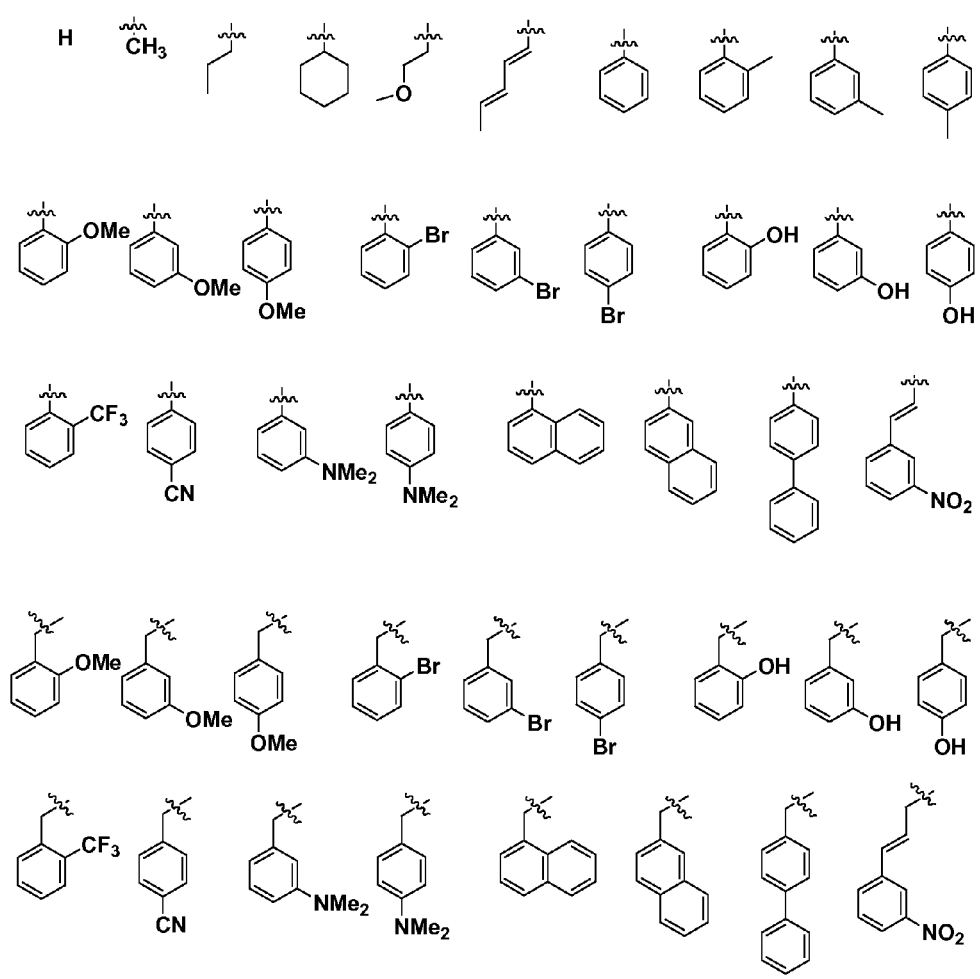
FIG. 2A illustrates particular examples of $R_1$, $R_2$ $R_3$ and $R_4$ substituents that may be employed.
Figure 2A:
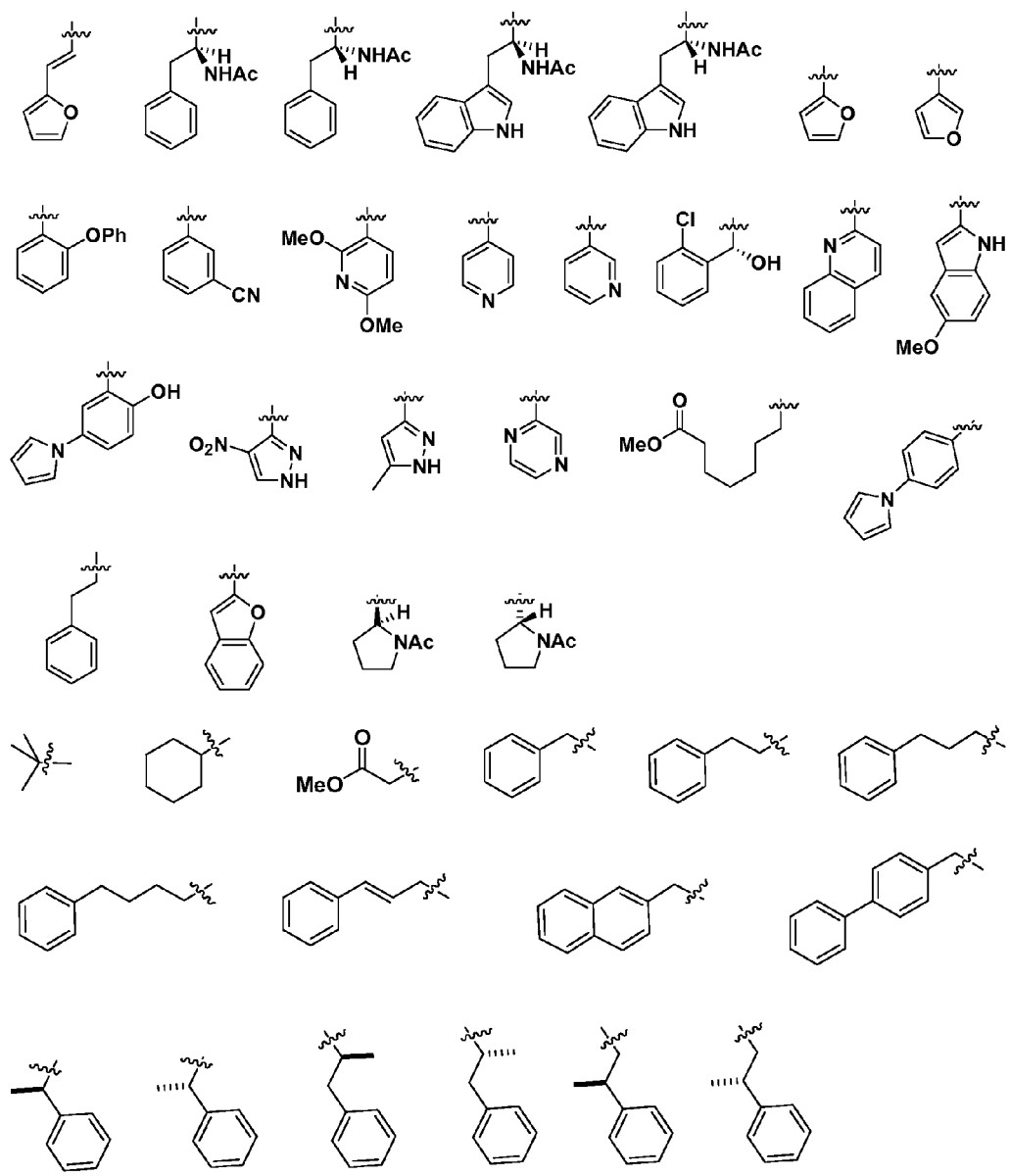
Figure 2A:
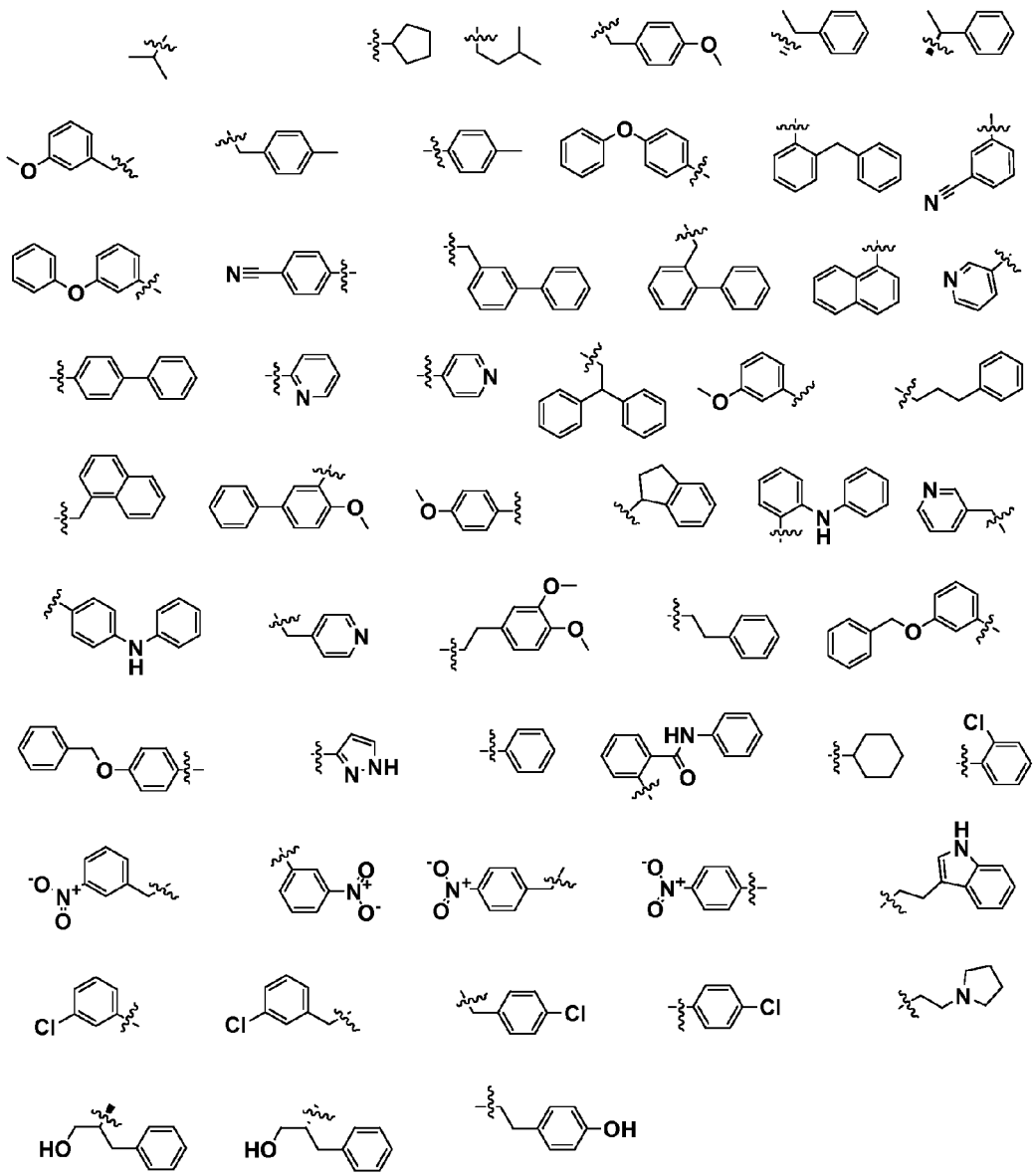
Figure 2B:
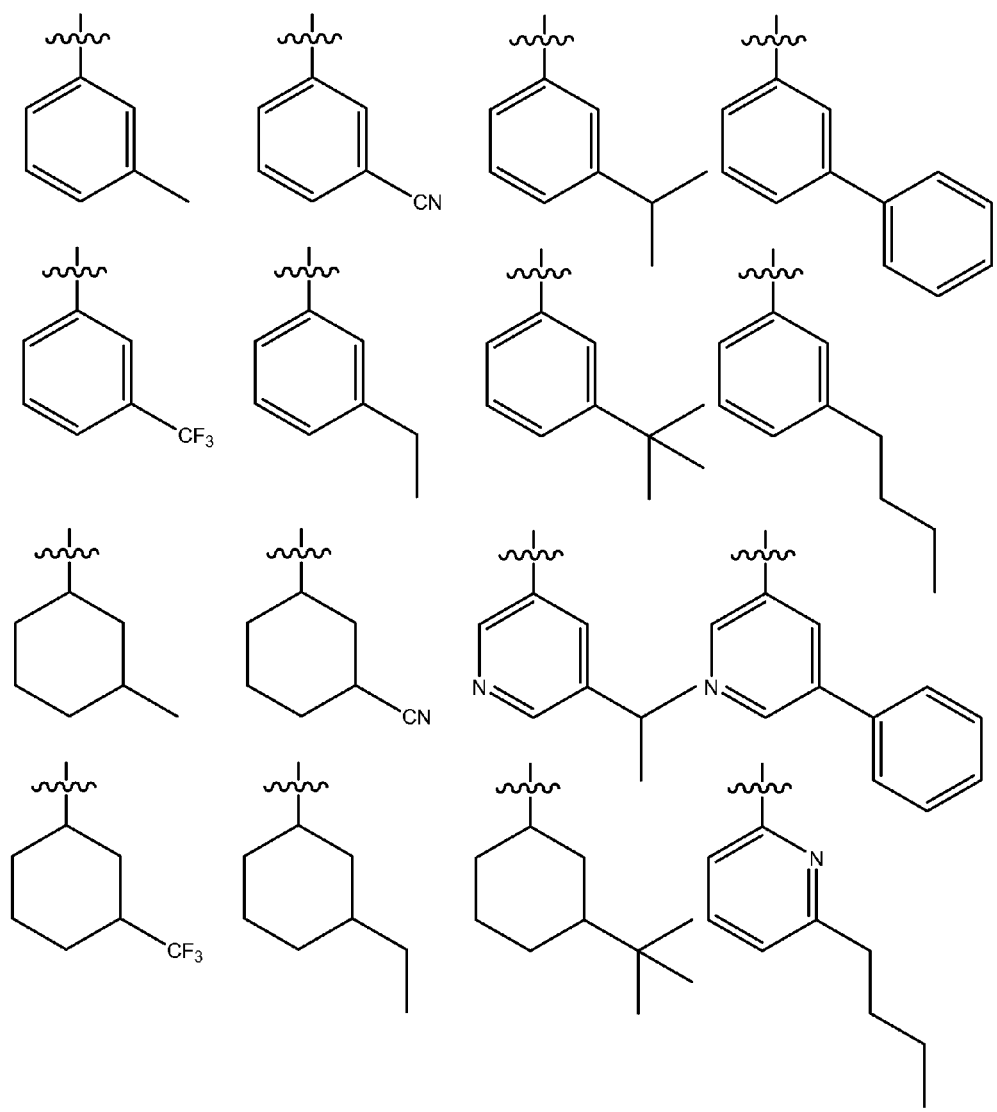
FIG. 2B illustrates particular examples of $R_3$ substituents that may be employed when $R_3$ comprises a five or six membered ring.
Figure 2B:
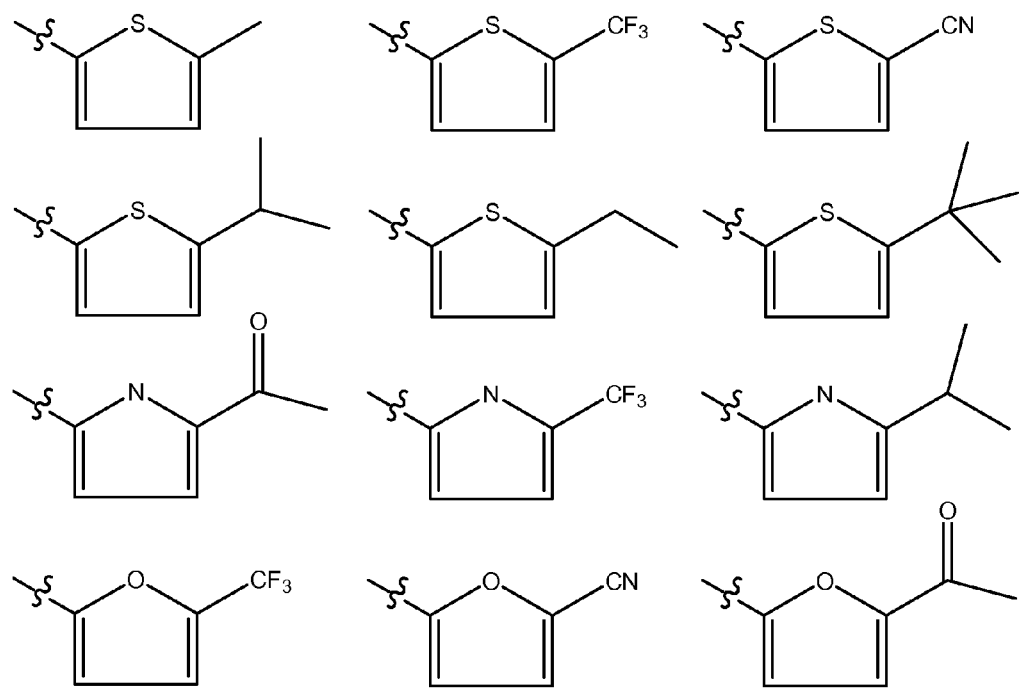
Figure 2B:
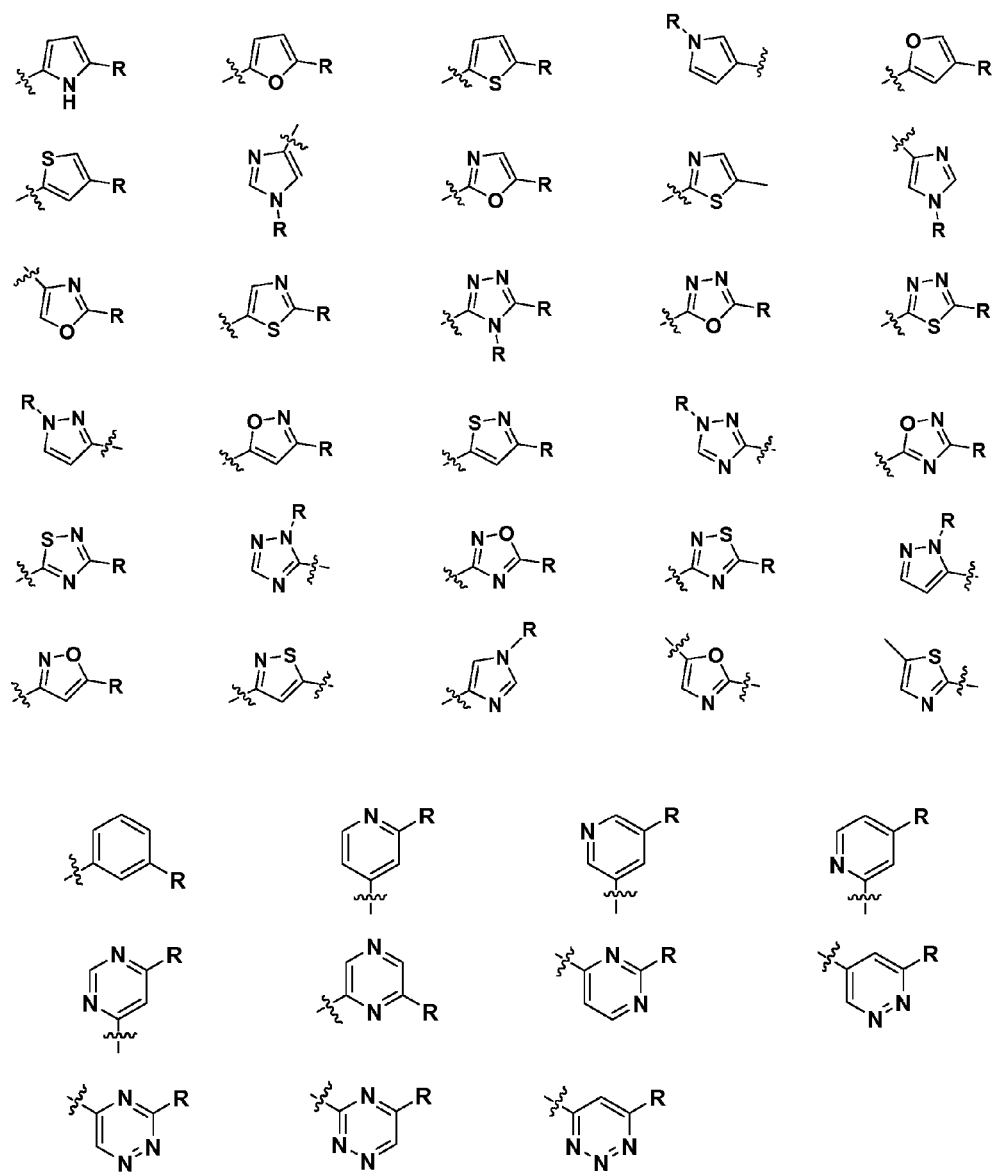
Figure 2C:
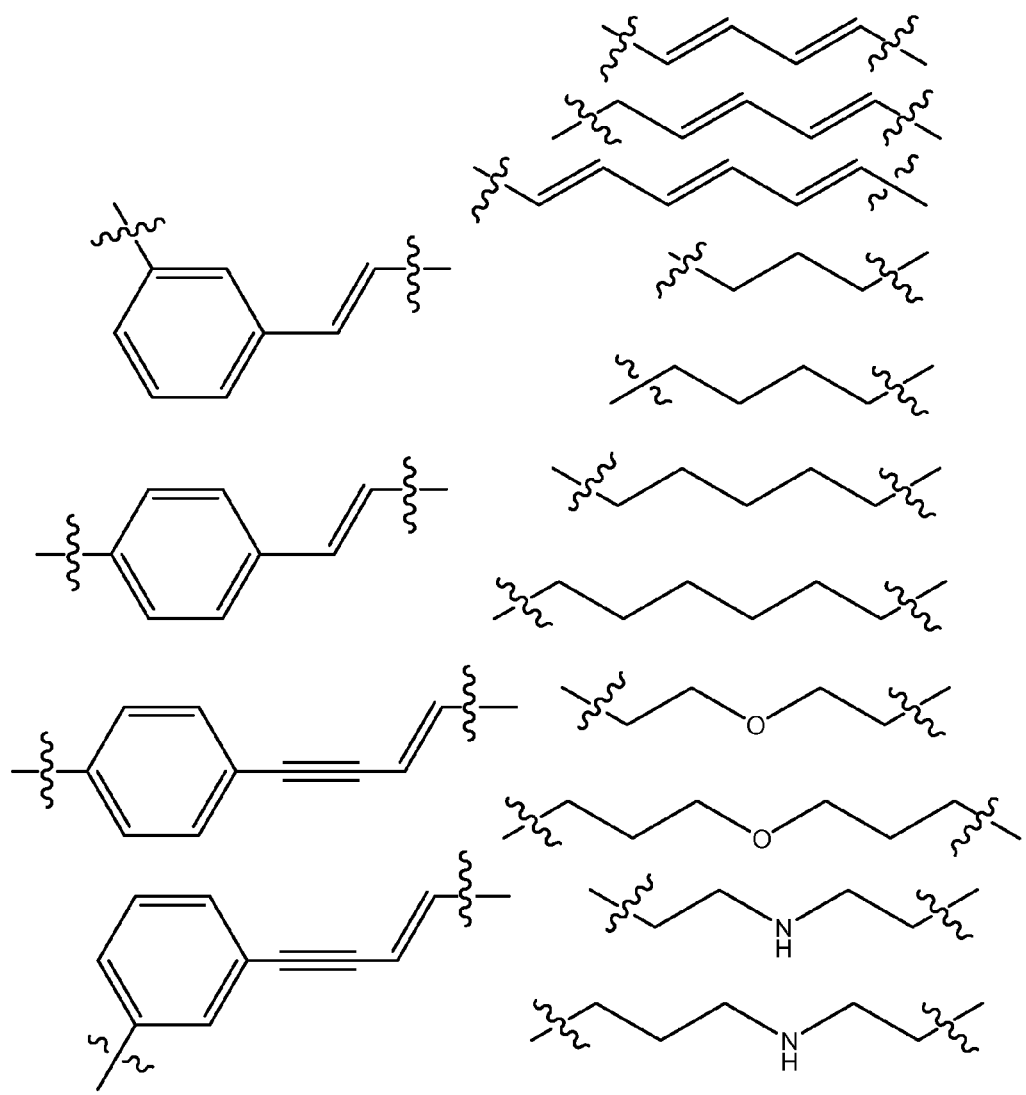
FIG. 2C illustrates particular examples of leader groups that may be used.
Figure 2C:
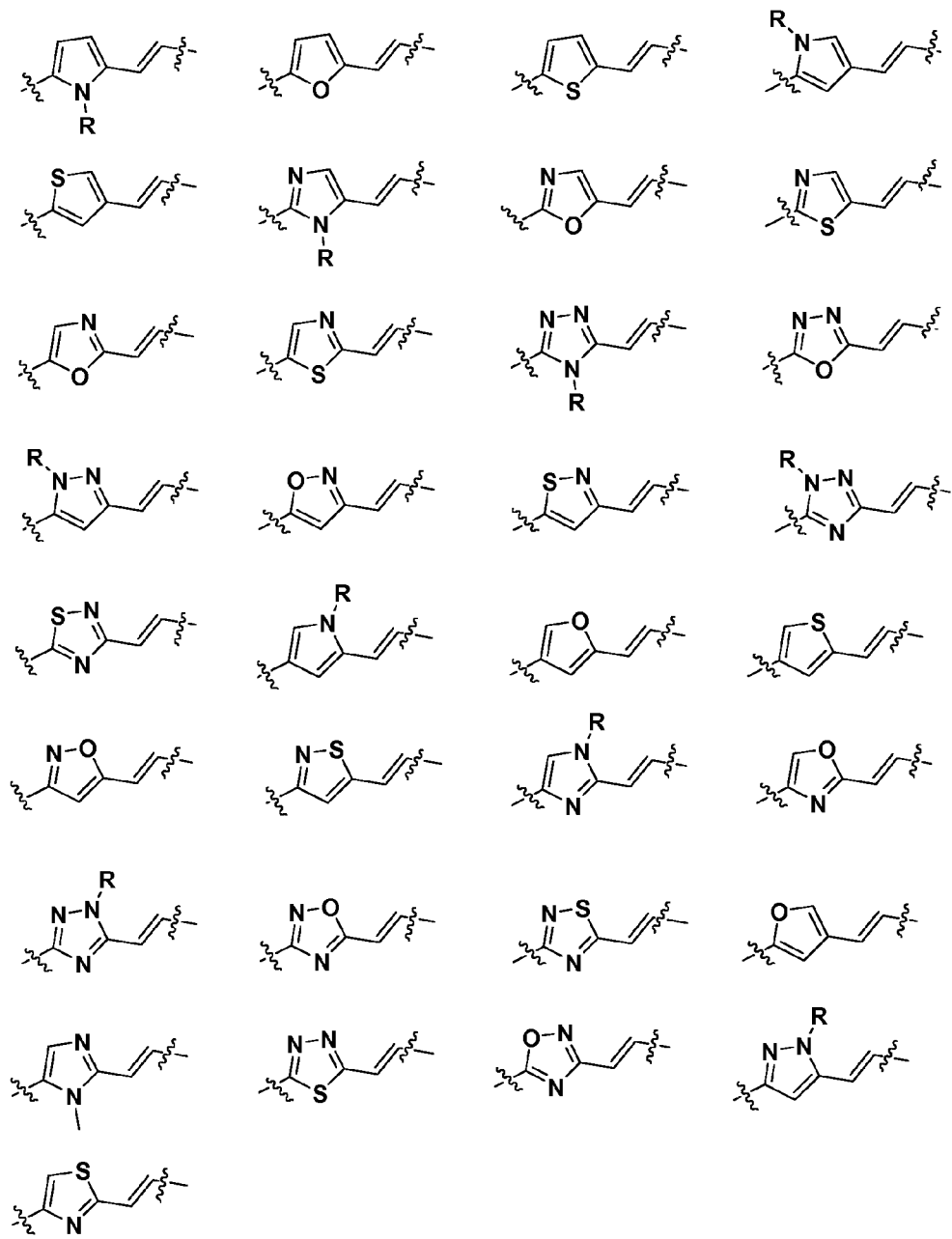
Figure 2C:
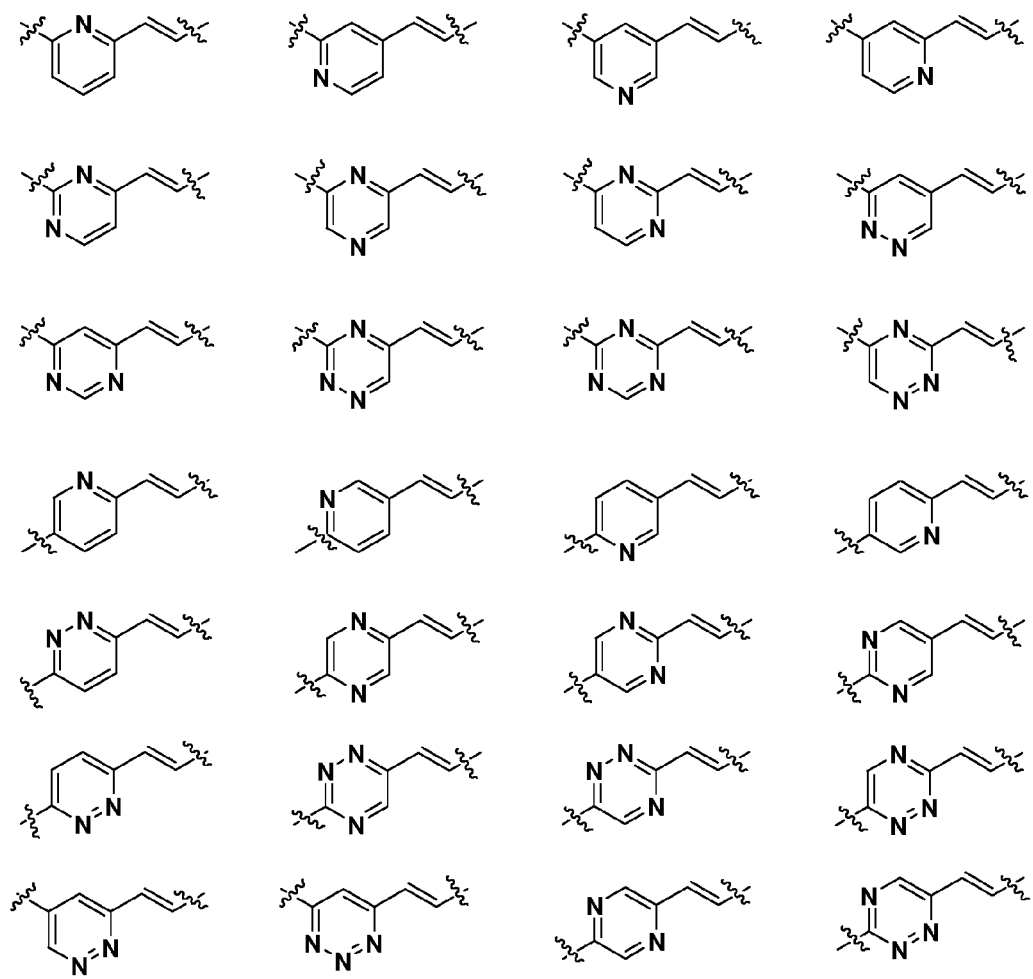

It is noted in regard to FIGS. 2A-2C that the squiggle line is intended to indicate a bond to an adjacent moiety. It is also noted that the substituents shown may optionally be further substituted beyond what is shown. Further, one or more heteroatoms may optionally be substituted for the carbon atoms shown. In regard to FIG. 2C, it is noted that the leader groups may be inserted into the inhibitors in either possible orientation.

FIG. 3 illustrates the DNA and amino acid sequence of HDAC8.

FIG. 4 illustrates the protein sequence shown in SEQ. ID No. 3.

FIG. 5A provides examples of compounds that were synthesized as described in example 2.

FIG. 5B provides examples of compounds that were synthesized as described in example 2.

DEFINITIONS

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulphur. Examples of alicyclic moieties include, but are not limited to moieties with C3-C8 rings such as cyclopropyl, cyclohexane, cyclopentane, cyclopentene, cyclopentadiene, cyclohexane, cyclohexene, cyclhexadiene, cycloheptane, cycloheptene, cycloheptadiene, cyclooctane, cyclooctene, and cyclooctadiene.

"Alkyl" represented by itself means a straight or branched, saturated or unsaturated, aliphatic radical having a chain of carbon atoms, optionally with oxygen (See "oxaalkyl") or nitrogen atoms (See "aminoalkyl") between the carbon atoms. $C_X$ alkyl and $C_{X-Y}$ alkyl are typically used where X and Y indicate the number of carbon atoms in the chain. For example, $C_{1-6}$ alkyl includes alkyls that have a chain of between 1 and 6 carbon (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means a bond (e.g., $(C_{6-10})$ aryl$(C_{0-3})$alkyl includes phenyl, benzyl, phenethyl, 1-phenylethyl 3-phenylpropyl, and the like).

"Alkylene", unless indicated otherwise, means a straight or branched, saturated or unsaturated, aliphatic, divalent radical. $C_X$ alkylene and $C_{X-Y}$ alkylene are typically used where X and Y indicate the number of carbon atoms in the chain. For example, $C_{1-6}$ alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like).

"Alkylidene" means a straight or branched saturated or unsaturated, aliphatic, divalent radical. $C_X$ alkylidene and $C_{X-Y}$ alkylidene are typically used where X and Y indicate the number of carbon atoms in the chain. For example, $C_{1-6}$ alkylidene includes methylene (=$CH_2$), ethylidene (=$CHCH_3$), isopropylidene (=$C(CH_3)_2$), propylidene (=$CHCH_2CH_3$), allylidene (=$CH^-CH=CH_2$), and the like).

"Amino" means a nitrogen moiety having two further substituents where a hydrogen or carbon atom is alpha to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aminoalkyl" means an alkyl, as defined above, except where one or more substituted or unsubstituted nitrogen atoms (—N—) are positioned between carbon atoms of the alkyl. For example, an $(C_{2-6})$ aminoalkyl refers to a chain comprising between 2 and 6 carbons and one or more nitrogen atoms positioned between the carbon atoms.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to 4n+2.

"Aryl" means a monocyclic or fused bicyclic ring assembly wherein each ring is comprised of 6 ring carbon atoms and is aromatic or when fused with a second ring forms an aromatic ring assembly. $C_X$ aryl and $C_{X-Y}$ aryl are typically used where X and Y indicate the number of carbon atoms in ring and directly attached to the ring. For example, optionally substituted $(C_{6-10})$aryl as used in this Application includes, but is not limited to, biphenyl-2-yl, 2-bromophenyl, 2-bromocarbonylphenyl, 2-bromo-5-fluorophenyl, 4-tert-butylphenyl, 4-carbamoylphenyl, 4-carboxy-2-nitrophenyl, 2-chlorophenyl, 4-chlorophenyl, 3-chlorocarbonylphenyl, 4-chlorocarbonylphenyl, 2-chloro-4-fluorophenyl, 2-chloro-6-fluorophenyl, 4-chloro-2-nitrophenyl, 6-chloro-2-nitrophenyl, 2,6-dibromophenyl, 2,3-dichlorophenyl, 2,5-dichlorophenyl, 3,4-dichlorophenyl, 2-difluoromethoxyphenyl, 3,5-dimethylphenyl, 2-ethoxycarbonylphenyl, 2-fluorophenyl, 2-iodophenyl, 4-isopropylphenyl, 2-methoxyphenyl, 4-methoxyphenyl, 2-methylphenyl, 3-methylphenyl, 4-methylphenyl, 5-methyl-2-nitrophenyl, 4-methylsulfonylphenyl, naphth-2-yl, 2-nitrophenyl, 3-nitrophenyl, 4-nitrophenyl, 2,3,4,5,6-pentafluorophenyl, phenyl, 2-trifluoromethoxyphenyl, 3-trifluoromethoxyphenyl, 4-trifluoromethoxyphenyl, 2-trifluoromethylphenyl, 3-trifluoromethylphenyl, 4-trifluoromethylphenyl, 2-trifluoromethylsulfanylphenyl, 4-trifluoromethylsulfanylphenyl, and the like.

"Bicycloaryl" means a bicyclic ring assembly wherein the rings are linked by a single bond or fused and at least one of the rings comprising the assembly is aromatic. $C_X$ bicycloaryl and $C_{X-Y}$ bicycloaryl are typically used where X and Y indicate the number of carbon atoms in the bicyclic ring assembly and directly attached to the ring. For example, $C_{9-10}$ bicycloaryl includes cyclohexylphenyl, 1,2-dihydronaphthyl, 2,4-dioxo-1,2,3,4-tetrahydronaphthyl, indanyl, indenyl, 1,2,3,4-tetrahydronaphthyl, and the like.

"Cycloalkyl" means a saturated or partially unsaturated, monocyclic, fused bicyclic or bridged polycyclic ring assembly. $C_X$ cycloalkyl and $C_{X-Y}$ cycloalkyl are typically used where X and Y indicate the number of carbon atoms in the ring assembly. For example, $C_{3-10}$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

"Cycloalkylene" means a divalent saturated or partially unsaturated, monocyclic ring or bridged polycyclic ring assembly. $C_X$ cycloalkylene and $C_{X-Y}$ cycloalkylene are typically used where X and Y indicate the number of carbon atoms in the ring assembly.

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" or "Halogen" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted $(C_{1-3})$alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom" refers to an atom that is not a carbon atom. Particular examples of heteroatoms include, but are not limited to nitrogen, oxygen, and sulphur.

"Heteroatom moiety" includes a moiety where the atom by which the moiety is attached is not a carbon. Examples of heteroatom moieties include —N=, —NR—, —N$^+$(O$^-$)=, —O—, —S— or —S(O)$_2$—, wherein R is further substituent.

"Heterocycloalkylene" means cycloalkylene, as defined in this Application, provided that one or more of the ring member carbon atoms indicated, is replaced by a heteroatom.

"Heteroaryl" means a five or six membered aromatic ring, as defined in this Application, provided that one or more of the ring carbon atoms indicated are replaced by a heteroatom. For example, optionally substituted hetero$(C_{5-13})$aryl as used in this Application includes, but is not limited to, 4-amino-2- hydroxypyrimidin-5-yl, dibenzofuranyl, benzothiazol-2-yl, 1H-benzoimidazol-2-yl, 2-bromopyrid-5-yl, 5-bromopyrid-2-yl, 4-carbamoylthiazol-2-yl, 3-carboxypyrid-4-yl, 5-carboxy-2,6-dimethylpyrid-3-yl, 3,5-dimethylisoxazol-4-yl, 5-ethoxy-2,6-dimethylpyrid-3-yl, 5-fluoro-6-hydroxypyrimidin-4-yl, fur-2-yl, fur-3-yl, 5-hydroxy-4,6-dimethylpyrid-3-yl, 8-hydroxy-5,7-dimethylquinolin-2-yl, 5-hydroxymethylisoxazol-3-yl, 3-hydroxy-6-methylpyrid-2-yl, 3-hydroxypyrid-2-yl, 1H-imidazol-2-yl, 1H-imidazol-4-yl, 1H-indol-3-yl, isothiazol-4-yl, isoxazol-4-yl, 2-methylfur-3-yl, 5-methylfur-2-yl, 1-methyl-1H-imidazol-2-yl, 5-methyl-3H-imidazol-4-yl, 5-methylisoxazol-3-yl, 5-methyl-2H-pyrazol-3-yl, 3-methylpyrid-2-yl, 4-methylpyrid-2-yl, 5-methylpyrid-2-yl, 6-methylpyrid-2-yl, 2-methylpyrid-3-yl, 2-methylthiazol-4-yl, 5-nitropyrid-2-yl, 2H-pyrazol-3-yl, 3H-pyrazol-4-yl, pyridazin-3-yl, pyrid-2-yl, pyrid-3-yl, pyrid-4-yl, 5-pyrid-3-yl-2H-[1,2,4]triazol-3-yl, pyrimidin-4-yl, pyrimidin-5-yl, 1H-pyrrol-3-yl, quinolin-2-yl, 1H-tetrazol-5-yl, thiazol-2-yl, thiazol-5-yl, thien-2-yl, thien-3-yl, 2H-[1,2,4]triazol-3-yl, 3H-[1,2,3]triazol-4-yl, 5-trifluoromethylpyrid-2-yl, and the like. Suitable protecting groups include tert-butoxycarbonyl, benzyloxycarbonyl, benzyl, 4-methoxybenzyl, 2-nitrobenzyl, and the like.

"Heterobicycloaryl" means bicycloaryl, as defined in this Application, provided that one or more of the ring carbon atoms indicated are replaced by a heteroatom. For example, hetero($C_{8-10}$)bicycloaryl as used in this Application includes, but is not limited to, 2-amino-4-oxo-3,4-dihydropteridin-6-yl, and the like. In general, the term heterobicycloaryl as used in this Application includes, for example, benzo[1,3]dioxol-5-yl, 3,4-dihydro-2H-[1,8]naphthyridinyl, 3,4-dihydro-2H-quinolinyl, 2,4-dioxo-3,4-dihydro-2H-quinazolinyl, 1,2,3,4,5,6-hexahydro[2,2']bipyridinylyl, 3-oxo-2,3-dihydrobenzo[1,4]oxazinyl, 5,6,7,8-tetrahydroquinolinyl, and the like.

"Heterocycloalkyl" means cycloalkyl, as defined in this Application, provided that one or more of the ring carbon atoms indicated are replaced by a heteroatom.

"Hydroxy" means the radical —OH.

"Isomers" mean any compound having an identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Oxaalkyl" means an alkyl, as defined above, except where one or more oxygen atoms (—O—) are positioned between carbon atoms of the alkyl. For example, an ($C_{2-6}$)oxaalkyl refers to a chain comprising between 2 and 6 carbons and one or more oxygen atoms positioned between the carbon atoms.

"Oxoalkyl" means an alkyl, further substituted with a carbonyl group. The carbonyl group may be an aldehyde, ketone, ester, amide, acid or acid chloride.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of inhibitors of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl) benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. For example an inhibitor comprising a hydroxy group may be administered as an ester that is converted by hydrolysis in vivo to the hydroxy compound. Alternatively, an inhibitor comprising a hydroxy group may be administered as an ester and converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulphonates, ethanesulphonates, benzenesulphonates, p-toluenesulphonates, cyclohexylsulphamates and quinates.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$CR_1R_2R_3$ where $R_1$, $R_2$, and $R_3$ may each independently be hydrogen or any other substituent where the atom alpha to the carbon is a heteroatom. Hence, $CF_3$, $CH_2OH$ and $CH_2CN$ are all $C_1$ alkyls.

DETAILED DESCRIPTION OF THE INVENTION

The present invention relates to compounds, compositions, kits and articles of manufacture that may be used to inhibit histone deacetylases (referred to herein as HDACs). The compounds may optionally be more particularly used as inhibitors of Class I HDACs, and optionally as inhibitors of HDAC8.

At least seventeen human genes that encode proven or putative HDACs have been identified to date, some of which are described in Johnstone, R. W., "Histone-Deacetylase Inhibitors: Novel Drugs for the Treatment of Cancer", Nature Reviews, Volume I, pp. 287-299, (2002) and PCT Publication Nos. 00/10583, 01/18045, 01/42437 and 02/08273.

HDACs have been categorized into three distinct classes based on their relative size and sequence homology. The different HDACs (*Homo sapiens*), HDAC classes, sequences and references describing the different HDACs are provided in Tables 1-3.

TABLE 1

CLASS I HDACs

| HDAC | GenBank Accession Number | Reference |
|---|---|---|
| 1 | NP_004955 | Histone deacetylase: a regulator of transcription, Wolffe, A. P., Science 272 (5260), 371-372 (1996) |
| 2 | NP_001518 | Isolation and mapping of a human gene (RPD3L1) that is homologous to RPD3, a transcription factor in *Saccharomyces cerevisiae*; Furukawa, Y., Kawakami, T., Sudo, K., Inazawa, J., Matsumine, A., Akiyama, T. and Nakamura, Y., Cytogenet. Cell Genet. 73 (1-2), 130-133 (1996) |

TABLE 1-continued

CLASS I HDACs

| HDAC | GenBank Accession Number | Reference |
|---|---|---|
| 3 | NP_003874 | Isolation and characterization of cDNAs corresponding to an additional member of the human histone deacetylase gene family, Yang, W. M., Yao, Y. L., Sun, J. M., Davie, J. R. and Seto, E., J. Biol. Chem. 272 (44), 28001-28007 (1997) |
| 8 | NP_060956 | Buggy, J. J., Sideris, M. L., Mak, P., Lorimer, D. D., McIntosh, B. and Clark, J. M. Biochem. J. 350 Pt 1, 199-205 (2000) |
| 11 | NP_079103 | Cloning and Functional Characterization of HDAC11, a Novel Member of the Human Histone Deacetylase Family, Gao, L., Cueto, M. A., Asselbergs, F. and Atadja, P., J. Biol. Chem. 277 (28), 25748-25755 (2002) |

TABLE 2

CLASS II HDACs

| HDAC | GenBank Accession Number | Reference |
|---|---|---|
| 4 | NP_006028 | Transcriptional control. Sinful repression, Wolffe, A. P., Nature 387 (6628), 16-17 (1997) |
| 5 | NP_631944 | Prediction of the coding sequences of unidentified human genes. IX. The complete sequences of 100 new cDNA clones from brain which can code for large proteins in vitro, Nagase, T., Ishikawa, K., Miyajima, N., Tanaka, A., Kotani, H., Nomura, N. and Ohara, O., DNA Res. 5 (1), 31-39 (1998) |
| 6 | NP_006035 | Transcriptional control. Sinful repression, Wolffe, A. P., Nature 387 (6628), 16-17 (1997) |
| 7 | NP_057680 | Isolation of a novel histone deacetylase reveals that class I and class II deacetylases promote SMRT-mediated repression, Kao, H. Y., Downes, M., Ordentlich, P. and Evans, R. M., Genes Dev. 14 (1), 55-66 (2000) |
| 9 | NP_478056 | MEF-2 function is modified by a novel co-repressor, MITR, Sparrow, D. B., Miska, E. A., Langley, E., Reynaud-Deonauth, S., Kotecha, S., Towers, N., Spohr, G., Kouzarides, T. and Mohun, T. J., EMBO J. 18 (18), 5085-5098 (1999) |
| 10 | NP_114408 | Isolation and characterization of mammalian HDAC10, a novel histone deacetylase, Kao, H. Y., Lee, C. H., Komarov, A., Han, C. C. and Evans, R. M., J. Biol. Chem. 277 (1), 187-193 (2002) |

TABLE 3

CLASS III HDACs

| HDAC | GenBank Accession Number | Reference |
|---|---|---|
| Sirtuin 1 | NP_036370 | Characterization of five human cDNAs with homology to the yeast SIR2 gene: Sir2-like proteins (sirtuins) metabolize NAD and may have protein ADP-ribosyltransferase activity; Frye, R. A.; Biochem. Biophys. Res. Commun. 260 (1), 273-279 (1999) |
| Sirtuin 2 | NP_085096/ NP_036369 | A 'double adaptor' method for improved shotgun library construction; Andersson, B., Wentland, M. A., Ricafrente, J. Y., Liu, W. |

TABLE 3-continued

CLASS III HDACs

| HDAC | GenBank Accession Number | Reference |
|---|---|---|
| | | and Gibbs, R. A.; Anal. Biochem. 236 (1), 107-113 (1996) |
| Sirtuin 3 | NP_036371 | Characterization of five human cDNAs with homology to the yeast SIR2 gene: Sir2-like proteins (sirtuins) metabolize NAD and may have protein ADP-ribosyltransferase activity; Frye, R. A.; Biochem. Biophys. Res. Commun. 260 (1), 273-279 (1999) |
| Sirtuin 4 | NP_036372 | Characterization of five human cDNAs with homology to the yeast SIR2 gene: Sir2-like proteins (sirtuins) metabolize NAD and may have protein ADP-ribosyltransferase activity; Frye, R. A.; Biochem. Biophys. Res. Commun. 260 (1), 273-279 (1999) |
| Sirtuin 5 | NP_112534/ NP_036373 | Characterization of five human cDNAs with homology to the yeast SIR2 gene: Sir2-like proteins (sirtuins) metabolize NAD and may have protein ADP-ribosyltransferase activity; Frye, R. A.; Biochem. Biophys. Res. Commun. 260 (1), 273-279 (1999) |
| Sirtuin 6 | NP_057623 | Phylogenetic classification of prokaryotic and eukaryotic Sir2-like proteins; Frye, R. A.; Biochem. Biophys. Res. Commun. 273 (2), 793-798 (2000) |
| Sirtuin 7 | NP_057622 | Phylogenetic classification of prokaryotic and eukaryotic Sir2-like proteins; Frye, R. A.; Biochem. Biophys. Res. Commun. 273 (2), 793-798 (2000) |

Of particular note are Class I HDACs. All Class I HDACs appear to be sensitive to inhibition by trichostatin A (TSA). Also of particular note is HDAC8, a protein whose crystal structure Applicants recently determined.

HDAC8 is a 377 residue, 42 kDa protein localized to the nucleus of a wide array of tissues, as well as several human tumor cell lines. The wild-type form of full length HDAC8 is described in GenBank Accession Number NP 060956; Buggy, J. J., Sideris, M. L., Mak, P., Lorimer, D. D., McIntosh, B. and Clark, J. M., Cloning and characterization of a novel human histone deacetylase, HDAC8, Biochem. J. 350 Pt 1, 199-205 (2000). $Zn^{2+}$ is likely native to the protein and required for HDAC8 activity.

1. Crystal Structure for HDAC

Syrrx, Inc. in San Diego, Calif. recently solved the crystal structure for HDAC8. Knowledge of the crystal structure was used to guide the design of the HDAC inhibitors provided herein.

Figure 1:
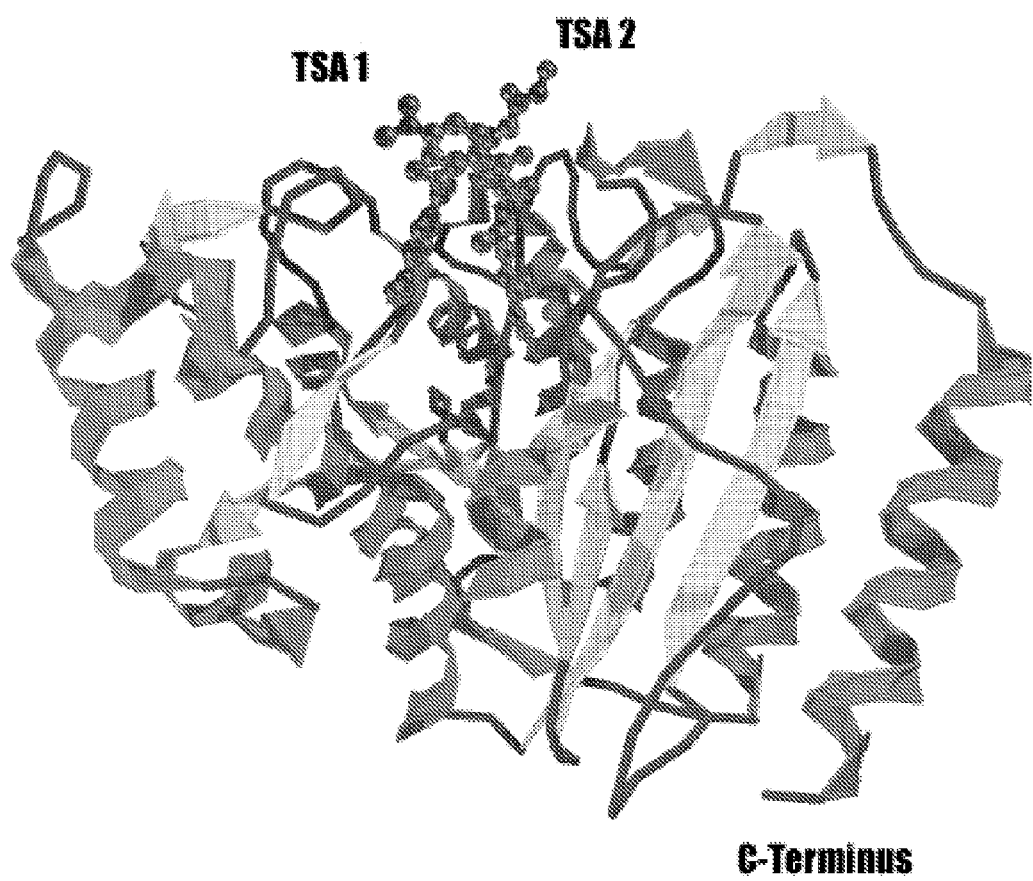
FIG. 1 illustrates a ribbon diagram overview of the structure of HDAC8, highlighting the secondary structural elements of the protein.

FIG. 1 illustrates a ribbon diagram overview of the structure of HDAC8, highlighting the secondary structural elements of the protein. HDAC8 was found to have a single domain structure belonging to the open α/β class of folds. The structure consists of a central 8-stranded parallel β-sheet sandwiched between layers of α-helices. The ligand binding clefts lie almost in the plane of the central β-sheet, and are formed primarily by loops emanating from the carboxy-terminal ends of the β-strands comprising the sheet. There are two large structural extensions, which occur beyond the core of the α/β motif, off the second and last β-strands of the central β-sheet. Residues contained in the extension off the second β-strand form a globular "cap" over the core of the protein, play an important role in defining the shape of the ligand binding pockets, and are involved in a number of key interactions with the bound ligands.

2. HDAC Inhibitors

In one embodiment, HDAC inhibitors of the present invention are provided that comprise the formula

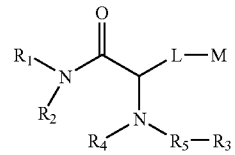

wherein $R_1$ comprises a moiety attached to the nitrogen selected from the group consisting of a substituted straight chained $C_{1-12}$ alkyl, $C_{2-12}$ oxaalkyl and $C_{2-12}$ aminoalkyl where at least one of the substituents is selected from the group consisting of substituted and unsubstituted straight chained $C_{1-12}$ alkyls, $C_{2-12}$ oxaalkyls or $C_{2-12}$ aminoalkyls and substituted and unsubstituted 3, 4, 5, 6, 7 or 8 membered rings;

$R_2$ comprises a moiety attached to the nitrogen selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring;

$R_3$ and $R_4$ are each independently selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, with the proviso that $R_3$ and $R_4$ are not both hydrogen;

$R_5$ is selected from the group consisting of a carbonyl, a substituted or unsubstituted $C_{1-3}$ alkyl, a substituted or unsubstituted —$C_{1-3}$ alkyl-C(O), a substituted or unsubstituted —C(O)—$C_{1-3}$ alkyl, and a substituted or unsubstituted —C(O)C(O)$C_{1-3}$ alkyl;

M is a substituent capable of complexing with a protein metal ion; and

L is a substituent comprising a chain of 3-12 atoms connecting the M substituent to the carbon atom alpha to the L substituent.

According to this embodiment, in one variation, the substituted straight chained $C_{1-12}$ alkyl, $C_{2-12}$ oxaalkyl or $C_{2-12}$ aminoalkyl of $R_1$ may optionally be a substituted straight chained $C_{1-6}$ alkyl, $C_{2-6}$ oxaalkyl or $C_{2-6}$ aminoalkyl and optionally a substituted straight chained $C_{1-4}$ alkyl, $C_{2-4}$ oxaalkyl or $C_{2-4}$ aminoalkyl. In a further variation, the substituted straight chained $C_{1-12}$ alkyl, $C_{2-12}$ oxaalkyl or $C_{2-12}$ aminoalkyl may also optionally be 1, 2, 3, 4, 5, or 6, atoms in length.

Also according to this embodiment, the substituent attached to the substituted straight chained $C_{1-12}$ alkyl, $C_{2-12}$ oxaalkyl or $C_{2-12}$ aminoalkyl of $R_1$ optionally renders the alkyl, oxaalkyl or aminoalkyl a branched alkyl, oxaalkyl or aminoalkyl. For example, an alkyl substituent off of a straight chained alkyl is intended herein to refer to a branched alkyl. Hence, t-butyl is an example of a straight chained $C_1$ alkyl further substituted with three $C_1$ alkyls.

Also according to this embodiment, the substituent attached to the substituted straight chained $C_{1-12}$ alkyl, $C_{2-12}$ oxaalkyl or $C_{2-12}$ aminoalkyl of $R_1$ optionally is a substituted or unsubstituted five or six membered ring. The five or six membered ring may optionally be alicyclic (e.g., cyclopentane, cyclopentene, cyclopentadiene, cyclohexane, cyclohexene, cyclohexadiene) or heteroalicyclic. The five or six membered ring may also optionally be an aromatic ring including aromatic rings that comprise one or more heteroatoms. In one variation, the ring is an aryl, such as phenyl or a heteroaryl. Additional rings optionally may be fused or linked to the five or six membered ring.

Also according to this embodiment, $R_2$ may optionally comprise a relative small moiety selected from the group consisting of hydrogen and a moiety that has a maximum chain length of non-hydrogen atoms of six or less, optionally four or less. The moiety may also optionally be hydrophobic in nature, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

Also according to this embodiment, $R_3$ or $R_4$ may comprise a moiety selected from the group consisting of a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, when the other of $R_3$ and $R_4$ is a moiety selected from the group consisting of hydrogen and a moiety that has a maximum chain length of non-hydrogen atoms of six or less, optionally four or less.

The first, larger of such $R_3$ or $R_4$ moieties may comprise a moiety selected from the group consisting of a substituted straight chained $C_{1-12}$ alkyl, $C_{2-12}$ aminoalkyl and $C_{2-12}$ oxaalkyl where at least one of the substituents is selected from the group of substituted and unsubstituted straight chained $C_{1-12}$ alkyls, $C_{2-12}$ oxaalkyls or $C_{2-12}$ aminoalkyls and substituted and unsubstituted 3, 4, 5, 6, 7 or 8 membered rings. The second, smaller of such $R_3$ or $R_4$ moieties may optionally be hydrophobic in nature, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

When $R_3$ comprises a substituted 6 membered ring, in one variation the substituent is beta relative to $R_5$. When $R_3$ comprises an aryl or heteroaryl attached to $R_5$, the aryl or heteroaryl may optionally be meta substituted relative to $R_5$. The further substituent is optionally a hydrophobic substituent, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

In another embodiment, HDAC inhibitors of the present invention are provided that comprise the formula

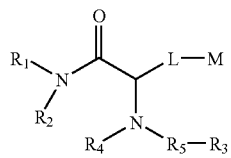

wherein
$R_1$ and $R_2$ each independently comprise a moiety attached to the nitrogen selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, with the proviso that $R_1$ and $R_2$ are not both hydrogen;

one of $R_3$ and $R_4$ is selected from the group consisting of a substituted or unsubstituted straight chained $C_{1-12}$ alkyl, $C_{2-12}$ aminoalkyl or $C_{2-12}$ oxaalkyl, and a substituted or unsubstituted 3, 4, 5, 6, 7 or 8 membered ring, when the other of $R_3$ and $R_4$ is a moiety selected from the group consisting of hydrogen and a moiety that has a maximum chain length of non-hydrogen atoms of six or less, optionally four or less.

$R_5$ is selected from the group consisting of a carbonyl, a substituted or unsubstituted $C_{1-3}$ alkyl, a substituted or unsubstituted —$C_{1-3}$ alkyl-C(O), a substituted or unsubstituted —C(O)—$C_{1-3}$ alkyl, and a substituted or unsubstituted —C(O)C(O)$C_{1-3}$ alkyl;

M is a substituent capable of complexing with a protein metal ion; and

L is a substituent comprising a chain of 3-12 atoms connecting the M substituent to the carbon atom alpha to the L substituent.

According to this embodiment, in one variation, the first, larger of such $R_3$ or $R_4$ moieties is selected from the group consisting of a substituted straight chained $C_{1-12}$ alkyl, $C_{2-12}$ aminoalkyl and $C_{2-12}$ oxaalkyl where at least one of the substituents is selected from the group consisting of substituted and unsubstituted straight chained $C_{1-12}$ alkyls, $C_{2-12}$ oxaalkyls or $C_{2-12}$ aminoalkyls and substituted or unsubstituted 3, 4, 5, 6, 7 or 8 membered rings. The second, smaller of such $R_3$ or $R_4$ moieties may optionally be hydrophobic in nature, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

Also according to this embodiment, in one variation, $R_1$ comprises a moiety attached to the nitrogen selected from the group consisting of a substituted straight chained $C_{1-12}$ alkyl, $C_{2-12}$ oxaalkyl and $C_{2-12}$ aminoalkyl where at least one of the substituents is selected from the group consisting of substituted and unsubstituted straight chained $C_{1-12}$ alkyls, $C_{2-12}$ oxaalkyls or $C_{2-12}$ aminoalkyls and substituted or unsubstituted 3, 4, 5, 6, 7 or 8 membered rings. According to this embodiment, the substituted straight chained $C_{1-12}$ alkyl, $C_{2-12}$ oxaalkyl or $C_{2-12}$ aminoalkyl of $R_1$ may optionally be a substituted straight chained $C_{1-6}$ alkyl, $C_{2-6}$ oxaalkyl or $C_{2-6}$ aminoalkyl and optionally a substituted straight chained $C_{1-4}$ alkyl, $C_{2-4}$ oxaalkyl or $C_{2-4}$ aminoalkyl. Also according to this variation, the substituent attached to the substituted straight chained $C_{1-12}$ alkyl, $C_{2-12}$ oxaalkyl or $C_{2-12}$ aminoalkyl of $R_1$ optionally renders the alkyl, oxaalkyl or aminoalkyl a branched alkyl, oxaalkyl or aminoalkyl.

According to this variation, the substituted straight chained $C_{1-12}$ alkyl, $C_{2-12}$ oxaalkyl or $C_{2-12}$ aminoalkyl of $R_1$ may optionally be a substituted straight chained $C_{1-6}$ alkyl, $C_{2-6}$ oxaalkyl or $C_{2-6}$ aminoalkyl and optionally a substituted straight chained $C_{1-4}$ alkyl, $C_{2-4}$ oxaalkyl or $C_{2-4}$ aminoalkyl.

In a further variation, the substituted straight chained $C_{1-12}$ alkyl, $C_{2-12}$ oxaalkyl or $C_{2-12}$ aminoalkyl may also optionally be 1, 2, 3, 4, 5, or 6, atoms in length.

Also according to this variation, the substituent attached to the substituted straight chained $C_{1-12}$ alkyl, $C_{2-12}$ oxaalkyl or $C_{2-12}$ aminoalkyl of $R_1$ optionally renders the alkyl, oxaalkyl or aminoalkyl a branched alkyl, oxaalkyl or aminoalkyl. For example, an alkyl substituent off of a straight chained alkyl is intended herein to refer to a branched alkyl. Hence, t-butyl is an example of a straight chained $C_1$ alkyl further substituted with three $C_1$ alkyls.

Also according to this variation, the substituent attached to the substituted straight chained $C_{1-12}$ alkyl, $C_{2-12}$ oxaalkyl or $C_{2-12}$ aminoalkyl of $R_1$ optionally is a substituted or unsubstituted five or six membered ring. The five or six membered ring may optionally be alicyclic (e.g., cyclopentane, cyclopentene, cyclopentadiene, cyclohexane, cyclohexene, cyclohexadiene) or heteroalicyclic. The five or six membered ring may also optionally be an aromatic ring including aromatic rings that comprise one or more heteroatoms. In one variation, the ring is an aryl, such as phenyl or a heteroaryl. Additional rings optionally may be fused or linked to the five or six membered ring.

When $R_3$ comprises a substituted 6 membered ring, in one variation the substituent is beta relative to $R_5$. When $R_3$ comprises an aryl or heteroaryl attached to $R_5$, the aryl or heteroaryl may optionally be meta substituted relative to $R_5$. The further substituent is optionally a hydrophobic substituent, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

In yet another embodiment, HDAC inhibitors of the present invention are provided that comprise the formula

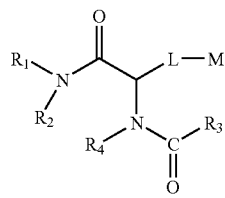

wherein
- $R_1$ and $R_2$ each independently comprise a moiety attached to the nitrogen selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, with the proviso that $R_1$ and $R_2$ are not both hydrogen;
- $R_3$ and $R_4$ are each independently selected from the group consisting of a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring;
- M is a substituent capable of complexing with a protein metal ion; and
- L is a substituent comprising a chain of 3-12 atoms connecting the M substituent to the carbon atom alpha to the L substituent.

According to this embodiment, in one variation, $R_1$ is a substituted straight chained $C_{1-12}$ alkyl, $C_{2-12}$ oxaalkyl or $C_{2-12}$ aminoalkyl that may also optionally be a substituted straight chained $C_{1-6}$ alkyl, $C_{2-6}$ oxaalkyl or $C_{2-6}$ aminoalkyl and optionally a substituted straight chained $C_{1-4}$ alkyl, $C_{2-4}$ oxaalkyl or $C_{2-4}$ aminoalkyl. In a further variation, the substituted straight chained $C_{1-12}$ alkyl, $C_{2-12}$ oxaalkyl or $C_{2-12}$ aminoalkyl may also optionally be 1, 2, 3, 4, 5, or 6, atoms in length.

According to this variation, the substituent attached to the substituted straight chained $C_{1-12}$ alkyl, $C_{2-12}$ oxaalkyl or $C_{2-12}$ aminoalkyl of $R_1$ optionally renders the alkyl, oxaalkyl or aminoalkyl a branched alkyl, oxaalkyl or aminoalkyl. For example, an alkyl substituent off of a straight chained alkyl is intended herein to refer to a branched alkyl. Hence, t-butyl is an example of a straight chained $C_1$ alkyl further substituted with three $C_1$ alkyls.

Also according to this variation, the substituent attached to the substituted straight chained $C_{1-12}$ alkyl, $C_{2-12}$ oxaalkyl or $C_{2-12}$ aminoalkyl of $R_1$ optionally is a substituted or unsubstituted five or six membered ring. The five or six membered ring may optionally be alicyclic (e.g., cyclopentane, cyclopentene, cyclopentadiene, cyclohexane, cyclohexene, cyclohexadiene) or heteroalicyclic. The five or six membered ring may also optionally be an aromatic ring including aromatic rings that comprise one or more heteroatoms. In one variation, the ring is an aryl, such as phenyl or a heteroaryl. Additional rings optionally may be fused or linked to the five or six membered ring.

Also according to this embodiment, $R_2$ may optionally comprise a relative small moiety selected from the group consisting of hydrogen and a moiety that has a maximum chain length of non-hydrogen atoms of six or less, optionally four or less. The moiety may also optionally be hydrophobic in nature, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

Also according to this embodiment, $R_3$ or $R_4$ may comprise a moiety selected from the group consisting of a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, when the other of $R_3$ and $R_4$ is a moiety selected from the group consisting of hydrogen and a moiety that has a maximum chain length of non-hydrogen atoms of six or less, optionally four or less.

The first, larger of such $R_3$ or $R_4$ moieties may comprise a moiety selected from the group consisting of a substituted straight chained $C_{1-12}$ alkyl, $C_{2-12}$ aminoalkyl and $C_{2-12}$ oxaalkyl where at least one of the substituents is selected from the group consisting of substituted and unsubstituted straight chained $C_{1-12}$ alkyls, $C_{2-12}$ oxaalkyls or $C_{2-12}$ aminoalkyls and substituted and unsubstituted 3, 4, 5, 6, 7 or 8 membered rings. The second, smaller of such $R_3$ or $R_4$ moieties may optionally be hydrophobic in nature, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

When $R_3$ comprises a substituted 6 membered ring, in one variation the substituent is beta relative to the carbonyl. When $R_3$ comprises an aryl or heteroaryl attached to the carbonyl, the aryl or heteroaryl may optionally be meta substituted relative to the carbonyl. The further substituent is optionally a hydrophobic substituent, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

In another embodiment, HDAC inhibitors of the present invention are provided that comprise the formula

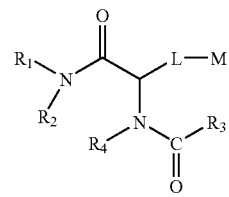

wherein
- $R_1$ comprises a moiety attached to the nitrogen selected from the group consisting of a substituted straight chained $C_{1-12}$ alkyl, $C_{2-12}$ oxaalkyl and $C_{2-12}$ aminoalkyl where at least one of the substituents is selected from the group consisting of substituted and unsubstituted straight chained $C_{1-12}$ alkyls, $C_{2-12}$ oxaalkyls or $C_{2-12}$ aminoalkyls and substituted and unsubstituted 3, 4, 5, 6, 7 or 8 membered rings;
- $R_2$ comprises a moiety attached to the nitrogen selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring;
- $R_3$ and $R_4$ are each independently selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, with the proviso that $R_3$ and $R_4$ are not both hydrogen;

M is a substituent capable of complexing with a protein metal ion; and

L is a substituent comprising a chain of 3-12 atoms connecting the M substituent to the carbon atom alpha to the L substituent.

According to this embodiment, in one variation, the substituted straight chained $C_{1-12}$ alkyl, $C_{2-12}$ oxaalkyl or $C_{2-12}$ aminoalkyl of $R_1$ may optionally be a substituted straight chained $C_{1-6}$ alkyl, $C_{2-6}$ oxaalkyl or $C_{2-6}$ aminoalkyl and optionally a substituted straight chained $C_{1-4}$ alkyl, $C_{2-4}$ oxaalkyl or $C_{2-4}$ aminoalkyl. In a further variation, the substituted straight chained $C_{1-12}$ alkyl, $C_{2-12}$ oxaalkyl or $C_{2-12}$ aminoalkyl may also optionally be 1, 2, 3, 4, 5, or 6, atoms in length.

Also according to this embodiment, the substituent attached to the substituted straight chained $C_{1-12}$ alkyl, $C_{2-12}$ oxaalkyl or $C_{2-12}$ aminoalkyl of $R_1$ optionally renders the alkyl, oxaalkyl or aminoalkyl a branched alkyl, oxaalkyl or aminoalkyl. For example, an alkyl substituent off of a straight chained alkyl is intended herein to refer to a branched alkyl. Hence, t-butyl is an example of a straight chained $C_1$ alkyl further substituted with three $C_1$ alkyls.

Also according to this embodiment, the substituent attached to the substituted straight chained $C_{1-12}$ alkyl, $C_{2-12}$ oxaalkyl or $C_{2-12}$ aminoalkyl of $R_1$ optionally is a substituted or unsubstituted five or six membered ring. The five or six membered ring may optionally be alicyclic (e.g., cyclopentane, cyclopentene, cyclopentadiene, cyclohexane, cyclohexene, cyclohexadiene) or heteroalicyclic. The five or six membered ring may also optionally be an aromatic ring including aromatic rings that comprise one or more heteroatoms. In one variation, the ring is an aryl, such as phenyl or a heteroaryl. Additional rings optionally may be fused or linked to the five or six membered ring.

Also according to this embodiment, $R_2$ may optionally comprise a relative small moiety selected from the group consisting of hydrogen and a moiety that has a maximum chain length of non-hydrogen atoms of six or less, optionally four or less. The moiety may also optionally be hydrophobic in nature, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

Also according to this embodiment, $R_3$ or $R_4$ may comprise a moiety selected from the group consisting of a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, when the other of $R_3$ and $R_4$ is a moiety selected from the group consisting of hydrogen and a moiety that has a maximum chain length of non-hydrogen atoms of six or less, optionally four or less.

The first, larger of such $R_3$ or $R_4$ moieties may comprise a moiety selected from the group consisting of a substituted straight chained $C_{1-12}$ alkyl, $C_{2-12}$ aminoalkyl and $C_{2-12}$ oxaalkyl where at least one of the substituents is selected from the group consisting of substituted and unsubstituted straight chained $C_{1-12}$ alkyls, $C_{2-12}$ oxaalkyls or $C_{2-12}$ aminoalkyls and substituted and unsubstituted 3, 4, 5, 6, 7 or 8 membered rings. The second, smaller of such $R_3$ or $R_4$ moieties may optionally be hydrophobic in nature, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

When $R_3$ comprises a substituted 6 membered ring, in one variation the substituent is beta relative to $R_5$. When $R_3$ comprises an aryl or heteroaryl attached to $R_5$, the aryl or heteroaryl may optionally be meta substituted relative to $R_5$. The further substituent is optionally a hydrophobic substituent, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

In another embodiment, HDAC inhibitors of the present invention are provided that comprise the formula

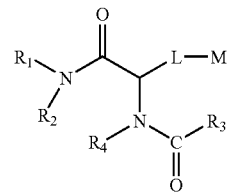

wherein $R_1$ and $R_2$ each independently comprise a moiety attached to the nitrogen selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, with the proviso that $R_1$ and $R_2$ are not both hydrogen;

one of $R_3$ and $R_4$ is selected from the group consisting of a substituted or unsubstituted straight chained $C_{1-12}$ alkyl, $C_{1-12}$ aminoalkyl or $C_{1-12}$ oxaalkyl, and a substituted or unsubstituted 3, 4, 5, 6, 7 or 8 membered ring, when the other of $R_3$ and $R_4$ is a moiety selected from the group consisting of hydrogen and a moiety that has a maximum chain length of non-hydrogen atoms of six or less, optionally four or less;

M is a substituent capable of complexing with a protein metal ion; and

L is a substituent comprising a chain of 3-12 atoms connecting the M substituent to the carbon atom alpha to the L substituent.

According to this embodiment, in one variation, the first, larger of such $R_3$ or $R_4$ moieties is selected from the group consisting of a substituted straight chained $C_{1-12}$ alkyl, $C_{2-12}$ aminoalkyl and $C_{2-12}$ oxaalkyl where at least one of the substituents is selected from the group consisting of substituted and unsubstituted straight chained $C_{1-12}$ alkyls, $C_{2-12}$ oxaalkyls or $C_{2-12}$ aminoalkyls and substituted or unsubstituted 3, 4, 5, 6, 7 or 8 membered rings. The second, smaller of such $R_3$ or $R_4$ moieties may optionally be hydrophobic in nature, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

Also according to this embodiment, in one variation, $R_1$ comprises a moiety attached to the nitrogen selected from the group consisting of a substituted straight chained $C_{1-12}$ alkyl, $C_{2-12}$ oxaalkyl and $C_{2-12}$ aminoalkyl where at least one of the substituents is selected from the group consisting of substituted and unsubstituted straight chained $C_{1-12}$ alkyls, $C_{2-12}$ oxaalkyls or $C_{2-12}$ aminoalkyls and substituted or unsubstituted 3, 4, 5, 6, 7 or 8 membered rings. According to this embodiment, the substituted straight chained $C_{1-12}$ alkyl, $C_{2-12}$ oxaalkyl or $C_{2-12}$ aminoalkyl of $R_1$ may optionally be a substituted straight chained $C_{1-6}$ alkyl, $C_{2-6}$ oxaalkyl or $C_{2-6}$ aminoalkyl and optionally a substituted straight chained $C_{1-4}$ alkyl, $C_{2-4}$ oxaalkyl or $C_{2-4}$ aminoalkyl. Also according to this variation, the substituent attached to the substituted straight chained $C_{1-12}$ alkyl, $C_{2-12}$ oxaalkyl or $C_{2-12}$ aminoalkyl of $R_1$ optionally renders the alkyl, oxaalkyl or aminoalkyl a branched alkyl, oxaalkyl or aminoalkyl.

According to this variation, the substituted straight chained $C_{1-12}$ alkyl, $C_{2-12}$ oxaalkyl or $C_{2-12}$ aminoalkyl of $R_1$ may optionally be a substituted straight chained $C_{1-6}$ alkyl, $C_{2-6}$ oxaalkyl or $C_{2-6}$ aminoalkyl and optionally a substituted straight chained $C_{1-4}$ alkyl, $C_{2-4}$ oxaalkyl or $C_{2-4}$ aminoalkyl. In a further variation, the substituted straight chained $C_{1-12}$ alkyl, $C_{2-12}$ oxaalkyl or $C_{2-12}$ aminoalkyl may also optionally be 1, 2, 3, 4, 5, or 6, atoms in length.

Also according to this variation, the substituent attached to the substituted straight chained $C_{1-12}$ alkyl, $C_{2-12}$ oxaalkyl or $C_{2-12}$ aminoalkyl of $R_1$ optionally renders the alkyl, oxaalkyl or aminoalkyl a branched alkyl, oxaalkyl or aminoalkyl. For example, an alkyl substituent off of a straight chained alkyl is intended herein to refer to a branched alkyl. Hence, t-butyl is an example of a straight chained $C_1$ alkyl further substituted with three $C_1$ alkyls.

Also according to this variation, the substituent attached to the substituted straight chained $C_{1-12}$ alkyl, $C_{2-12}$ oxaalkyl or $C_{2-12}$ aminoalkyl of $R_1$ optionally is a substituted or unsubstituted five or six membered ring. The five or six membered ring may optionally be alicyclic (e.g., cyclopentane, cyclopentene, cyclopentadiene, cyclohexane, cyclohexene, cyclohexadiene) or heteroalicyclic. The five or six membered ring may also optionally be an aromatic ring including aromatic rings that comprise one or more heteroatoms. In one variation, the ring is an aryl, such as phenyl or a heteroaryl. Additional rings optionally may be fused or linked to the five or six membered ring.

When $R_3$ comprises a substituted 6 membered ring, in one variation the substituent is beta relative to $R_5$. When $R_3$ comprises an aryl or heteroaryl attached to $R_5$, the aryl or heteroaryl may optionally be meta substituted relative to $R_5$. The further substituent is optionally a hydrophobic substituent, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

In another embodiment, HDAC inhibitors of the present invention are provided that comprise the formula

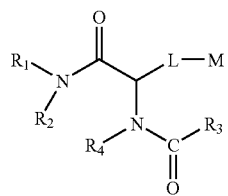

wherein
- $R_1$ and $R_2$ each independently comprise a moiety attached to the nitrogen selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring, with the proviso that $R_1$ and $R_2$ are not both hydrogen;
- $R_3$ comprises a substituted six membered ring attached to the carbonyl carbon wherein at least one of the substituents of the six membered ring is beta relative to atom attached to the carbonyl carbon;
- $R_4$ comprises a moiety selected from the group consisting of hydrogen, a substituted or unsubstituted straight chained $C_{1-12}$ alkyl, $C_{2-12}$ aminoalkyl or $C_{2-12}$ oxaalkyl, and a substituted and unsubstituted 3, 4, 5, 6, 7 or 8 membered ring;
- M is a substituent capable of complexing with a protein metal ion; and
- L is a substituent comprising a chain of 3-12 atoms connecting the M substituent to the carbon atom alpha to the L substituent.

According to this embodiment, in one variation, $R_4$ is a moiety selected from the group consisting of hydrogen and a moiety that has a maximum chain length of nonhydrogen atoms of less than six, optionally less than four.

Also according to this embodiment, in one variation, $R_3$ comprises an aryl attached to the carbonyl carbon that is substituted meta relative to atom attached to the carbonyl carbon. The aryl may be a phenyl ring or a heteroaryl ring. The further substituent is optionally a hydrophobic substituent, such as a $C_{1-4}$ alkyl, $C_{2-4}$ aminoalkyl or $C_{2-4}$ oxaalkyl, —C(O)H, —C(O)—$C_{1-3}$ alkyl, optionally further substituted.

Also according to this embodiment, in one variation, $R_1$ comprises a moiety attached to the nitrogen selected from the group consisting of a substituted straight chained $C_{1-12}$ alkyl, $C_{2-12}$ oxaalkyl and $C_{2-12}$ aminoalkyl where at least one of the substituents is selected from the group consisting of substituted and unsubstituted straight chained $C_{1-12}$ alkyls, $C_{2-12}$ oxaalkyls or $C_{2-12}$ aminoalkyls and substituted or unsubstituted 3, 4, 5, 6, 7 or 8 membered rings. According to this embodiment, the substituted straight chained $C_{1-12}$ alkyl, $C_{2-12}$ oxaalkyl or $C_{2-12}$ aminoalkyl of $R_1$ may optionally be a substituted straight chained $C_{2-6}$ alkyl, $C_{2-6}$ oxaalkyl or $C_{2-6}$ aminoalkyl and optionally a substituted straight chained $C_{1-4}$ alkyl, $C_{2-4}$ oxaalkyl or $C_{2-4}$ aminoalkyl. Also according to this variation, the substituent attached to the substituted straight chained $C_{1-12}$ alkyl, $C_{2-12}$ oxaalkyl or $C_{2-12}$ aminoalkyl of $R_1$ optionally renders the alkyl, oxaalkyl or aminoalkyl a branched alkyl, oxaalkyl or aminoalkyl.

According to this variation, the substituted straight chained $C_{1-12}$ alkyl, $C_{2-12}$ oxaalkyl or $C_{2-12}$ aminoalkyl of $R_1$ may optionally be a substituted straight chained $C_{1-6}$ alkyl, $C_{2-6}$ oxaalkyl or $C_{2-6}$ aminoalkyl and optionally a substituted straight chained $C_{1-4}$ alkyl, $C_{2-4}$ oxaalkyl or $C_{2-4}$ aminoalkyl. In a further variation, the substituted straight chained $C_{1-12}$ alkyl, $C_{2-12}$ oxaalkyl or $C_{2-12}$ aminoalkyl may also optionally be 1, 2, 3, 4, 5, or 6, atoms in length.

Also according to this variation, the substituent attached to the substituted straight chained $C_{1-12}$ alkyl, $C_{2-12}$ oxaalkyl or $C_{2-12}$ aminoalkyl of $R_1$ optionally renders the alkyl, oxaalkyl or aminoalkyl a branched alkyl, oxaalkyl or aminoalkyl. For example, an alkyl substituent off of a straight chained alkyl is intended herein to refer to a branched alkyl. Hence, t-butyl is an example of a straight chained $C_1$ alkyl further substituted with three $C_1$ alkyls.

Also according to this variation, the substituent attached to the substituted straight chained $C_{1-12}$ alkyl, $C_{2-12}$ oxaalkyl or $C_{2-12}$ aminoalkyl of $R_1$ optionally is a substituted or unsubstituted five or six membered ring. The five or six membered ring may optionally be alicyclic (e.g., cyclopentane, cyclopentene, cyclopentadiene, cyclohexane, cyclohexene, cyclohexadiene) or heteroalicyclic. The five or six membered ring may also optionally be an aromatic ring including aromatic rings that comprise one or more heteroatoms. In one variation, the ring is an aryl, such as phenyl or a heteroaryl. Additional rings optionally may be fused or linked to the five or six membered ring.

In regard to each of the above embodiments, when $R_1$, $R_2$ $R_3$ or $R_4$ comprises a $C_{z-y}$ alkyl, aminoalkyl, or oxaalkyl, it is noted that it may comprise one or more double or triple bonds. Also, the alkyl, aminoalkyl, or oxaalkyl may be a $C_{1-6}$, $C_{2-6}$, $C_{1-4}$, $C_{2-4}$, $C_1$, $C_2$, $C_3$, or $C_4$ alkyl, aminoalkyl, or oxaalkyl. Also in regard to $R_1$, $R_2$ $R_3$ or $R_4$, unless otherwise specified, ring substituents on the alkyl, aminoalkyl, or oxaalkyl may be an alicyclic or aromatic ring. In a particular variation, the ring is a five or six membered ring. In a further particular variation, the five or six membered ring is a substituted or unsubstituted alicyclic or aryl. It is noted that the cycloalkyl may optionally be a cycloalkylene, heterocycloalkyl and/or heterocycloalkylene. It is also noted that the aryl may optionally be a bicycloaryl, heteroaryl, and/or heterobicycloaryl.

Particular examples of $R_1$, $R_2$ $R_3$ and $R_4$ substituents that may be employed are illustrated in FIG. 2A.

When $R_3$ comprises a substituted five or six membered ring, in one variation the substituent is beta relative to the carbonyl carbon. When $R_3$ comprises an aryl or heteroaryl attached to the carbonyl carbon, the aryl or heteroaryl may optionally be meta substituted relative to the carbonyl carbon. It has been observed that such beta or meta substitutions, particularly when the leader group is a cinnamate, provide advantageous properties to the inhibitors. Accordingly, in one embodiment, HDAC inhibitors of the present invention are provided that comprise the formula

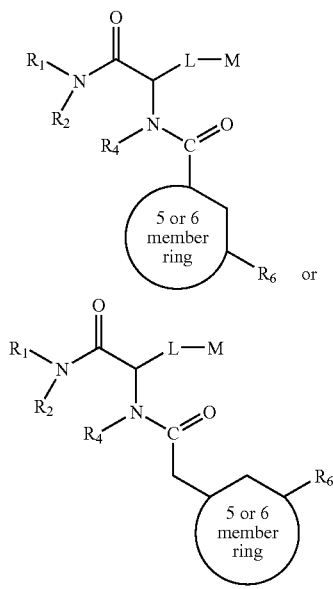

where $R_6$, is a hydrophobic substituent. Examples of hydrophobic substituents that may be used include $C_{1-4}$ alkyl, $C_{2-4}$ aminoalkyl or $C_{2-4}$ oxaalkyl, —C(O)H, —C(O)—$C_{1-3}$ alkyl, optionally further substituted. FIG. 2B provides particular examples of $R_3$ substituents that may be employed when $R_3$ comprises a five or six membered ring.

In regard to each of the above embodiments, substituent M may be any substituent that is capable of complexing with a metal ion, and optionally more particularly a zinc ion since a zinc ion is known to be present in the catalytic site of histone deacetylases. Hence, the M substituent may facilitate inhibitor binding by complexing with the zinc ion present in the catalytic site of histone deacetylases.

Examples of substituents capable of complexing with a zinc ion that may be used as the M substituent include, but are not limited to trifluoroacetyl (—C(O)—$CF_3$), —NH—P(O)OH—$CH_3$, sulfonamides (—$SO_2NH_2$), thiols (—SH), and carbonyl groups having the formula —C(O)—$R_7$ wherein $R_7$ is hydroxylamino, hydroxyl, amino, alkylamino, or an alkyloxy group.

In one particular variation, M is a hydroxamic acid (—C(O)—NHOH). It is noted that hydroxamic acids, such as trichostatin A, have been shown to be effective inhibitors against histone deacetylases by complexing with the zinc ion present in the catalytic site of histone deacetylases.

In regard to each of the above embodiments, the leader group, L, may be any substituent comprising a chain of 3-12 atoms connecting the M substituent to the carbon atom alpha to the L substituent. The number of atoms in the chain serves to extend the zinc complexing substituent, M, a sufficient distance away from the remainder of the inhibitor so as to allow the zinc complexing substituent to interact with the zinc ion while the hydrophobic $R_1$, $R_2$, and $R_3$ groups interact with hydrophobic regions in the binding pocket of the histone deacetylase.

A variety of different leader groups may be used in the HDAC inhibitors of the present invention. Examples of particular leader groups that may be used are shown in FIG. 2C.

In one embodiment, the leader group, L, comprises a chain of 3-12 atoms that extend between the carbon alpha to the leader group and the M substituent, optionally 3-9 and optionally 4-8 atoms. In one variation, the number of atoms in the chain of atoms extending between the carbon alpha to the leader group and the M substituent is 3, 4, 5, 6, 7, 8 or 9 atoms.

It is noted that the chain of atoms extending between the carbon alpha to the leader group and the M substituent may consist only of carbon atoms. Alternatively, the chain may also comprise non-carbon atoms such as nitrogen, oxygen and sulphur.

It is also noted that the bonds forming the chain of atoms extending between the carbon alpha to the leader group and the M substituent may be saturated, partially unsaturated, or fully unsaturated. For example, the leader group may comprise as part of the chain of atoms one or more alkene (—CH=CH—) or alkyne (—C≡C—) bonds.

The atoms forming the backbone of the leader group, L, may optionally comprise one or more members of the group consisting of: —$(CH_2)n$,—where n is an integer from 1 to 10; —$CH(CH_3)$—; —$CH(CH_3)CH_2$— and —$CH_2CH(CH_3)$—; —$CH(CH_3)CH_2CH_2$—, —$CH_2CH(CH_3)CH_2$—, and —$CH_2CH_2CH$ ($CH_3$)—; —$CH(CH_3)CH_2CH_2CH_2$—, —$CH_2CH(CH_3)CH_2CH_2$—, —$CH_2CH_2CH(CH_3)CH_2$—, and —$CH_2CH_2CH_2CH(CH_3)$—; —$CH(CH_3)CH_2CH_2CHCH_2$—, —$CH_2CH(CH_3)CH_2CH_2CH_2$—, —$CH_2CH_2CH(CH_3)CH_2CH_2$—, —$CH_2CH_2CH_2CH(CH_3)CH_2$—, and —$CH_2CH_2CH_2CH_2CH(CH_3)$—; —$CH(CH_2CH_3)$—; —$CH(CH_2CH_3)CH_2$— and —$CH_2CH(CH_2CH_3)$—; —$CH(CH_2CH_3)CH_2CH_2$—, —$CH_2CH(CH_2CH_3)CH_2$—, and —$CH_2CH_2CH(CH_2CH_3)$—; —$CH(CH_2CH_3)CH_2CH_2CH_2$—, —$CH_2CH(CH_2CH_3)CH_2CH_2$—, —$CH_2CH_2CH(CH_2CH_3)CH_2$—, and —$CH_2CH_2CH_2CH(CH_2CH_3)$—; —$CH_2CH_2CH(CH_2CH_3)CH_2$—, —$CH_2CH_2CH_2CH(CH_2CH_3)CH_2$—, and —$CH(CH_2CH_3)CH_2CH_2CH_2CH_2$—, —$CH_2CH(CH_2CH_3)CH_2CH_2CH_2$—, —$CH_2CH_2CH_2CHCH(CH_2CH_3)$; —CH=CH—; —CH=$CHCH_2$— and —$CH_2CH$=CH—; —CH=$CHCHCH_2$—, —$CH_2CH$=$CHCH_2$—, and —$CH_2CH_2CH$=CH—; —CH=$CHCH_2CH_2CH_2$—, —$CH_2CH$=$CHCH_2CH_2$—, —$CH_2CH_2CH$=$CHCH_2$—, and —$CH_2CH_2CH_2CH$=CH—; —CH=$CHCHCH_2CH_2CH_2$—, —$CH_2CH$=$CHCH_2CH_2CH_2$—, —$CH_2CH_2CH$=$CHCH_2CH_2$—, —$CH_2CH_2CH_2CH$=$CHCH_2$—, and —CH₂CH₂CH₂CHCH═CH—; —C(CH₃)═CH— and —CH═C(CH₃)—; —C(CH₃)═CHCH₂—, —CH═C(CH₃)CH₂—, and —CH═CHCH(CH₃)—; —CH(CH₃)CH═CH—, —CH₂C(CH₃)═CH—, and —CH₂CH═C(CH₃)—; —CH═CHCH═CH—; —CH═CHCH═CHCH₂—, —CH₂CH═CHCH═CH—, and —CH═CHCH₂CH═CH—; —CH═CHCH═CHCH₂CH₂—, —CH═CHCH₂CH═CHCH₂—, and —CH═CHCH₂CH₂CH═CH—, —CH₂CH═CHCH═CHCH₂—, —CH₂CH═CHCH₂CH═CH—, and —CH₂CH₂CH═CHCH═CH—; —C(CH₃)═CHCH═CH—, —CH═C(CH₃)CH═CH—, —CH═CHC(CH₃)═CH—, and —CH═CHCH═C(CH₃)—; —C≡C—; —C≡CCH₂—, —CH₂C≡C—; —C≡CCH(CH₃)—, and —CH(CH₃)C≡C—; —C≡CCH₂CH₂—, —CH₂C—CCH₂—, and —CH₂CH₂C≡C—; —C≡CCH(CH₃)CH₂— and —C≡CCH₂CH(CH₃)—; —CH(CH₃)C≡CCH₂— and —CH₂C≡CCH(CH₃)—; —CH₂C≡CCH(CH₃)—; —CH(CH₃)CH₂C≡C— and —CH₂CH(CH₃)C≡C—; —C≡CCH═CH—, —CH═CHC≡C—, and —C≡CC≡C—; —C≡CCH₂CH₂CH₂— and —CH₂CH₂CH₂C≡C—; —C≡CCH₂CH₂CH₂CH₂— and —CH₂CH₂CH₂CH₂C≡C—; —C≡CCH═CHCH═CH—, —CH═CHC≡C— CH═CH—, and —CH═CHCH═CHC≡C—; —C(CH₃) ═CHC≡C—, —CH═C(CH₃)C≡C—, —C≡CC(CH₃) ═CH—, and —C≡CCH═C(CH₃)—. It is noted that the hydrogen atoms of above possible portions of the leader group may optionally be substituted with further substituents.

It is also noted that the leader group may comprise one or more substituents extending from one or more atoms of the leader group backbone. In one variation, two substituents extending from the atoms extending between the carbon alpha to the leader group and the M substituent to form one or more three, four, five, six, seven, eight or nine membered rings. The atoms of the leader group forming the ring may be separated from each other by 0, 1, 2, 3, or 4 atoms.

The rings may be saturated or partially unsaturated (i.e., comprise one or two double bonds). The rings may also be aromatic, referred to herein as aryl and heteroaryl rings. The rings may optionally be further substituted. These further ring substituents may combine to form additional rings that are fused to the rings forming a portion of the backbone, e.g., bicycloaryl and bicycloheteroaryl.

Examples of cycloalkyl rings that may be formed by one or more leader group backbone atoms include, but are not limited to: cyclopropyl, cyclohexane, cyclopentane, cyclopentene, cyclopentadiene, cyclohexane, cyclohexene, cyclohexadiene, phenyl, cycloheptane, cycloheptene, cycloheptadiene, cyclooctane, cyclooctene, and cyclooctadiene.

Examples of aryl rings that may be formed by one or more leader group backbone atoms include, but are not limited to: phenyl, biphenyl-2-yl, 2-bromophenyl, 2-bromocarbonylphenyl, 2-bromo-5-fluorophenyl, 4-tert-butylphenyl, 4-carbamoylphenyl, 4-carboxy-2-nitrophenyl, 2-chlorophenyl, 4-chlorophenyl, 3-chlorocarbonylphenyl, 4-chlorocarbonylphenyl, 2-chloro-4-fluorophenyl, 2-chloro-6-fluorophenyl, 4-chloro-2-nitrophenyl, 6-chloro-2-nitrophenyl, 2,6-dibromophenyl, 2,3-dichlorophenyl, 2,5-dichlorophenyl, 3,4-dichlorophenyl, 2-difluoromethoxyphenyl, 3,5-dimethylphenyl, 2-ethoxycarbonylphenyl, 2-fluorophenyl, 2-iodophenyl, 4-isopropylphenyl, 2-methoxyphenyl, 4-methoxyphenyl, 2-methylphenyl, 3-methylphenyl, 4-methylphenyl, 5-methyl-2-nitrophenyl, 4-methylsulfonylphenyl, naphth-2-yl, 2-nitrophenyl, 3-nitrophenyl, 4-nitrophenyl, 2,3,4,5,6-pentafluorophenyl, phenyl, 2-trifluoromethoxyphenyl, 3-trifluoromethoxyphenyl, 4-trifluoromethoxyphenyl, 2-trifluoromethylphenyl, 3-trifluoromethylphenyl, 4-trifluoromethylphenyl, 2-trifluoromethylsulfanylphenyl, 4-trifluoromethylsulfanylphenyl, and the like.

Examples of heteroaryl rings that may be formed by one or more leader group backbone atoms include, but are not limited to: furan. thiofuran, pyrrole, isopyrrole, 3-isopyrrole, pyrazole, isoimidazole, triazole, isoxazole, oxazole, thiazole, isothiazole, oxadiazole, oxatriazole, pyridine, pyridazine, pyrimidine, pyrazine, triazine, benzofuran, isobenzofuran, benzothiofuran, isobenzothiofuran, indole, isobenzazole, quinoline, isoquinoline, cinnoline, quinazoline, naphthyridine, and pyridopyridine Particular examples of heteroaryl rings that may be formed by one or more leader group backbone atoms include, but are not limited to: 4-amino-2-hydroxypyrimidin-5-yl, dibenzofuranyl, benzothiazol-2-yl, 1H-benzoimidazol-2-yl, 2-bromopyrid-5-yl, 5-bromopyrid-2-yl, 4-carbamoylthiazol-2-yl, 3-carboxypyrid-4-yl, 5-carboxy-2,6-dimethylpyrid-3-yl, 3,5-dimethylisoxazol-4-yl, 5-ethoxy-2,6-dimethylpyrid-3-yl, 5-fluoro-6-hydroxypyrimidin-4-yl, fur-2-yl, fur-3-yl, 5-hydroxy-4,6-dimethylpyrid-3-yl, 8-hydroxy-5,7-dimethylquinolin-2-yl, 5-hydroxymethylisoxazol-3-yl, 3-hydroxy-6-methylpyrid-2-yl, 3-hydroxypyrid-2-yl, 1H-imidazol-2-yl, 1H-imidazol-4-yl, 1H-indol-3-yl, isothiazol-4-yl, isoxazol-4-yl, 2-methylfur-3-yl, 5-methylfur-2-yl, 1-methyl-1H-imidazol-2-yl, 5-methyl-3H-imidazol-4-yl, 5-methylisoxazol-3-yl, 5-methyl-2H-pyrazol-3-yl, 3-methylpyrid-2-yl, 4-methylpyrid-2-yl, 5-methylpyrid-2-yl, 6-methylpyrid-2-yl, 2-methylpyrid-3-yl, 2-methylthiazol-4-yl, 5-nitropyrid-2-yl, 2H-pyrazol-3-yl, 3H-pyrazol-4-yl, pyridazin-3-yl, pyrid-2-yl, pyrid-3-yl, pyrid-4-yl, 5-pyrid-3-yl-2H-[1,2,4]triazol-3-yl, pyrimidin-4-yl, pyrimidin-5-yl, 1H-pyrrol-3-yl, quinolin-2-yl, 1H-tetrazol-5-yl, thiazol-2-yl, thiazol-5-yl, thien-2-yl, thien-3-yl, 2H-[1,2,4]triazol-3-yl, 3H-[1,2,3]triazol-4-yl, 5-trifluoromethylpyrid-2-yl, and the like. Suitable protecting groups include tert-butoxycarbonyl, benzyloxycarbonyl, benzyl, 4-methoxybenzyl, 2-nitrobenzyl, and the like.

In one particular variation, the ring formed by the backbone of the leader group is a six membered ring, such as a phenyl ring. Examples of such leader groups include meta and para cinnamate. In one embodiment where the leader group is cinnamate, HDAC inhibitors of the present invention are provided that comprise the formula

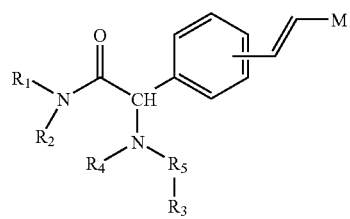

wherein the alkene is attached to the ring at the meta or para position. It is noted that the other substituents may be as otherwise described herein. For example, in one variation, the HDAC inhibitors have the formula

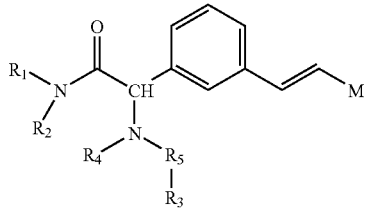

and in another variation has the formula

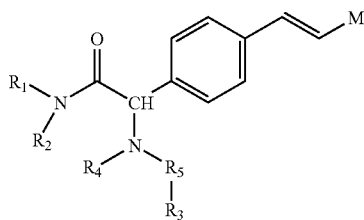

where the other substituents may be as otherwise described herein.

In another particular variation, the ring comprises heteroatoms. Examples of such rings comprising heteroatoms, including 5 and 6 membered aromatic rings comprising heteroatoms are illustrated in FIG. 2C. Optionally, the chain atoms of the leader group are meta or para substituents of the heteroaryl ring. For example, the heteroaryl ring optionally has the formula

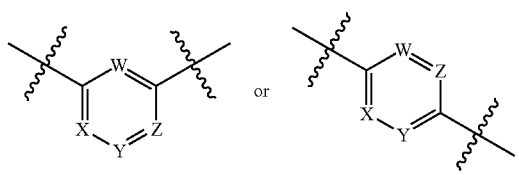

where W, X, Y, and Z are each independently N or CH, with a proviso that when X and Z are both N, then Y is CH.

In one variation where the leader group comprises the above heteroaryl rings and an alkene, HDAC inhibitors of the present invention are provided that comprise the formula

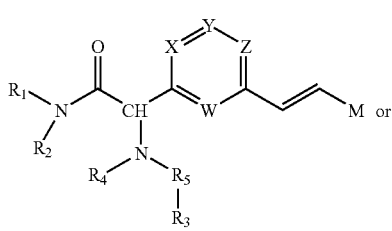

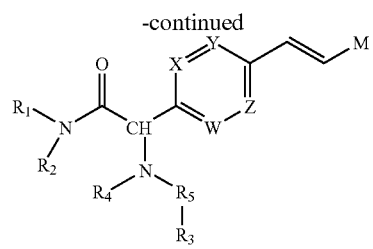

where W, X, Y, and Z are each independently N or CH, with a proviso that when X and Z are both N, then Y is CH; and where the other substituents may be as otherwise described herein.

Further examples of leader groups that may optionally be used are shown in the examples.

It is noted that the carbon alpha to the leader group is a chiral center. The chiral center may be either the R or S enantiomer, it being noted that the preferred handedness depending on the substituents.

Synthetic scheme for synthesizing compounds according to these embodiments are provided in the Examples. Particular examples of HDAC inhibitors according to these embodiments are provided in the examples.

A. Salts, Hydrates, and Prodrugs of HDAC Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl- and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, benzenesulfonate (besylate), bisulfate, bisulfite, bromide, byturate, camphorate, camphorsulfonate, caprylate, chloride, chlorobenzoate, cyclopentanepropionate, digluconate, dihydrogenphosphate, dinitrobenzoate, dodecylsulfate, ethanesulfonate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free acid forms will typically differ from their respective salt forms somewhat in physical properties such as solubility in polar solvents, but otherwise the salts are equivalent to their respective free acid forms for the purposes of the present invention.

When the compounds of the present invention possess a free base form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free base forms will typically differ from their respective salt forms somewhat in physical properties such as solubility in polar solvents, but otherwise the salts are equivalent to their respective free base forms for the purposes of the present invention.

Compounds of the present invention, which comprise basic nitrogen-containing groups, may be quaternized with such agents as ($C_{1-4}$) alkyl halides, e.g., methyl, ethyl, iso-propyl and tert-butyl chlorides, bromides and iodides; di ($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al.(1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, *Protecting Groups in Organic Synthesis*, $3^{rd}$ edition, John Wiley & Sons, Inc. 1999.

Compounds of the present invention may also be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid adsorption of the compound.

3. Preparation of HDAC Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

4. Indications for Use of HDAC Inhibitors

HDAC is believed to contribute to the pathology and/or symptomology of several different diseases such that reduction of the activity of HDAC in a subject through inhibition may be used to therapeutically address these disease states. Examples of various diseases that may be treated using the HDAC inhibitors of the present invention are described herein. It is noted that additional diseases beyond those disclosed herein may be later identified as the biological roles that HDAC play in various pathways becomes more fully understood.

A. Undesirable or Uncontrolled Cell Proliferation

One set of indications that HDAC inhibitors of the present invention may be used to treat are those involving undesirable or uncontrolled cell proliferation. Such indications include benign tumors, various types of cancers such as primary tumors and tumor metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukemia, multiple myeloma, bladder carcinoma, renal carcinoma, breast carcinoma, colorectal carcinoma, neuroblastoma and melaoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,1-3,4-dehydroproline, thiaproline], beta.-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-(2-carboxyphenyl-4-chloroanthronilic acid disodium or "CCA", thalidomide; angostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumors retain their differentiated features and do not divide in a completely uncontrolled manner. A benign tumor is usually localized and nonmetastatic. Specific types of benign tumors that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumors, or metastases, are tumors that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using the HDAC inhibitors of the present invention include, but are not limited to, leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomymater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome. An example of a cell proliferative disorder that may be treated using the invention is a bone tumor.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidois, and rhematoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifectations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidois, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angionesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation and provide the RA patient relief from the symptoms.

5. Compositions Comprising HDAC Inhibitors

A wide variety of compositions and administration methods may be used in conjunction with the HDAC inhibitors of the present invention. Such compositions may include, in addition to the HDAC inhibitors of the present invention, conventional pharmaceutical excipients, and other conventional, pharmaceutically inactive agents. Additionally, the compositions may include active agents in addition to the HDAC inhibitors of the present invention. These additional active agents may include additional compounds according to the invention, or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising HDAC inhibitors of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The HDAC inhibitors and compositions comprising them may be administered or coadministered in any conventional dosage form. Coadministration in the context of this invention is intended to mean the administration of more than one therapeutic agents, one of which includes a HDAC inhibitor, in the course of a coordinated treatment to achieve an improved clinical outcome. Such coadministration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When HDAC inhibitors according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding HDAC inhibitors according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more HDAC inhibitors according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of a HDAC inhibitor of the present invention to reduce HDAC activity in vivo, thereby treating the disease state of the subject.

Dosage forms or compositions may optionally comprise one or more HDAC inhibitors according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more HDAC inhibitors, optionally 0.1-95%, and optionally 1-95%.

Salts, preferably sodium salts, of the HDAC inhibitors may be prepared with carriers that protect the compound against rapid elimination from the body, such as time release formulations or coatings. The formulations may further include other active compounds to obtain desired combinations of properties.

A. Formulations For Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, HDAC inhibitors according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene laural ether.

Examples of emetic-coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The HDAC inhibitors of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising HDAC inhibitors of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic adds and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, eg., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

B. Injectables, Solutions and Emulsions

The present invention is also directed to compositions designed to administer the HDAC inhibitors of the present invention by parenteral administration, generally characterized by injection, either subcutaneously, intramuscularly or intravenously. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Example of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcelluose, hydroxypropyl methylcellulose and polyvinylpyrrolidone.

Examples of emulsifying agents that may be used include Polysorbate 80 (Tween 80). A sequestering or chelating agent of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of a HDAC inhibitor in the parenteral formulation may be adjusted so that an injection administers a pharmaceutically effective amount sufficient to produce the desired pharmacological effect. The exact concentration of a HDAC inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the HDAC inhibitor to the treated tissue(s). The HDAC inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The HDAC inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Lyophilized Powders

The HDAC inhibitors of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the sodium salt in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a HDAC inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the HDAC inhibitor.

D. Topical Administration

The HDAC inhibitors of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The HDAC inhibitors may be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically diameters of less than 50 microns, preferably less than 10 microns.

The HDAC inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the HDAC inhibitor alone or in combination with other pharmaceutically acceptable excipients can also be administered.

E. Formulations for Other Routes of Administration

Depending upon the disease state being treated, other routes of administration, such as topical application, transdermal patches, a rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of the Present Invention | 1% |
| Microcrystalline Cellulose | 73% |
| Stearic Acid | 25% |
| Colloidal Silica | 1%. |

6. Kits Comprising HDAC Inhibitors

The invention is also directed to kits and other articles of manufacture for treating diseases associated with HDAC. It is noted that diseases are intended to cover all conditions for which the HDAC possesses activity that contributes to the pathology and/or symptomology of the condition.

In one embodiment, a kit is provided that comprises a composition comprising at least one HDAC inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one HDAC inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

7. Combination Therapy

A wide variety therapeutic agents may have a therapeutic additive or synergistic effect with HDAC inhibitors according to the present invention. Such therapeutic agents may additively or synergistically combine with the HDAC inhibitors to inhibit undesirable cell growth, such as inappropriate cell growth resulting in undesirable benign conditions or tumor growth.

In one embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of therapeutic agents that may be used in combination with HDAC inhibitors include, but are not limited to, alkylating agents, antibiotic agents, antimetabolic agents, hormonal agents, plant-derived agents, and biologic agents.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including a HDAC inhibitor and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interferes with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including a HDAC INHIBITOR and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a HDAC INHIBITOR and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including a HDAC INHIBITOR and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a HDAC INHIBITOR and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a HDAC INHIBITOR and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with HDAC INHIBITOR include, but are not limited to, interleukin 2 (IL-2), and interleukin 4 (IL-4), interleukin 12 (IL-12).

Interferon include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with a HDAC INHIBITOR include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with a HDAC INHIBITOR to reduce chemotherapy-induced myelopoietic toxicity.

Other immuno-modulating agents other than cytokines may also be used in conjunction with a HDAC INHIBITOR to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including HDAC INHIBITOR and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20$^+$ pre-B and mature B cells. RITUXAN® is used as single agent for the treatment of patients with relapsed or refractory low-grade or follicular, CD20$^+$, B cell non-Hodgkin's lymphoma. Combination therapy including HDAC INHIBITOR and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutions in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including a HDAC INHIBITOR and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), α-fetoprotein (AFP), carcinoembryonic antigen (CEA) (produced by colon cancers and other adenocarcinomas, e.g. breast, lung, gastric, and pancreas cancers), melanoma associated antigens (MART-1, gp 100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

EXAMPLES

1. Ugi Reaction Based Synthetic Schemes for HDAC Inhibitors

One advantage of HDAC inhibitors according to the present invention is that they may be readily synthesized by an Ugi reaction. In general, an Ugi reaction involves four subcomponents, namely an amide ($R_{amide}NH_2$), an acid ($R_{acid}CO_2H$), an aldehyde ($R_{aldehyde}CHO$) and an isocyanide ($R_{isocyanine}NC$) which come together to form the below reaction product

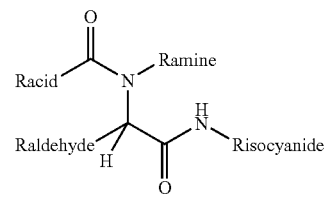

Illustrated below are different reaction schemes for generating HDAC inhibitors according to the present invention via an Ugi reaction. Schemes 1 and 2 (below) illustrate how different linker groups may be integrated into the inhibitors by using different aldehydes in the reaction scheme.

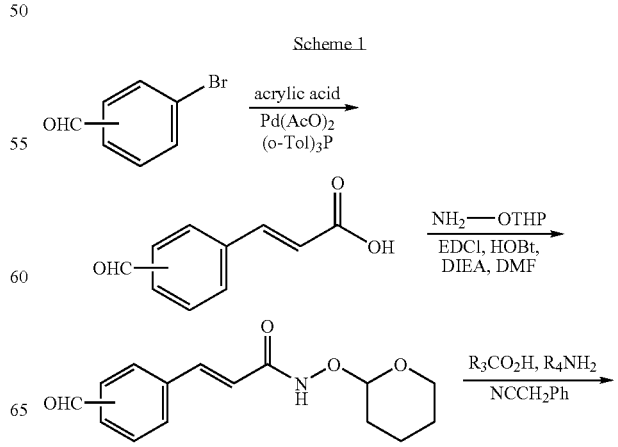

Scheme 1

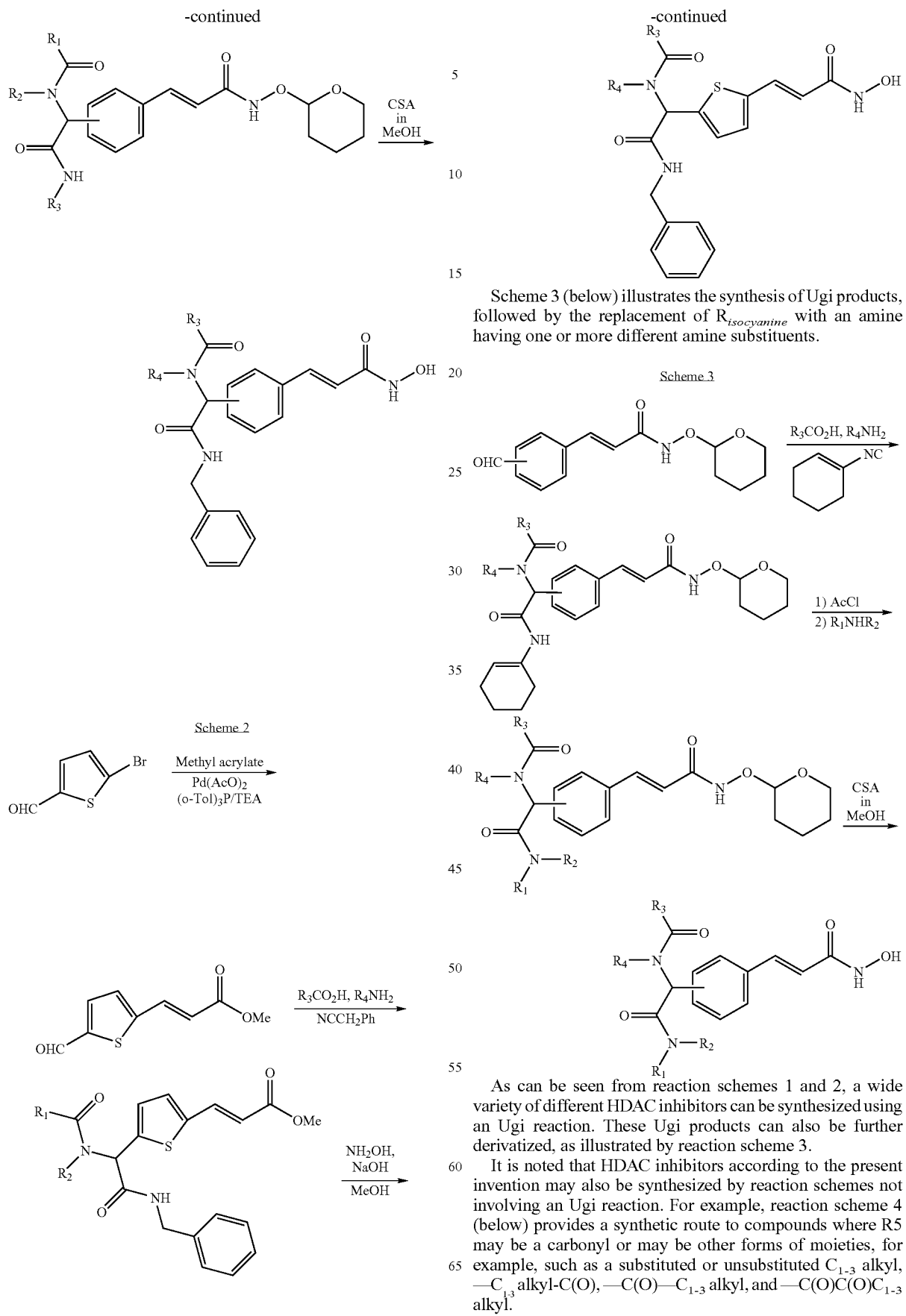

Scheme 3 (below) illustrates the synthesis of Ugi products, followed by the replacement of $R_{isocyanine}$ with an amine having one or more different amine substituents.

As can be seen from reaction schemes 1 and 2, a wide variety of different HDAC inhibitors can be synthesized using an Ugi reaction. These Ugi products can also be further derivatized, as illustrated by reaction scheme 3.

It is noted that HDAC inhibitors according to the present invention may also be synthesized by reaction schemes not involving an Ugi reaction. For example, reaction scheme 4 (below) provides a synthetic route to compounds where R5 may be a carbonyl or may be other forms of moieties, for example, such as a substituted or unsubstituted $C_{1-3}$ alkyl, —$C_{1-3}$alkyl-C(O), —C(O)—$C_{1-3}$ alkyl, and —C(O)C(O)$C_{1-3}$ alkyl.

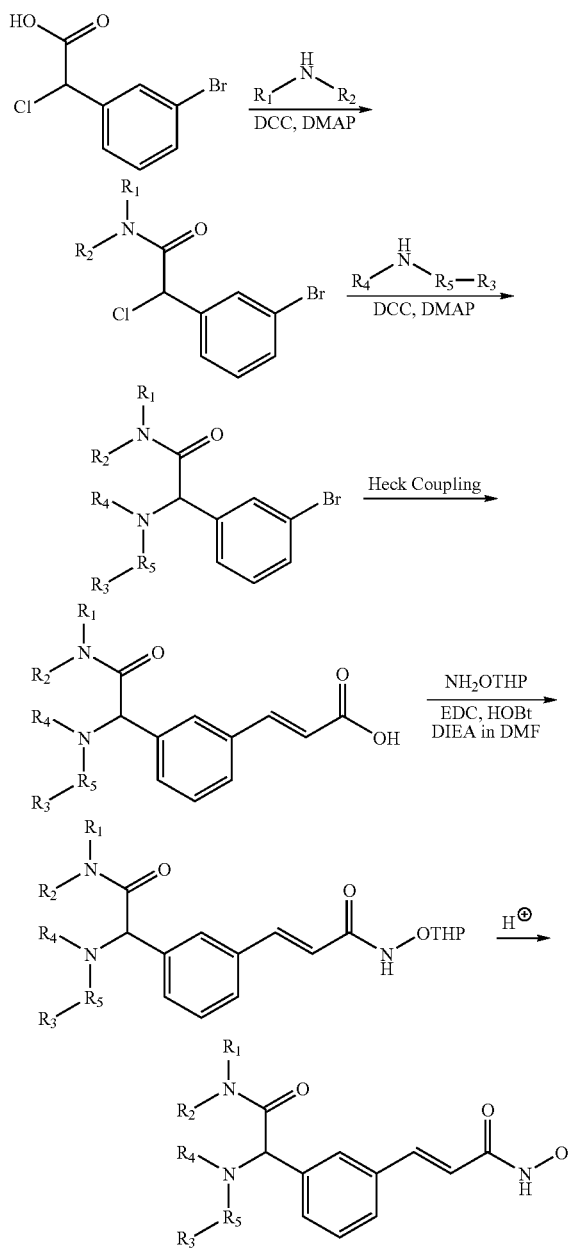

2. Synthesis of a Library of HDAC Inhibitors

In order to rapidly assess the activity of different inhibitors according to the present invention, a library of compounds were synthesized according to reaction scheme 1. More specifically, 3-(3-formyl-phenyl)-N-(tetrahydro-pyran-2-yloxy)-acrylamide and 3-(4-formyl-phenyl)-N-(tetrahydro-pyran-2-yloxy)-acrylamide were prepared by taking the corresponding acrylic acids (10 mMol) and dissolving them in 20 ml dry DMF and treated with HOBt (1.35 g, 10 mMol) for 30 minutes. EDCI (1.91 g, 10 mMol), $H_2NOTHP$ (1.17 g, 10 mMol) and 2 ml of DIEA were then added to the mixture. After three hours of stirring at room temperature, DMF was removed under reduced pressure. The residue was then extracted with ethyl acetate and water. The desired aldehyde acrylamides were obtained after purification on silica gel chromatographically. These aldehyde acrylamides were then used in an Ugi reaction. Specifically, to a 0.5 M solution of 3-(3-formyl-phenyl)-N-(tetrahydro-pyran-2-yloxy)-acrylamide or 3-(4-formyl-phenyl)-N-(tetrahydro-pyran-2-yloxy)-acrylamide in MeOH (methanol)/THF (tetrahydrofuran) (150 μL, 1:1) was added sequentially a 1.0 M solution of amine (75 μL in MeOH), a 1.0 M solution of carboxylic acid (75 μL in MeOH), and a 1.0 M solution of benzylisocyanide (75 μL in MeOH). The reaction was stirred for 48 hrs at ambient temperature, treated with a 1.1 M solution of 10-camphorsulfonic acid (75 μL in MeOH), stirred for an additional 2 hrs at ambient temperature, and then purified by LCMS without further work-up.

A variety of different carboxylic acid and amine compounds were used in the above described Ugi reaction to form the library including those carboxylic acid and amine compounds shown below in Tables 1 and 2. Benzylisocyanide was used as the isocyanide compound in the reaction scheme. FIGS. 5A and 5B provide examples of compounds that were synthesized as described in example 2.

TABLE 1

| | |
|---|---|
| Formic acid | 4-biphenylcarboxylic acid |
| acetic acid | 3-nitrocinnamic acid |
| butyric acid | hydrocinnamic acid |
| cyclohexane carboxylic acid | phenylacetic acid |
| 3-methoxypropionic acid | Ac-D-Pro-OH |
| 2,4-hexadienoic acid | Ac-L-Pro-OH |
| benzoic acid | Ac-D-Phe-OH |
| o-toluic acid | Ac-L-Phe-OH |
| m-toluic acid | Ac-D-Trp-OH |
| p-toluic acid | Ac-L-Trp-OH |
| trifluoro-o-toluic | 2-furoic acid |
| trifluoro-m-toluic | 3-furoic acid |
| trifluoro-p-toluic | furylacrylic acid |
| o-anisic acid | 2-benzofurancarboxylic acid |
| m-anisic acid | 1-methyl-2-pyrrolecarboxylic acid |
| p-anisic acid | 4-(1H-pyrrol-1-yl)benzoic acid |
| 2-bromobenzoic acid | 2-hydroxy-5-(1H-pyrrol-1-yl)benzoic acid |
| 3-bromobenzoic acid | 2,6-dimethoxynicotinic acid |
| 4-bromobenzoic acid | isonicotinic acid |
| 2-hydroxybenzoic acid | nicotinic acid |
| 3-hydroxybenzoic acid | 2-chloromandelic acid |
| 4-hydroxybenzoic acid | quinaldic acid |
| 2-phenoxybenzoic acid | 5-methoxyindole-2-carboxylic acid |
| 3-phenoxybenzoic acid | suberic acid monomethyl ester |
| 4-phenoxybenzoic acid | 4-nitro-3-pyrazolecarboxylic acid |
| 3-dimethylamino benzoic acid | 4-imidazoleacrylic acid |
| 4-dimethylamino benzoic acid | (2-pyrimidylthio)acetic acid |
| 3-cyanobenzoic acid | 5-methylpyrazole-3-carboxylic acid |
| 4-cyanobenzoic acid | 3-hydroxy-2-quinoxalinecarboxylic acid |
| 1-naphthoic acid | 2-pyrazinecarboxylic acid |
| 2-naphthoic acid | |

TABLE 2

| | |
|---|---|
| Methylamine | m-Anisidine |
| Isopropylamine | p-Anisidine |
| Ethylamine | 1-Aminoindan |
| 3-Phenyl-1-propylamine | n-Phenyl-1,2-phenylenediamine |
| Cyclopentylamine | n-Phenyl-1,4-phenylenediamine |
| Isoamylamine | 3-(aminomethyl)pyridine |

TABLE 2-continued

| | |
|---|---|
| R-(+)-a-methylbenzylamine | 4-(aminomethyl)pyridine |
| S-(+)-a-methylbenzylamine | 3,4-Dimethoxy-phenethylamine |
| 4-Methoxybenzylamine | Phenethylamine |
| 3-Methoxybenzylamine | 3-Aminopyrazole |
| 4-Aminobenzylamine | Aniline |
| 2-Benzylaniline | 3-Benzyloxyaniline |
| p-Toluidine | 4-Benzyloxyaniline |
| 4-Phenoxyaniline | 2-Aminobenzanilide |
| 3-Phenoxyaniline | 3-Nitrobenzylamine |
| 3-Phenylbenzylamine | 4-Nitrobenzylamine |
| 2-Phenylbenzylamine | m-Nitroaniline |
| 3-Aminobenzonitrile | 4-Nitroaniline |
| 4-Aminobenzonitrile | 3-Chlorobenzylamine |
| 2-Aminopyridine | 4-Chlorobenzylamine |
| 3-Aminopyridine | 2-Chloroaniline |
| 4-Aminopyridine | 3-Chloroaniline |
| 2,2-Diphenylethylamine | 4-Chloroaniline |
| 4-Aminobiphenyl | L-Phenylalaninol |
| 1-AminoNaphthalene | D-Phenylalaninol |
| 1-Naphthalene-methylamine | Tryptamine |
| 5-Phenyl-o-anisidine | Tyramine |
| Cyclohexylamine | 1-(2-Aminoethyl)-pyrrolidine |

3. HDAC8 Activity Assay

The library of compounds formed as described in example 2 were assayed for activity against HDAC8.

Purified HDAC8 was obtained as follows. Residues 1-377 of SEQ ID NO: 1 which correspond to the entire sequence of human HDAC8 was amplified by PCR and cloned into the SmaI/HinDIII site of pFastbac (Invitrogen) with a 6-histidine tag at the N-terminus. This DNA sequence is presented in FIG. 3 as SEQ ID NO:2. Expression in this vector generated a fusion of HDAC8 residues 1-377 with an N-terminal 6x-histidine tag, the amino acid sequence of which is shown in FIG. 4 as SEQ ID NO:3. As a separate part of the disclosure, the amino acid and nucleotide sequences of FIGS. 3 and 4 and associated information are also disclosed in paper form using symbols and format in accordance with the rules of patent practice. This listing of the sequences ("Sequence Listing") in hereby incorporated by reference in its entirety.

Recombinant baculovirus incorporating the HDAC8 construct was generated by transposition using the Bac-to-Bac system (Invitrogen). High-titer viral stocks were generated by infection of *Spodoptera frugiperda* Sf9 cells and the expression of recombinant protein was carried out by infection of *Trichoplusia ni* Hi5 cells (Invitrogen) in 10 L Wave Bioreactors (Wave Biotech).

Recombinant protein was isolated from cellular extracts by passage over ProBond (InVitrogen) resin. Partially purified extracts were further purified by high pressure liquid chromatography over a BioSep S3000 gel filtration resin. HDAC8 protein purity, as determined on denaturing SDS-PAGE gel, was 90-95%. HDAC8 was concentrated to a final concentration of 15 mg/ml and stored at 4° C. in a buffer containing 25 mM TRIS-HCl pH 7.6, 150 mM NaCl, 1 mM EDTA and 0.25 mM TCEP.

The inhibitory properties of compounds relative to HDAC8 were determined using a white or black 384-well-plate format under the following reaction conditions: 25 mM Tris pH 8.0, 100 mM NaCl, 50 mM KCl, 0.1 mM EDTA, 0.01% Brij35, 0.1 mM TCEP. 50 uM tBoc-Lys(Ac)-AMC, 2% DMSO. Reaction product was determined quantitatively by fluorescence intensity using a Fluorescence plate reader (Molecular Devices Gemini) with an excitation wavelength at 370 nm and emission at 480 nm (for white plates) or 465 nm (for black plates).

The assay reaction was initiated as follows: 5 ul of 150 uM tBoc-Lys(Ac)AMC was added to each well of the plate, followed by the addition of 5 ul of inhibitor (2 fold serial dilutions for 11 data points for each inhibitor) containing 6% DMSO. 5 ul of HDAC8 solution was added to initiate the reaction (final enzyme concentration was 10 nM for HDAC8). The reaction mixture was then incubated at room temperature for 60 min, and quenched and developed by addition of 5 ul of 10 mM phenanthroline and 4 mg/ml trypsin (final concentration of phenanthroline is 2.5 mM, and trypsin is 1 mg/ml). Fluorescence intensities of the resulting reaction mixtures were measured after a 30 minute incubation at room temperature.

IC50 values were calculated by non-linear curve fitting of the compound concentrations and fluorescence intensities to the standard IC50 equation. As a reference point for this assay, suberanilohydroxamic acid (SAHA) showed an IC50 of 130 nM.

FIGS. 5A and 5B indicate which of the compounds produced in the library of example 2 were found to have better than 5 µM activity based on the assay described in this example. Compounds made in the library that were not tested for assay activity are also indicated.

4. Physical Data for Selected HDAC Inhibitors

Provided herein are particular examples of HDAC inhibitors according to the present invention and their associated physical data. It is noted that the invention is not intended to be limited to these compounds. Rather, a wide variety of other compounds according to the present invention having HDAC inhibitory activity may be synthesized by the reaction schemes provided as well as other reaction schemes that may be devised by one of ordinary skill in the art in view of the present teachings.

COMPOUND 1

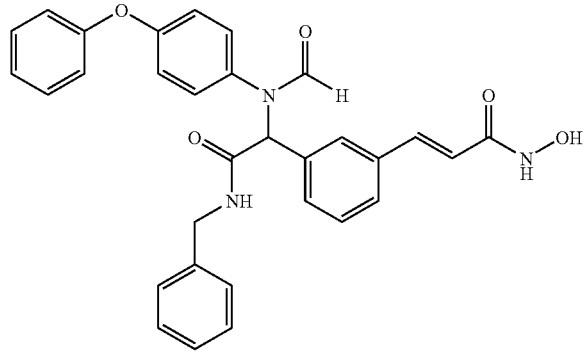

3-(3-{Benzylcarbamoyl-[formyl-(4-phenoxy-phenyl)-amino]-methyl}-phenyl)-N-hydroxy-acrylamide $^1$H-NMR (400 MHz, DMSO-$d_6$): δ 4.40 (m, 2H), 6.13 (s, 1H), 6.35 (dd, 2H), 6.80-7.60 (range, 18H), 8.39 (s, 1H), 8.85 (m, 1H), 9.10 (bs, 1H), 10.80 (bs, 1H). ESI-MS: m/z 520.1 (M-H)$^-$.

COMPOUND 2

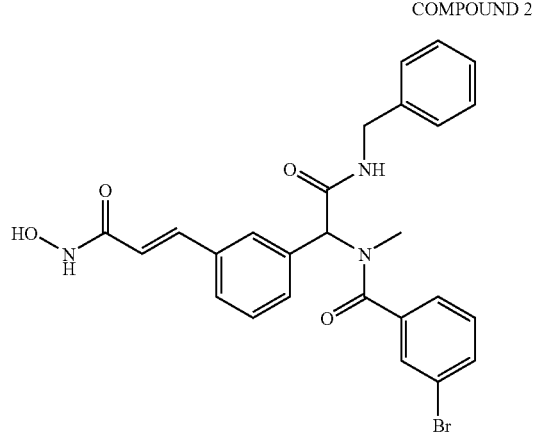

N-{Benzylcarbamoyl-[3-(2-hydroxycarbamoyl-vinyl)-phenyl]-methyl}-3-bromo-N-methyl-benzamide $^1$H NMR (400 MHz, DMSO-d$_6$): δ 2.69 (s, 3H), 4.42 (d, 2H), 6.23 (s, 1H), 6.49 (d, 1H), 7.11-7.83 (band, 14H), 8.83 (br s, 1H), 9.10 (br s, 1H), 10.79 (br s, 1H). ESI-MS: m/z 520.20 (M-H)$^-$.

COMPOUND 3

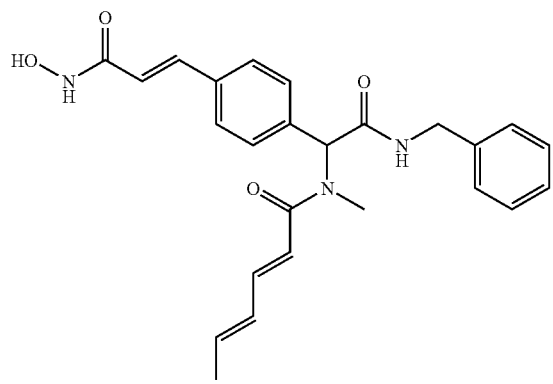

Hexa-2,4-dienoic acid {benzylcarbamoyl-[4-(2-hydroxycarbamoyl-vinyl)-phenyl]-methyl}-methyl-amide $^1$H NMR (400 MHz, DMSO-d$_6$): δ 1.85 (d, 3H), 2.89 (s, 3H), 4.33 (d, 2H), 6.20 (m, 1H), 6.29 (s, 1H), 6.47 (d, 1H), 7.13-7.32 (band, 11H), 7.53 (d, 1H), 7.55 (d, 1H), 8.78 (m, 1H), 9.06 (br s, 1H), 10.80 (br s, 1H). ESI-MS: m/z 432.20 (M-H)$^-$.

COMPOUND 4

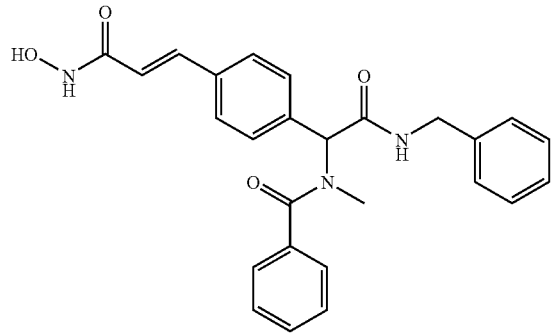

N-{Benzylcarbamoyl-[4-(2-hydroxycarbamoyl-vinyl)-phenyl]-methyl}-N-methyl-benzamide $^1$H NMR (400 MHz, DMSO-d6): δ 2.69 (s, 3H), 4.42 (d, 2H), 6.23 (s, 1H), 6.49 (d, 1H), 7.11-7.71 (band, 15H), 8.83 (br s, 1H), 9.10 (br s, 1H), 10.79 (br s, 1H). ESI-MS: m/z 442.20 (M-H)$^-$.

COMPOUND 5

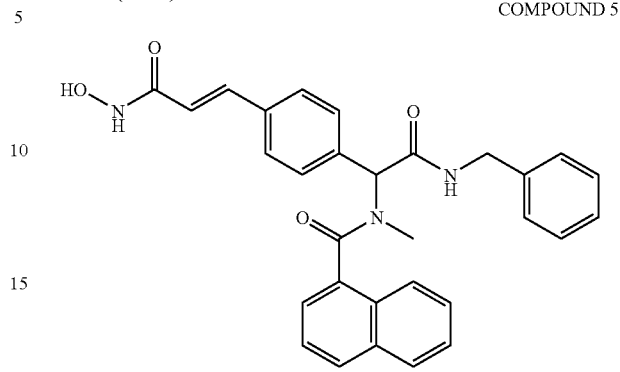

Naphthalene-1-carboxylic acid {benzylcarbamoyl-[4-(2-hydroxycarbamoyl-vinyl)-phenyl]-methyl}-methyl-amide $^1$H NMR (400 MHz, DMSO-d6): δ 2.95 (d, 3H), 4.48 (d, 2H), 6.42 (s, 1H), 6.50 (d, 1H), 7.11-8.09 (band, 17H), 8.93 (br s, 1H), 9.10 (br s, 1H), 10.79 (br s, 1H). ESI-MS: m/z 492.20 (M-H)$^-$.

COMPOUND 6

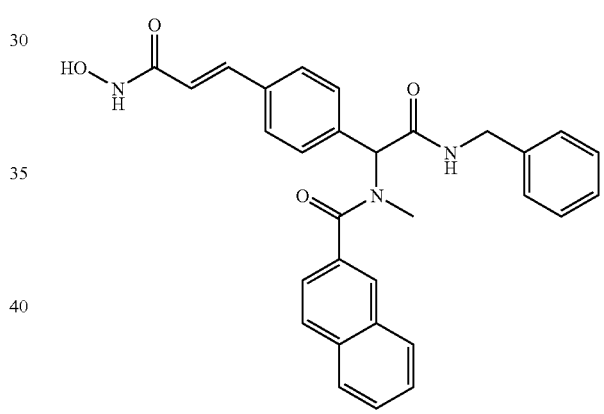

$^1$H NMR (400 MHz, DMSO-d$_6$): δ 2.80 (s, 3H), 4.48 (d, 2H), 6.29 (s, 1H), 6.50 (d, 1H), 7.11-8.09 (band, 17H), 8.90 (br s, 1H), 9.10 (br s, 1H), 10.79 (br s, 1H). ESI-MS: m/z 492.20 (M-H)$^-$.

COMPOUND 7

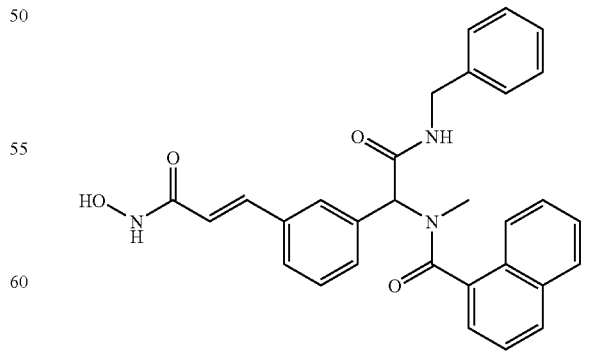

Naphthalene-1-carboxylic acid {benzylcarbamoyl-[3-(2-hydroxycarbamoyl-vinyl)-phenyl]-methyl}-methyl-amide ¹H NMR (400 MHz, DMSO-d₆): δ 2.98 (d, 3H), 4.48 (d, 2H), 6.48 (s, 1H), 6.50 (d, 1H), 7.11-8.09 (band, 17H), 8.93 (br s, 1H), 9.10 (br s, 1H), 10.79 (br s, 1H). ESI-MS: m/z 492.20 (M-H)⁻.

COMPOUND 8

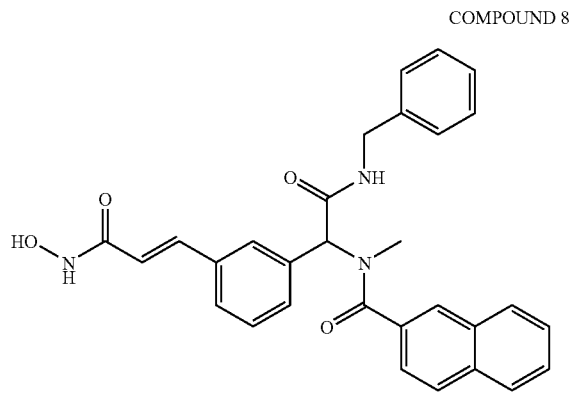

Naphthalene-2-carboxylic acid {benzylcarbamoyl-[3-(2-hydroxycarbamoyl-vinyl)-phenyl]-methyl}-methyl-amide ¹H NMR (400 MHz, DMSO-d₆): δ 2.80 (s, 3H), 4.48 (d, 2H), 6.29 (s, 1H), 6.50 (d, 1H), 7.11-8.05 (band, 17H), 8.90 (br s, 1H), 9.10 (br s, 1H), 10.79 (br s, 1H). ESI-MS: m/z 492.20 (M-H)⁻.

COMPOUND 9

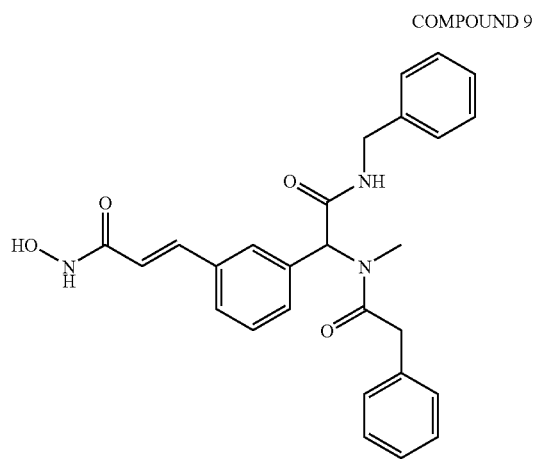

3-{3-[Benzylcarbamoyl-(methyl-phenylacetyl-amino)-methyl]-phenyl}-N-hydroxy-acrylamide ¹H NMR (400 MHz, DMSO-d₆): δ 2.87 (s, 3H), 3.87 (s, 2H), 4.39 (dd, 2H), 6.22 (s, 1H), 6.48 (d, 1H), 7.15-7.69 (band, 15H), 8.79 (m, 1H), 9.10 (br s, 1H), 10.79 (br s, 1H). ESI-MS: m/z 456.20 (M-H)⁻.

COMPOUND 10

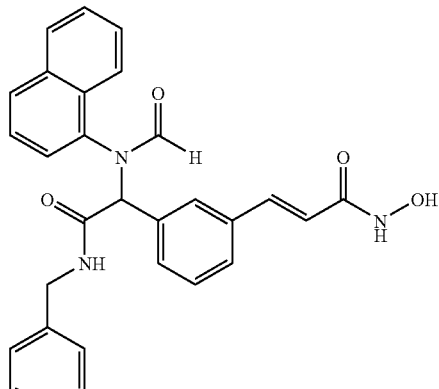

3-{3-[Benzylcarbamoyl-(formyl-naphthalen-1-yl-amino)-methyl]-phenyl}-N-hydroxy-acrylamide ¹H-NMR (400 MHz, DMSO-d₆): δ 4.40 (m, 2H), 6.30 (m, 1H), 6.45 (t, 1H), 6.90-8.10 (range, 17H), 8.75 (s, 1H), 9.10 (bs, 1H), 10.75 (bs, 1H). ESI-MS: m/z 478.1 (M-H)⁻.

COMPOUND 11

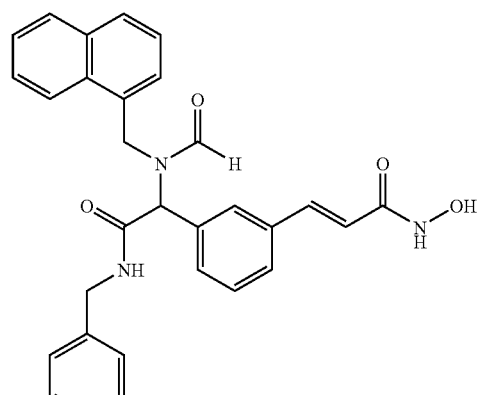

3-{3-[Benzylcarbamoyl-(formyl-naphthalen-1-ylm-ethyl-amino)-methyl]-phenyl}-N-hydroxy-acryla-mide ¹H-NMR (400 MHz, DMSO-d₆): δ 4.30 (m, 2H), 4.70 (d, 1H), 5.20 (m, 2H), 5.40 (d, 1H), 6.05 (s, 1H), 6.35 (dd, 2H), 6.90-8.10 (range, 16H), 8.23 (ss, 1H), 8.85 (m, 1H), 9.10 (bs, 1H), 10.75 (bs, 1H). ESI-MS: m/z 492.1 (M-H)⁻.

COMPOUND 12

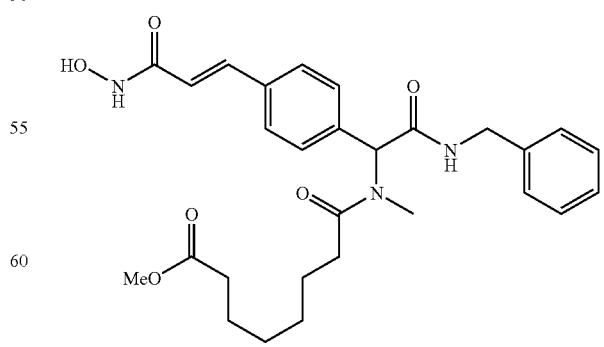

7-({Benzylcarbamoyl-[4-(2-hydroxycarbamoyl-vi-nyl)-phenyl]-methyl}-methyl-carbamoyl)-heptanoic acid methyl ester ¹H NMR (400 MHz, DMSO-d6): δ 1.24 (m 4H), 1.52 (m, 4H), 2.29 (t, 2H), 2.41 (t, 2H), 2.80 (s, 3H), 3.61 (s, 3H), 4.32 (d, 2H), 6.22 (s, 1H), 6.50 (d, 1H), 7.15-7.68 (band, 10H), 8.75 (br s, 1H), 9.10 (br s, 1H), 10.75 (br s, 1H). ESI-MS: m/z 508.20 (M-H)⁻.

COMPOUND 13

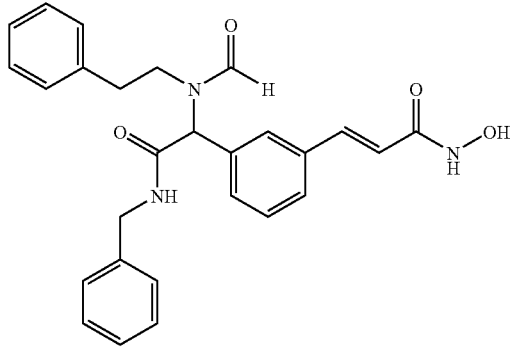

3-{3-[Benzylcarbamoyl-(formyl-phenethyl-amino)-methyl]-phenyl}-N-hydroxy-acrylamide ¹H-NMR (400 MHz, DMSO-d₆): δ 2.20-2.80 (range, 2H), 3.40-3.60 (m, 2H), 4.25-4.50 (m, 2H), 5.45 (s, 1H), 5.95 (s, 1H), 6.50 (t, 1H), 6.85-7.05 (dd, 2H), 6.85-7.05 (range, 13H), 8.10-8.20 (d, 1H), 8.70-8.95 (m,m, 1H), 9.10 (bs, 1H), 10.80 (s, 1H). ESI-MS: m/z 456.1 (M-H)⁻.

COMPOUND 14

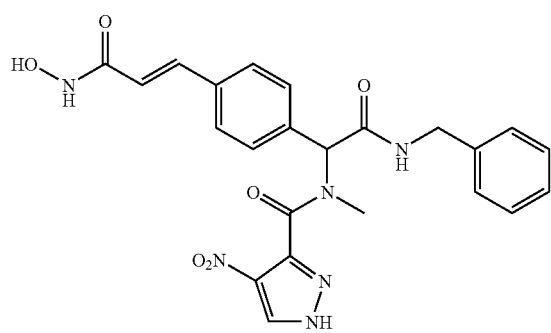

4-Nitro-1H-pyrazole-3-carboxylic acid {benzylcarbamoyl-[4-(2-hydroxycarbamoyl-vinyl)-phenyl]-methyl}-methyl-amide ¹H NMR (400 MHz, DMSO-d₆): δ 2.80 (s, 3H), 3.61 (s, 3H), 4.35 (dd, 2H), 6.42 (s, 1H), 6.50 (dd, 1H), 7.15-7.68 (band, 11H), 8.80 (d, 1H), 9.00 (m, 1H), 10.75 (br s, 1H). ESI-MS: m/z 477.20 (M-H)⁻.

COMPOUND 15

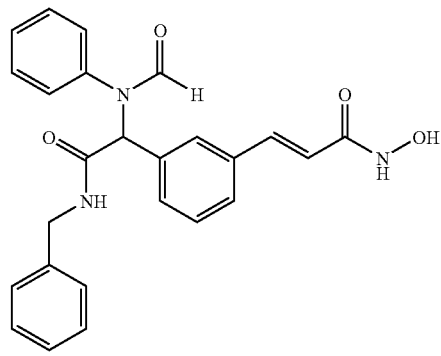

3-{3-[Benzylcarbamoyl-(formyl-phenyl-amino)-methyl]-phenyl}-N-hydroxy-acrylamide ¹H-NMR (400 MHz, DMSO-d₆): δ 4.40 (m, 2H), 6.15 (s, 1H), 6.25-6.55 (dd, 2H), 7.00-7.60 (range, 14H), 8.40 (s, 1H), 8.80-8.95 (s, 1H), 9.10 (bs, 1H), 10.75 (bs, 1H). ESI-MS: m/z 428.0 (M-H)⁻.

COMPOUND 16

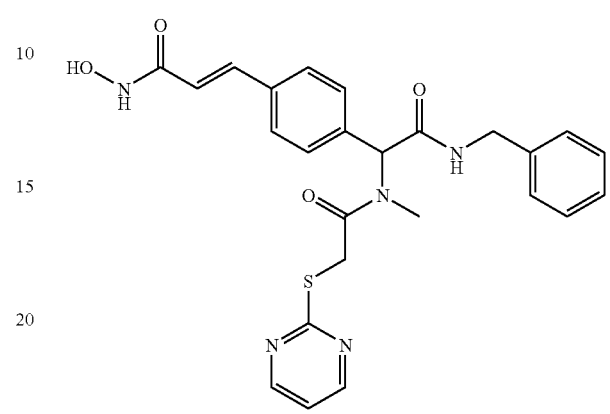

3-[4-(Benzylcarbamoyl-{methyl-[2-(pyrimidin-2-ylsulfanyl)-acetyl]-amino}-methyl)-phenyl]-N-hydroxy-acrylamide ¹H NMR (400 MHz, DMSO-d₆): δ 2.98 (s, 3H), 4.35 (m, 2H), 4.40 (m, 2H), 6.28 (s, 1H), 6.50 (d, 1H), 7.15-7.66 (band, 11H), 8.66 (m, 2H), 8.80 (m, 1H), 8.97 (m, 1H), 10.75 (br s, 1H). ESI-MS: m/z 490.20 (M-H)⁻.

COMPOUND 17

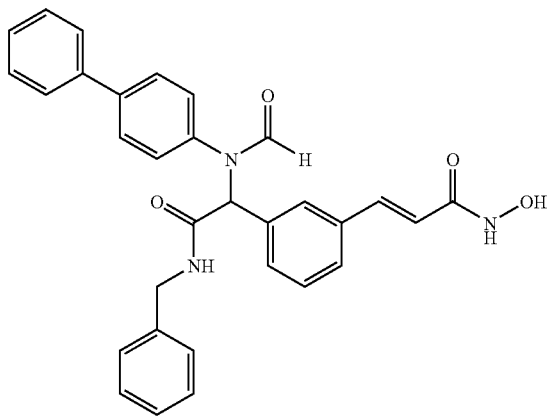

3-{3-[Benzylcarbamoyl-(biphenyl-4-yl-formyl-amino)-methyl]-phenyl}-N-hydroxy-acrylamide ¹H-NMR (400 MHz, DMSO-d₆): δ 4.40 (m, 2H), 6.23 (s, 1H), 6.35 (dd, 2H), 6.10-7.80 (range, 18H), 8.47 (s, 1H), 8.85 (m, 1H), 9.10 (bs, 1H), 10.80 (bs, 1H). ESI-MS: m/z 504.1 (M-H)⁻.

COMPOUND 18

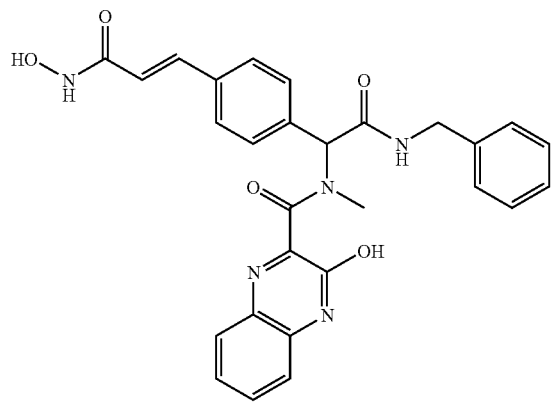

3-Hydroxy-quinoxaline-2-carboxylic acid {benzyl-carbamoyl-[4-(2-hydroxycarbamoyl-vinyl)-phenyl]-methyl}-methyl-amide ¹H NMR (400 MHz, DMSO-d₆): δ 2.92 (s, 3H), 4.35 (dd, 2H), 5.61 (s, 1H), 6.43 (s, 1H), 6.50 (d, 1H), 7.15-7.90 (band, 14H), 8.50 (br s, 1H), 9.19 (br s, 1H), 10.75 (br s, 1H). ESI-MS: m/z 510.20 (M-H)⁻.

COMPOUND 19

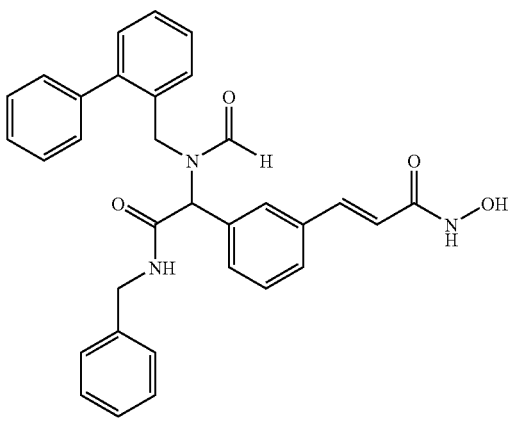

3-{3-[Benzylcarbamoyl-(biphenyl-2-ylmethyl-formyl-amino)-methyl]-phenyl}-N-hydroxy-acrylamide ¹H-NMR (400 MHz, DMSO-d₆): δ 4.33 (m, 2H), 4.85-4.50 (dd, 2H), 5.17 (s, 1H) 5.75 (s, 1H), 6.50-6.20 (dd, 2H), 7.50-6.80 (range, 18H), 8.23 (d, 1H), 8.80-8.50 (d, 1H), 9.10 (bs, 1H), 10.80 (bs, 1H). ESI-MS: m/z 518.1 (M-H)⁻.

COMPOUND 20

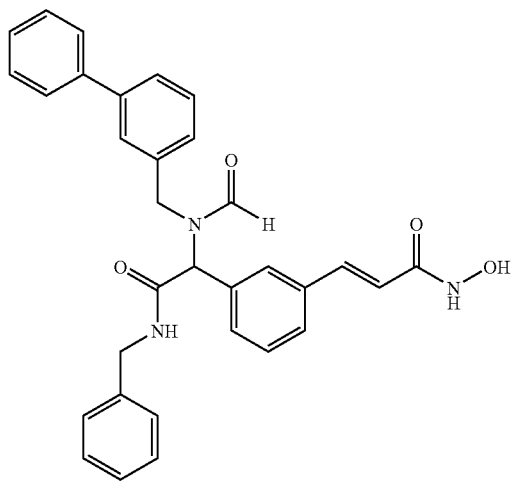

3-{3-[Benzylcarbamoyl-(biphenyl-3-ylmethyl-formyl-amino)-methyl]-phenyl}-N-hydroxy-acrylamide ¹H-NMR (400 MHz, DMSO-d₆): δ 4.33 (m, 2H), 4.60 (m, 2H), 5.40 (s, 1H) 5.96 (s, 1H), 6.44 (dd, 2H), 6.90-7.60 (range, 18H), 8.30 (s, 1H) 8.45 (s, 1H), 8.80 (m, 1H) 9.10 (bs, 1H), 10.80 (bs, 1H). ESI-MS: m/z 518.1 (M-H)⁻.

COMPOUND 21

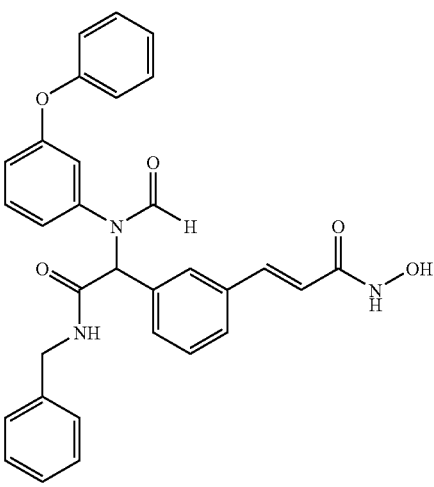

3-(3-{Benzylcarbamoyl-[formyl-(3-phenoxy-phenyl)-amino]-methyl}-phenyl)-N-hydroxy-acrylamide ¹H-NMR (400 MHz, DMSO-d₆): δ 4.35 (m, 2H), 6.15 (s, 1H), 6.34 (d, 2H), 6.68-7.43 (range, 18H), 8.41 (s, 1H), 8.85 (m, 1H) 9.10 (bs, 1H), 10.80 (bs, 1H). ESI-MS: m/z 520.1 (M-H)⁻.

It will be apparent to those skilled in the art that various modifications and variations can be made to the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound comprising the formula:

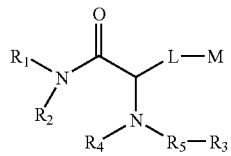

wherein
- $R_1$ comprises a moiety attached to the nitrogen selected from the group consisting of a substituted straight chained $C_{1-12}$ alkyl, $C_{2-12}$ oxaalkyl and $C_{2-12}$ aminoalkyl, where at least one of the substituents is selected from the group consisting of substituted and unsubstituted straight chained $C_{1-12}$ alkyls, $C_{2-12}$ oxaalkyls or $C_{2-12}$ aminoalkyls and substituted and unsubstituted 3, 4, 5, 6, 7 or 8 membered rings;
- $R_2$ comprises a moiety attached to the nitrogen selected from the group consisting of hydrogen, a substituted or unsubstituted straight chained $C_{1-12}$ alkyl, $C_{2-12}$ aminoalkyl, $C_{2-12}$ oxaalkyl, C(O)H, —C(O)—$C_{1-3}$alkyl, and a substituted and unsubstituted 3, 4, 5, 6, 7 or 8 membered ring where all ring atoms are carbon atoms;
- $R_3$ and $R_4$ are each independently selected from the group consisting of hydrogen, a substituted or unsubstituted straight chained $C_{1-12}$ alkyl, $C_{2-12}$ aminoalkyl, $C_{2-12}$ oxaalkyl, C(O)H, —C(O)—$C_{1-3}$alkyl, a substituted or unsubstituted naphthyl, and a substituted and unsubstituted 3, 4, 5, 6, 7 or 8 membered ring where all ring atoms are carbon atoms, provided that $R_4$ is not hydrogen;
- $R_5$ is selected from the group consisting of a carbonyl, a substituted or unsubstituted —$C_{1-3}$ alkyl, a substituted or unsubstituted —$C_{1-3}$ alkyl-C(O), a substituted or unsubstituted —C(O)—$C_{1-3}$ alkyl, and a substituted or unsubstituted —C(O)C(O)$C_{1-3}$ alkyl;
- M is a substituent capable of complexing with a protein metal ion; and
- L is a substituent comprising a chain of 3-12 atoms connecting the M substituent to the carbon atom alpha to the L substituent.

2. A compound according to claim 1 wherein the substituted straight chained $C_{1-12}$ alkyl, $C_{2-12}$ oxaalkyl or $C_{2-12}$ aminoalkyl of $R_1$ is a substituted straight chained $C_{1-4}$ alkyl, $C_{2-4}$ oxaalkyl or $C_{2-4}$ aminoalkyl.

3. A compound according to claim 1 wherein the substituted straight chained $C_{1-12}$ alkyl, $C_{2-12}$ oxaalkyl or $C_{2-12}$ aminoalkyl of $R_1$ is a substituted straight chained $C_{1-4}$ alkyl, $C_{2-4}$ oxaalkyl or $C_{2-4}$ aminoalkyl.

4. A compound according to claim 1 wherein the substituted straight chained $C_{1-12}$ alkyl, $C_{2-12}$ oxaalkyl or $C_{2-12}$ aminoalkyl of $R_1$ is 1, 2, 3, 4, 5, or 6, atoms in length.

5. A compound according to claim 1 wherein the substituent attached to the substituted straight chained $C_{1-12}$ alkyl, $C_{2-12}$ oxaalkyl or $C_{2-12}$ aminoalkyl of $R_1$ renders the alkyl, oxaalkyl or aminoalkyl a branched alkyl, oxaalkyl or aminoalkyl.

6. A compound according to claim 1 wherein the substituent attached to the substituted straight chained $C_{1-12}$ alkyl, $C_{2-12}$ oxaalkyl or $C_{2-12}$ aminoalkyl of $R_1$ is a substituted or unsubstituted five or six membered ring.

7. A compound according to claim 1 wherein the substituent attached to the substituted straight chained $C_{1-12}$ alkyl, $C_{2-12}$ oxaalkyl or $C_{2-12}$ aminoalkyl of $R_1$ is a substituted or unsubstituted aromatic ring.

8. A compound according to claim 1 wherein the substituent attached to the substituted straight chained $C_{1-12}$ alkyl, $C_{2-12}$ oxaalkyl or $C_{2-12}$ aminoalkyl of $R_1$ is a substituted or unsubstituted aromatic ring comprising one or more heteroatoms.

9. A compound according to claim 1 wherein the substituent attached to the substituted straight chained $C_{1-12}$ alkyl, $C_{2-12}$ oxaalkyl or $C_{2-12}$ aminoalkyl of $R_1$ is a substituted or unsubstituted aryl.

10. A compound according to claim 1 wherein $R_2$ comprise a moiety selected from the group consisting of hydrogen and a moiety that has a maximum chain length of non-hydrogen atoms of six or less.

11. A compound according to claim 1 wherein $R_2$ comprise a moiety selected from the group consisting of a $C_{1-4}$ alkyl, $C_{2-4}$ aminoalkyl, $C_{2-4}$ oxaalkyl, —C(O)H, and —C(O)—$C_{1-3}$ alkyl.

12. A compound according to claim 1 wherein one of $R_3$ and $R_4$ comprises a moiety selected from the group consisting of a substituted or unsubstituted straight chained $C_{1-12}$ alkyl, $C_{2-12}$ aminoalkyl, $C_{2-12}$ oxaalkyl, a substituted and unsubstituted naphthyl, and a substituted and unsubstituted 3, 4, 5, 6, 7 or 8 membered ring where all ring atoms are carbon atom, and the other of $R_3$ and $R_4$ is a moiety selected from the group consisting of hydrogen and a moiety that has a maximum chain length of non-hydrogen atoms of six or less.

13. A compound according to claim 1 wherein one of $R_3$ and $R_4$ comprises a moiety selected from the group consisting of a substituted straight chained $C_{1-12}$ alkyl, $C_{2-12}$ aminoalkyl and $C_{2-12}$ oxaalkyl where at least one of the substituents is selected from the group consisting of substituted and unsubstituted straight chained $C_{1-12}$ alkyls, $C_{2-12}$ oxaalkyls, $C_{2-12}$ aminoalkyls, and substituted and unsubstituted 3, 4, 5, 6, 7 or 8 membered rings, and the other of $R_3$ and $R_4$ comprises a member of the group consisting of $C_{1-12}$ alkyl, $C_{2-4}$ aminoalkyl, $C_{2-4}$ oxaalkyl, —C(O)H, and —C(O)—$C_{1-3}$ alkyl.

14. A compound according to claim 1 wherein $R_3$ comprises a substituted 6 membered ring that is substituted beta relative to $R_5$.

15. A compound according to claim 1 wherein $R_3$ comprises a substituted aryl that is substituted meta relative to $R_5$.

16. A compound according to claim 1 wherein $R_3$ comprises a substituted aryl that is substituted meta relative to $R_5$ with a substituent selected from the group consisting of a $C_{1-4}$ alkyl, $C_{2-4}$ aminoalkyl or $C_{2-4}$ oxaalkyl, —C(O)H, and —C(O)—$C_{1-3}$ alkyl.

17. A compound according to claim 1 wherein L comprises a cinnamate moiety.

18. A compound according to claim 1 wherein M comprises a member selected from the group consisting of trifluoroacetyl (—C(O)—$CF_3$), —NH—P(O)OH—$CH_3$, sulfonamides (—$SO_2NH_2$), thiols (—SH), and carbonyl groups having the formula —C(O)—$R_7$ wherein $R_7$ is hydroxylamino, hydroxyl, amino, alkylamino, or an alkyloxy group.

19. A compound according to claim 1 wherein M comprises a hydroxamic acid moiety.

20. A compound comprising the formula:

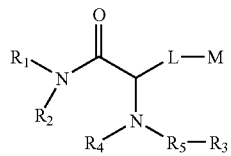

wherein
- $R_1$ and $R_2$ each independently comprise a moiety attached to the nitrogen selected from the group consisting of hydrogen, a substituted or unsubstituted straight chained $C_{1-12}$ alkyl, $C_{2-12}$ aminoalkyl, $C_{2-12}$ oxaalkyl, —C(O)H, —C(O)—$C_{1-3}$ alkyl, and a substituted and unsubstituted 3, 4, 5, 6, 7 or 8 membered ring, with the proviso that $R_1$ and $R_2$ are not both hydrogen;
- one of $R_3$ and $R_4$ is selected from the group consisting of a substituted or unsubstituted straight chained $C_{1-12}$ alkyl, $C_{2-12}$ aminoalky, $C_{2-12}$ oxaalkyl, C(O)H, —C(O)—$C_{1-3}$ alkyl, a substituted and unsubstituted naphthyl, and a substituted or unsubstituted 3, 4, 5, 6, 7 or 8 membered ring where all ring atoms are carbon atoms, and the other of $R_3$ and $R_4$ is a moiety selected from the group consisting of hydrogen and a moiety that has a maximum chain length of non-hydrogen atoms of six or less, provided that $R_4$ is not hydrogen;
- $R_5$ is selected from the group consisting of a carbonyl, a substituted or unsubstituted $C_{1-3}$ alkyl, a substituted or unsubstituted —$C_{1-3}$ alkyl-C(O), a substituted or unsubstituted —C(O)—$C_{1-3}$ alkyl, and a substituted or unsubstituted —C(O)C(O)$C_{1-3}$ alkyl;
- M is a substituent capable of complexing with a protein metal ion; and
- L is a substituent comprising a chain of 3-12 atoms connecting the M substituent to the carbon atom alpha to the L substituent.

21. A compound according to claim 20 wherein one of $R_3$ and $R_4$ is selected from the group consisting of a substituted or unsubstituted straight chained $C_{1-12}$ alkyl, $C_{2-12}$ aminoalkyl, $C_{2-12}$ oxaalkyl, a substituted or unsubstituted naphthyl, a substituted or unsubstituted 3, 4, 5, 6, 7 or 8 membered ring where all ring atoms are carbon atoms and where at least one of the substituents of said one of $R_3$ and $R_4$ is selected from the group consisting of substituted and unsubstituted straight chained $C_{1-12}$ alkyls, $C_{2-12}$ oxaalkyls, $C_{2-12}$ aminoalkyls, and substituted or unsubstituted 3, 4, 5, 6, 7 or 8 membered rings, and the other of $R_3$ and $R_4$ is selected from the group consisting of $C_{1-4}$ alkyl, $C_{2-4}$ aminoalkyl, $C_{2-4}$ oxaalkyl, —C(O)H, and —C(O)—$C_{1-3}$ alkyl.

22. A compound according to claim 20 wherein $R_1$ comprises a moiety attached to the nitrogen selected from the group consisting of a substituted straight chained $C_{1-12}$ alkyl, $C_{2-12}$ oxaalkyl and $C_{2-12}$ aminoalkyl where at least one of the substituents is selected from the group consisting of substituted and unsubstituted straight chained $C_{1-12}$ alkyls, $C_{2-12}$ oxaalkyls, $C_{2-12}$ aminoalkyls, and substituted and unsubstituted 3, 4, 5, 6, 7 or 8 membered rings.

23. A compound according to claim 22 wherein the substituted straight chained $C_{1-12}$ alkyl, $C_{2-12}$ oxaalkyl or $C_{2-12}$ aminoalkyl of $R_1$ is a substituted straight chained $C_{1-6}$ alkyl, $C_{2-6}$ oxaalkyl or $C_{2-4}$ aminoalkyl.

24. A compound according to claim 22 wherein the substituted straight chained $C_{1-12}$ alkyl, $C_{2-12}$ oxaalkyl or $C_{2-12}$ aminoalkyl of $R_1$ is a substituted straight chained $C_{1-4}$ alkyl, $C_{2-4}$ oxaalkyl or $C_{2-4}$ aminoalkyl.

25. A compound according to claim 22 wherein the substituted straight chained $C_{1-12}$ alkyl, $C_{2-12}$ oxaalkyl or $C_{2-12}$ aminoalkyl of $R_1$ is 1, 2, 3, 4, 5, or 6, atoms in length.

26. A compound according to claim 22 wherein the substituent attached to the substituted straight chained $C_{1-12}$ alkyl, $C_{2-12}$ oxaalkyl or $C_{2-12}$ aminoalkyl of $R_1$ renders the alkyl, oxaalkyl or amino alkyl a branched alkyl, oxaalkyl or aminoalkyl.

27. A compound according to claim 22 wherein the substituent attached to the substituted straight chained $C_{1-12}$ alkyl, $C_{2-12}$ oxaalkyl or $C_{2-12}$ aminoalkyl of $R_1$ is a substituted or unsubstituted five or six membered ring.

28. A compound according to claim 22 wherein the substituent attached to the substituted straight chained $C_{1-12}$ alkyl, $C_{2-12}$ oxaalkyl or $C_{2-12}$ aminoalkyl of $R_1$ is a substituted or unsubstituted aromatic ring.

29. A compound according to claim 22 wherein the substituent attached to the substituted straight chained $C_{1-12}$ alkyl, $C_{2-12}$ oxaalkyl or $C_{2-12}$ aminoalkyl of $R_1$ is a substituted or unsubstituted aromatic ring comprising one or more heteroatoms.

30. A compound according to claim 22 wherein the substituent attached to the substituted straight chained $C_{1-12}$ alkyl, $C_{2-12}$ oxaalkyl or $C_{2-12}$ aminoalkyl of $R_1$ is a substituted or unsubstituted aryl.

31. A compound according to claim 20 wherein $R_2$ comprises a moiety selected from the group consisting of hydrogen and a moiety that has a maximum chain length of non-hydrogen atoms of six or less.

32. A compound according to claim 20 wherein $R_2$ comprises a moiety selected from the group consisting of a $C_{1-4}$ alkyl, $C_{2-4}$ aminoalkyl, $C_{2-4}$ oxaalkyl, —C(O)H, and —C(O)—$C_{1-3}$ alkyl.

33. A compound according to claim 20 wherein the other of $R_3$ and $R_4$ is a moiety that has a maximum chain length of non-hydrogen atoms of four or less.

34. A compound according to claim 20 wherein one of $R_3$ and $R_4$ comprises a moiety selected from the group consisting of a substituted straight chained $C_{1-12}$ alkyl, $C_{2-12}$ aminoalkyl and $C_{2-12}$ oxaalkyl where at least one of the substituents is selected from the group consisting of substituted and unsubstituted straight chained $C_{1-12}$ alkyls, $C_{2-12}$ oxaalkyls, $C_{2-12}$ aminoalkyls, and substituted or unsubstituted 3, 4, 5, 6, 7 or 8 membered rings, and the other of $R_3$ and $R_4$ comprises a member of the group consisting of $C_{1-4}$ alkyl, $C_{2-4}$ aminoalkyl, $C_{2-4}$ oxaalkyl, —C(O)H, and —C(O)—$C_{1-3}$ alkyl.

35. A compound according to claim 20 wherein $R_3$ comprises a substituted 6 membered ring that is substituted beta relative to $R_5$.

36. A compound according to claim 20 wherein $R_3$ comprises a substituted aryl that is substituted meta relative to $R_5$.

37. A compound according to claim 20 wherein $R_3$ comprises a substituted aryl that is substituted meta relative to $R_5$ with a substituent selected from the group consisting of a $C_{1-4}$ alkyl, $C_{2-4}$ aminoalkyl, $C_{2-4}$ oxaalkyl, —C(O)H, and —C(O)—$C_{1-3}$ alkyl.

38. A compound according to claim 20 wherein L comprises a cinnamate moiety.

39. A compound according to claim 20 wherein M comprises a member selected from the group consisting of trifluoroacetyl (—C(O)—$CF_3$), —NH—P(O)OH—$CH_3$, sulfonamides (—$SO_2NH_2$), thiols(—SH), and carbonyl groups having the formula —C(O)—$R_7$ wherein $R_7$ is hydroxylamino, hydroxyl, amino, alkylamino, or an alkyloxy group.

40. A compound according to claim 20 wherein M comprises a hydroxamic acid moiety.

41. A compound according to claim 1 wherein one of $R_3$ and $R_4$ comprises a moiety selected from the group consisting of substituted and unsubstituted 3, 4, 5, 6, 7 or 8 membered rings and substituted and unsubstituted fused bicyclic rings, wherein at least one of the substituents is selected from the group consisting of substituted and unsubstituted straight chained $C_{1-12}$ alkyls, $C_{2-12}$ oxaalkyls, $C_{2-12}$ aminoalkyls, and substituted and unsubstituted 3, 4, 5, 6, 7 or 8 membered rings, and the other of $R_3$ and $R_4$ comprises a member of the group consisting of $C_{1-4}$ alkyl, $C_{2-4}$ aminoalkyl, $C_{2-4}$ oxaalkyl, —C(O)H, and —C(O)—$C_{1-3}$ alkyl.

42. A compound according to claim 1 wherein $R_3$ comprises an unsubstituted 6 membered ring.

43. A compound according to claim 1 wherein $R_3$ comprises an unsubstituted aryl.

44. A compound according to claim 1 wherein $R_3$ comprises a naphthyl.

45. A compound according to claim 1 wherein one of $R_3$ and $R_4$ comprises a moiety selected from the group consisting of unsubstituted straight chained $C_{1-2}$ alkyl, $C_{2-12}$ aminoalkyl and $C_{2-12}$ oxaalkyl and the other one of $R_3$ and $R_4$ comprises a member of the group consisting of $C_{1-4}$ alkyl, $C_{2-4}$ aminoalkyl, $C_{2-4}$ oxaalkyl, —C(O)H, and —C(O)—$C_{1-3}$ alkyl.

46. A compound according to claim 1 wherein $R_3$ comprises an unsubstituted straight chained $C_{1-12}$ alkyl.

47. A compound according to claim 1 wherein $R_3$ comprises a substituted straight chained $C_{1-12}$ alkyl, wherein at least one of the substituents is selected from the group consisting of substituted and unsubstituted straight chained $C_{1-12}$ alkyls, $C_{2-12}$ oxaalkyls, $C_{2-12}$ aminoalkyls, and substituted and unsubstituted 3, 4, 5, 6, 7 or 8 membered rings.

48. A compound according to claim 1 wherein $R_3$ is hydrogen.

49. A compound according to claim 20 wherein one of $R_3$ and $R_4$ is selected from the group consisting of a substituted or unsubstituted naphthyl and a substituted or unsubstituted 3, 4, 5, 6, 7, or 8 membered ring where all ring atoms are carbon atoms, and when said one of $R_3$ and $R_4$ is substituted, at least one of the substituents is selected from the group consisting of substituted and unsubstituted straight chained $C_{1-12}$ alkyls, $C_{2-12}$ oxaalkyls, $C_{2-12}$ aminoalkyls, and substituted or unsubstituted 3, 4, 5, 6, 7 or 8 membered rings, and wherein the other of $R_3$ and $R_4$ is selected from the group consisting of $C_{1-4}$ alkyl, $C_{2-4}$ aminoalkyl, $C_{2-4}$ oxaalkyl, —C(O)H, and —C(O)—$C_{1-3}$ alkyl.

50. A compound according to claim 20 wherein $R_3$ comprises an unsubstituted 6 membered ring.

51. A compound according to claim 20 wherein $R_3$ comprises an unsubstituted aryl.

52. A compound according to claim 20 wherein $R_3$ comprises a naphthyl.

53. A compound according to claim 20 wherein one of $R_3$ and $R_4$ comprises a moiety selected from the group consisting of unsubstituted straight chained $C_{1-12}$ alkyl, $C_{2-12}$ aminoalkyl and $C_{2-12}$ oxaalkyl, and the other of $R_3$ and $R_4$ comprises a member of the group consisting of $C_{1-4}$ alkyl, $C_{2-4}$ aminoalkyl, $C_{2-4}$ oxaalkyl, —C(O)H, and —C(O)—$C_{1-3}$ alkyl.

54. A compound according to claim 20 wherein $R_3$ comprises an unsubstituted straight chained $C_{1-12}$ alkyl.

55. A compound according to claim 20 wherein $R_3$ comprises a substituted straight chained $C_{1-12}$ alkyl, wherein at least one of the substituents is selected from the group consisting of substituted and unsubstituted straight chained $C_{1-12}$ alkyls, $C_{2-12}$ oxaalkyls, $C_{2-12}$ aminoalkyls, and substituted and unsubstituted 3, 4, 5, 6, 7 or 8 membered rings.

56. A compound according to claim 20 wherein $R_3$ is hydrogen.

* * * * *

SEQUENCE LISTING

<160> NUMBER OF SEQ ID NOS: 3

<210> SEQ ID NO 1
<211> LENGTH: 377
<212> TYPE: PRT
<213> ORGANISM: Homo Sapien
<220> FEATURE:
<221> NAME/KEY: MISC_FEATURE
<222> LOCATION: (1)..(377)
<223> OTHER INFORMATION: Full length human wild type HDAC8

<400> SEQUENCE: 1

```
Met Glu Glu Pro Glu Pro Ala Asp Ser Gly Gln Ser Leu Val Pro
1               5                   10                  15

Val Tyr Ile Tyr Ser Pro Glu Tyr Val Ser Met Cys Asp Ser Leu Ala
            20                  25                  30

Lys Ile Pro Lys Arg Ala Ser Met Val His Ser Leu Ile Glu Ala Tyr
        35                  40                  45

Ala Leu His Lys Gln Met Arg Ile Val Lys Pro Lys Val Ala Ser Met
    50                  55                  60

Glu Glu Met Ala Ala Phe His Thr Asp Ala Tyr Leu Gln His Leu Gln
65                  70                  75                  80

Lys Val Ser Gln Glu Gly Asp Asp His Pro Asp Ser Ile Glu Tyr
                85                  90                  95

Gly Leu Gly Tyr Asp Cys Pro Ala Thr Glu Gly Ile Phe Asp Tyr Ala
            100                 105                 110

Ala Ala Ile Gly Gly Ala Thr Ile Thr Ala Ala Gln Cys Leu Ile Asp
        115                 120                 125

Gly Met Cys Lys Val Ala Ile Asn Trp Ser Gly Gly Trp His His Ala
    130                 135                 140

Lys Lys Asp Glu Ala Ser Gly Phe Cys Tyr Leu Asn Asp Ala Val Leu
145                 150                 155                 160

Gly Ile Leu Arg Leu Arg Arg Lys Phe Glu Arg Ile Leu Tyr Val Asp
                165                 170                 175

Leu Asp Leu His His Gly Asp Gly Val Glu Asp Ala Phe Ser Phe Thr
            180                 185                 190

Ser Lys Val Met Thr Val Ser Leu His Lys Phe Ser Pro Gly Phe Phe
        195                 200                 205

Pro Gly Thr Gly Asp Val Ser Asp Val Gly Leu Gly Lys Gly Arg Tyr
    210                 215                 220

Tyr Ser Val Asn Val Pro Ile Gln Asp Gly Ile Gln Asp Glu Lys Tyr
225                 230                 235                 240

Tyr Gln Ile Cys Glu Ser Val Leu Lys Glu Val Tyr Gln Ala Phe Asn
                245                 250                 255

Pro Lys Ala Val Val Leu Gln Leu Gly Ala Asp Thr Ile Ala Gly Asp
            260                 265                 270

Pro Met Cys Ser Phe Asn Met Thr Pro Val Gly Ile Gly Lys Cys Leu
        275                 280                 285

Lys Tyr Ile Leu Gln Trp Gln Leu Ala Thr Leu Ile Leu Gly Gly Gly
    290                 295                 300

Gly Tyr Asn Leu Ala Asn Thr Ala Arg Cys Trp Thr Tyr Leu Thr Gly
305                 310                 315                 320

Val Ile Leu Gly Lys Thr Leu Ser Ser Glu Ile Pro Asp His Glu Phe
                325                 330                 335
```

```
Phe Thr Ala Tyr Gly Pro Asp Tyr Val Leu Glu Ile Thr Pro Ser Cys
            340                 345                 350

Arg Pro Asp Arg Asn Glu Pro His Arg Ile Gln Gln Ile Leu Asn Tyr
        355                 360                 365

Ile Lys Gly Asn Leu Lys His Val Val
    370                 375

<210> SEQ ID NO 2
<211> LENGTH: 1134
<212> TYPE: DNA
<213> ORGANISM: Homo Sapien
<220> FEATURE:
<221> NAME/KEY: misc_feature
<222> LOCATION: (1)..(1134)
<223> OTHER INFORMATION: Human cDNA sequence for full length human wild
      type HDAC8

<400> SEQUENCE: 2
atggaggagc cggaggaacc ggcggacagt gggcagtcgc tggtcccggt ttatatctat      60
agtcccgagt atgtcagtat gtgtgactcc ctggccaaga tccccaaacg ggccagtatg     120
gtgcattctt tgattgaagc atatgcactg cataagcaga tgaggatagt taagcctaaa     180
gtggcctcca tggaggagat ggccgccttc cacactgatg cttatctgca gcatctccag     240
aaggtcagcc aagagggcga tgatgatcat ccggactcca tagaatatgg gctaggttat     300
gactgcccag ccactgaagg gatatttgac tatgcagcag ctataggagg ggctacgatc     360
acagctgccc aatgcctgat tgacggaatg tgcaaagtag caattaactg gtctggaggg     420
tggcatcatg caaagaaaga tgaagcatct ggtttttgtt atctcaatga tgctgtcctg     480
ggaatattac gattgcgacg gaaatttgag cgtattctct acgtggattt ggatctgcac     540
catggagatg gtgtagaaga cgcattcagt ttcacctcca aagtcatgac cgtgtccctg     600
cacaaattct ccccaggatt ttcccaggga acaggtgacg tgtctgatgt tggcctaggg     660
aagggacggt actacagtgt aaatgtgccc attcaggatg gcatacaaga tgaaaaatat     720
taccagatct gtgaaagtgt actaaaggaa gtataccaag cctttaatcc caaagcagtg     780
gtcttacagc tgggagctga cacaatagct ggggatccca tgtgctcctt aacatgact      840 ccagtgggaa ttggcaagtg tcttaagtac atccttcaat ggcagttggc aacactcatt     900
ttgggaggag gaggctataa ccttgccaac acggctcgat gctggacata cttgaccggg     960
gtcatcctag gaaaaacact atcctctgag atcccagatc atgagttttt cacagcatat    1020
ggtcctgatt atgtgctgga aatcacgcca agctgccggc cagaccgcaa tgagcccac     1080 cgaatccaac aaatcctcaa ctacatcaaa gggaatctga gcatgtggt ctag           1134

<210> SEQ ID NO 3
<211> LENGTH: 385
<212> TYPE: PRT
<213> ORGANISM: Artificial Sequence
<220> FEATURE:
<223> OTHER INFORMATION: Amino acid sequence for residues 1-377 of HDAC8
      with a cleavable N-terminal 6x-histidine tag
<220> FEATURE:
<221> NAME/KEY: MISC_FEATURE
<222> LOCATION: (1)..(8)
<223> OTHER INFORMATION: n-terminal 6x-histidine tag
<220> FEATURE:
<221> NAME/KEY: MISC_FEATURE
<222> LOCATION: (9)..(385)
<223> OTHER INFORMATION: residues 1-377 of HDAC8

<400> SEQUENCE: 3
```

-continued

```
Met His His His His His Pro Met Glu Glu Pro Glu Pro Ala
1               5               10              15

Asp Ser Gly Gln Ser Leu Val Pro Val Tyr Ile Tyr Ser Pro Glu Tyr
            20              25              30

Val Ser Met Cys Asp Ser Leu Ala Lys Ile Pro Lys Arg Ala Ser Met
        35              40              45

Val His Ser Leu Ile Glu Ala Tyr Ala Leu His Lys Gln Met Arg Ile
    50              55              60

Val Lys Pro Lys Val Ala Ser Met Glu Glu Met Ala Ala Phe His Thr
65              70              75              80

Asp Ala Tyr Leu Gln His Leu Gln Lys Val Ser Gln Glu Gly Asp Asp
                85              90              95

Asp His Pro Asp Ser Ile Glu Tyr Gly Leu Gly Tyr Asp Cys Pro Ala
            100             105             110

Thr Glu Gly Ile Phe Asp Tyr Ala Ala Ala Ile Gly Gly Ala Thr Ile
        115             120             125

Thr Ala Ala Gln Cys Leu Ile Asp Gly Met Cys Lys Val Ala Ile Asn
    130             135             140

Trp Ser Gly Gly Trp His His Ala Lys Lys Asp Glu Ala Ser Gly Phe
145             150             155             160

Cys Tyr Leu Asn Asp Ala Val Leu Gly Ile Leu Arg Leu Arg Arg Lys
                165             170             175

Phe Glu Arg Ile Leu Tyr Val Asp Leu Asp Leu His His Gly Asp Gly
            180             185             190

Val Glu Asp Ala Phe Ser Phe Thr Ser Lys Val Met Thr Val Ser Leu
        195             200             205

His Lys Phe Ser Pro Gly Phe Phe Pro Gly Thr Gly Asp Val Ser Asp
    210             215             220

Val Gly Leu Gly Lys Gly Arg Tyr Tyr Ser Val Asn Val Pro Ile Gln
225             230             235             240

Asp Gly Ile Gln Asp Glu Lys Tyr Tyr Gln Ile Cys Glu Ser Val Leu
                245             250             255

Lys Glu Val Tyr Gln Ala Phe Asn Pro Lys Ala Val Leu Gln Leu
            260             265             270

Gly Ala Asp Thr Ile Ala Gly Asp Pro Met Cys Ser Phe Asn Met Thr
        275             280             285

Pro Val Gly Ile Gly Lys Cys Leu Lys Tyr Ile Leu Gln Trp Gln Leu
    290             295             300

Ala Thr Leu Ile Leu Gly Gly Gly Tyr Asn Leu Ala Asn Thr Ala
305             310             315             320

Arg Cys Trp Thr Tyr Leu Thr Gly Val Ile Leu Gly Lys Thr Leu Ser
                325             330             335

Ser Glu Ile Pro Asp His Glu Phe Phe Thr Ala Tyr Gly Pro Asp Tyr
            340             345             350

Val Leu Glu Ile Thr Pro Ser Cys Arg Pro Asp Arg Asn Glu Pro His
        355             360             365

Arg Ile Gln Gln Ile Leu Asn Tyr Ile Lys Gly Asn Leu Lys His Val
    370             375             380

Val
385
```